(12) United States Patent
Luo et al.

(10) Patent No.: US 12,293,841 B1
(45) Date of Patent: May 6, 2025

(54) SYSTEMS AND METHODS FOR METABOLIC OUTCOME PREDICTIONS

(71) Applicant: Welldoc, Inc., Columbia, MD (US)

(72) Inventors: Junjie Luo, Columbia, MD (US); Abhimanyu Kumbara, Columbia, MD (US); Anand K. Iyer, Potomac, MD (US); Mansur E. Shomali, Columbia, MD (US); Guodong Gao, Columbia, MD (US)

(73) Assignee: Welldoc, Inc., Columbia, MD (US)

( * ) Notice: Subject to any disclaimer, the term of this patent is extended or adjusted under 35 U.S.C. 154(b) by 0 days.

(21) Appl. No.: 18/891,499

(22) Filed: Sep. 20, 2024

Related U.S. Application Data

(60) Provisional application No. 63/653,489, filed on May 30, 2024, provisional application No. 63/572,514, filed on Apr. 1, 2024.

(51) Int. Cl.
| | | |
|---|---|---|
| *G16H 50/30* | (2018.01) | |
| *G16H 10/60* | (2018.01) | |
| *G16H 20/10* | (2018.01) | |
| *G16H 20/60* | (2018.01) | |
| *G16H 50/20* | (2018.01) | |

(52) U.S. Cl.
CPC ............ *G16H 50/30* (2018.01); *G16H 10/60* (2018.01); *G16H 20/10* (2018.01); *G16H 20/60* (2018.01); *G16H 50/20* (2018.01)

(58) Field of Classification Search
CPC ........ G16H 50/30; G16H 10/60; G16H 20/10; G16H 20/60; G16H 50/20
See application file for complete search history.

(56) References Cited

U.S. PATENT DOCUMENTS

| | | | |
|---|---|---|---|
| 12,207,950 B2* | 1/2025 | Catani | A61B 5/0022 |
| 2021/0398641 A1* | 12/2021 | Catani | G16H 20/60 |
| 2024/0242834 A1* | 7/2024 | Deng | A61B 5/4839 |

* cited by examiner

*Primary Examiner* — Gregory D. Moseley
(74) *Attorney, Agent, or Firm* — Bookoff McAndrews, PLLC

(57) ABSTRACT

A method may receive historical metabolic values for an individual having a first medical condition. A method may provide a first subset of the historical metabolic values to a machine learning model to train a generative machine learning model. A method may generate a first predicted metabolic value based on the first subset of historical metabolic values. A method may calculate a root mean square error (RMSE) between the first predicted metabolic value and a corresponding actual metabolic value of a second subset of historical metabolic values. A method may train the generative machine learning model to minimize the RMSE. A method may generate a trained generative machine learning model based on the training.

15 Claims, 52 Drawing Sheets

| QUESTION | OUTCOME VARIABLE TO OBSERVE | QUESTION # | SCENARIO |
|---|---|---|---|
| CAN WE USE EARLY STAGE DIGITAL HEALTH & CGM ENGAGEMENT TO PREDICT FUTURE TIR OUTCOMES? | TIR | 1 | 2-STATE DIRECTION PREDICTION: GETTING BETTER OR WORSE? |
| | TIR | 2 | 3-STATE DIRECTION PREDICTION: GETTING BETTER, REMAINING SAME, GETTING WORSE |
| | TIR | 3 | 2-STATE VALUE PREDICTION: PREDICTING IF THE FUTURE TIR VALUE WILL BE > OR < 70% (GOAL) |
| CAN WE USE EARLY STAGE DIGITAL HEALTH & CGM ENGAGEMENT TO PREDICT FUTURE TIR OUTCOMES? | GRI | 4 | 2-STATE DIRECTION PREDICTION: GETTING BETTER OR WORSE? |
| | GRI | 5 | 3-STATE DIRECTION PREDICTION: GETTING BETTER, REMAINING SAME, GETTING WORSE |
| | GRI | 6 | 2-STATE VALUE PREDICTION: PREDICTING IF THE FUTURE GRI VALUE WILL BE > OR < 40 (GOAL) |
| CAN WE USE EARLY STAGE DIGITAL HEALTH & CGM ENGAGEMENT TO PREDICT FUTURE DIGITAL HEALTH ENGAGEMENT? | MEDAL ENGAGEMENT | 7 | 2-STATE DIRECTION PREDICTION: IS FUTURE ENGAGEMENT HIGH OR LOW FOR EACH OF MEDICATIONS, EDUCATION, DIET, ACTIVITY, LABS? |
| | MANUAL ENTRY MEDAL ENGAGEMENT | 8 | 2-STATE DIRECTION PREDICTION: IS FUTURE ENGAGEMENT HIGH OR LOW FOR EACH OF MEDICATIONS, EDUCATION, DIET, LABS? |
| | CGM WEAR TIME | 9 | 2-STATE VALUE PREDICTION: IS FUTURE CGM WEAR > OR < 70% OF TIME (I.E., 70% OF THE TOTAL 2880 POSSIBLE READINGS IN A WEEK) |

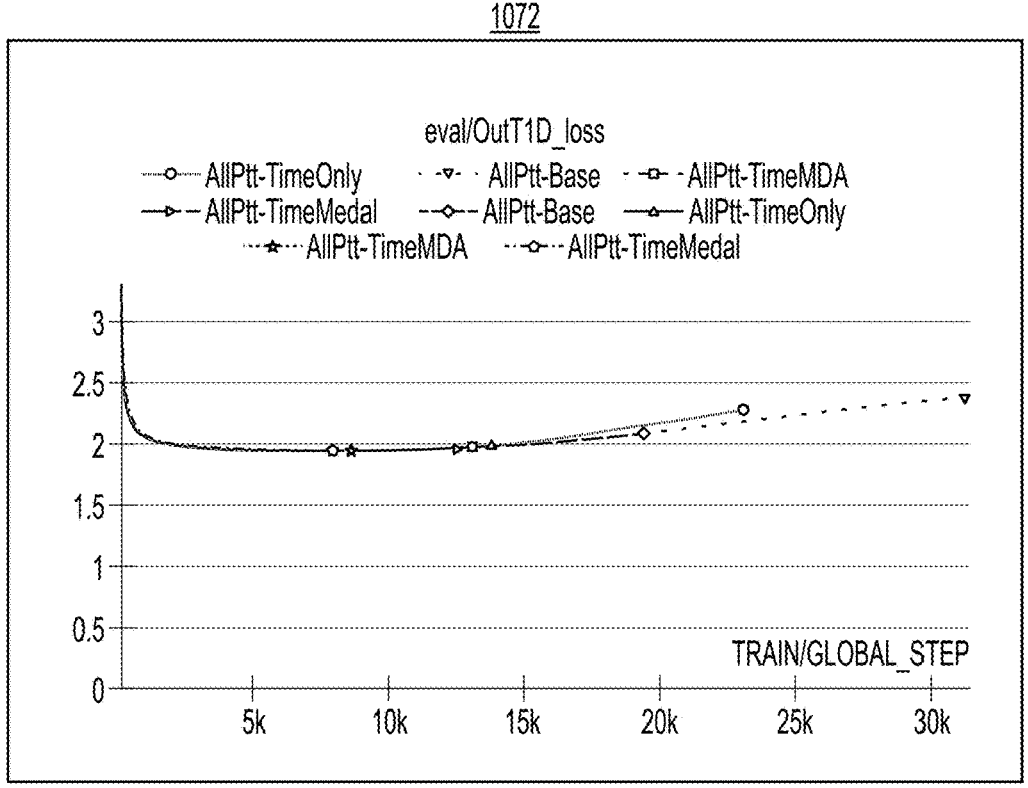
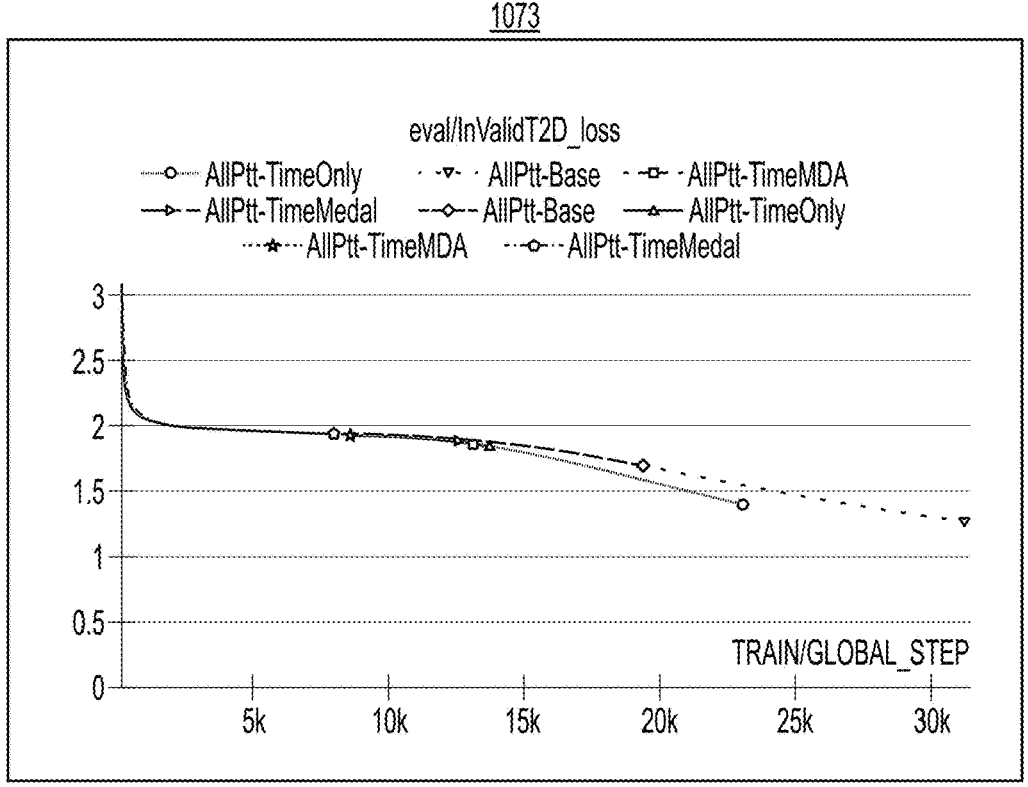
FIG. 10G (CONT. 1)

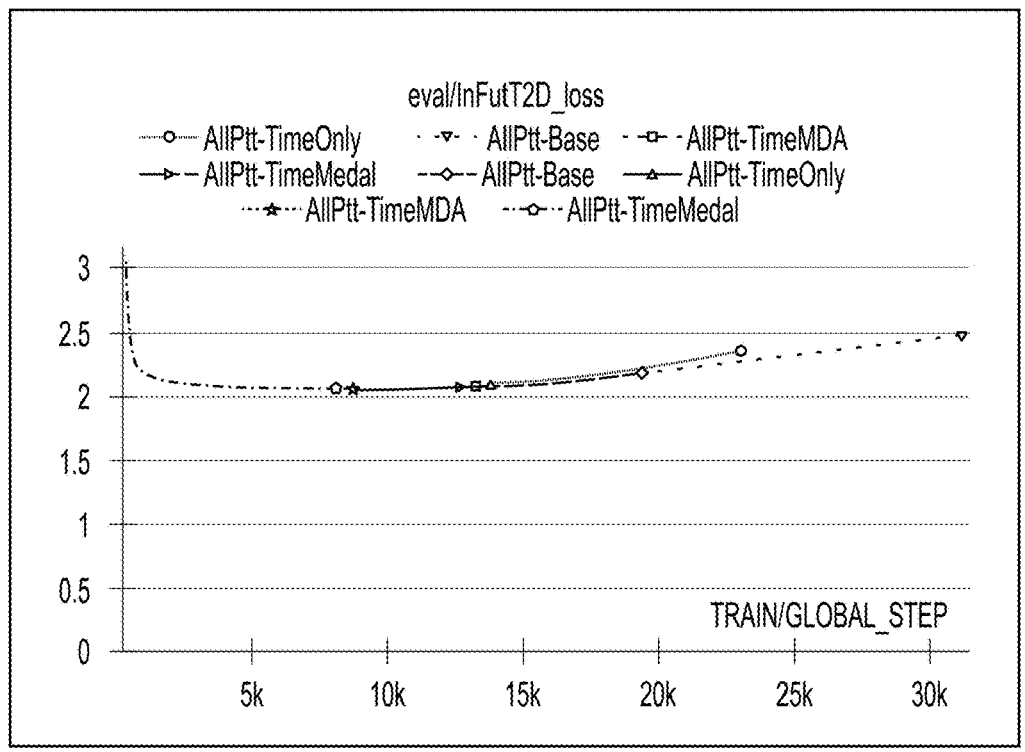
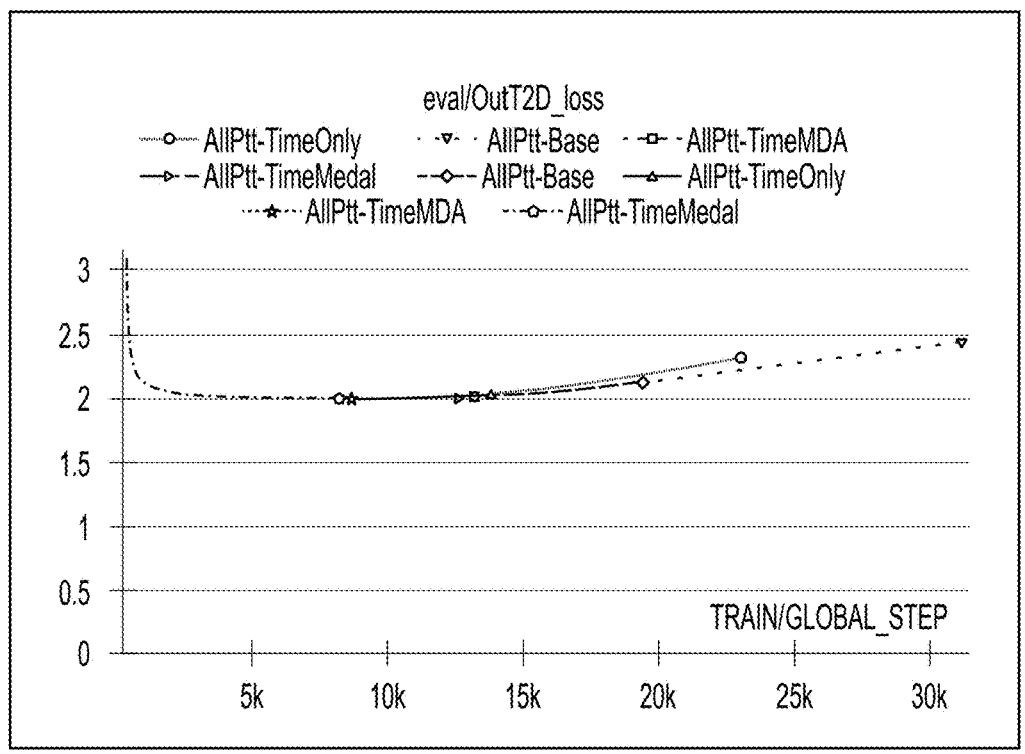
FIG. 10G (CONT. 2)

1080

1081

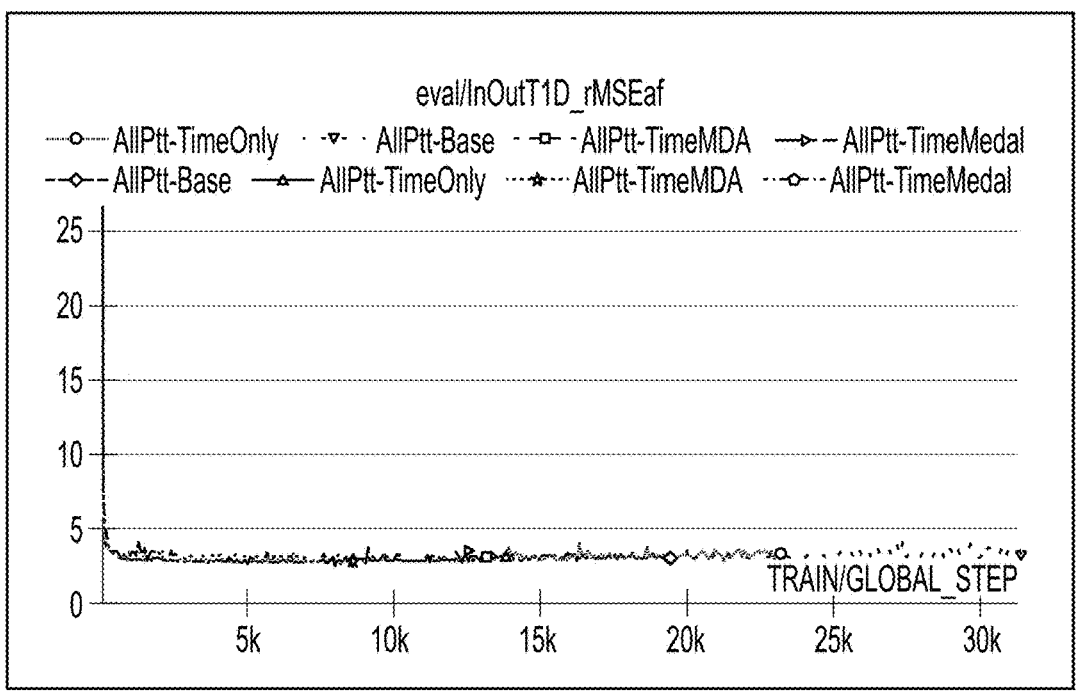
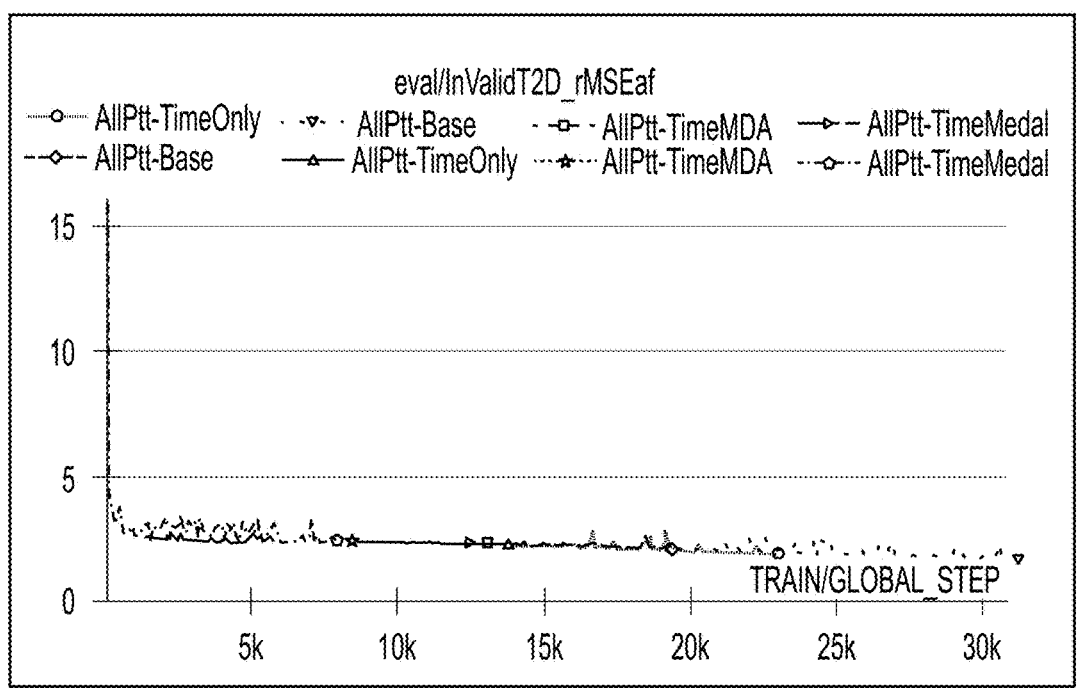
FIG. 10H (CONT. 1)

1084
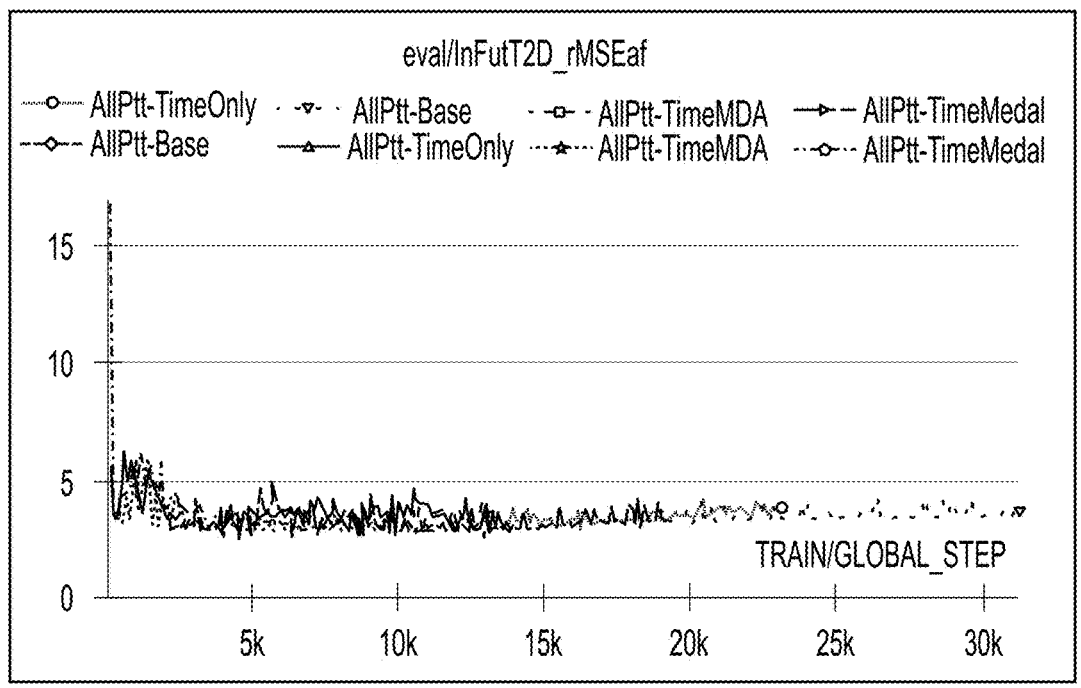
1085
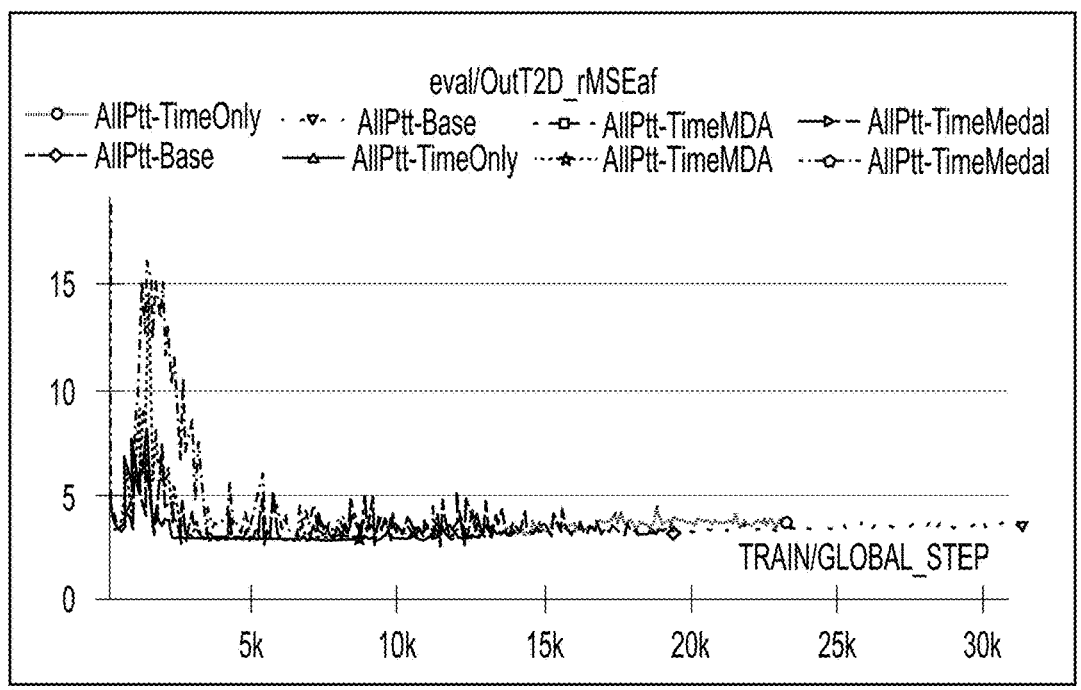
FIG. 10H (CONT. 2)

1092
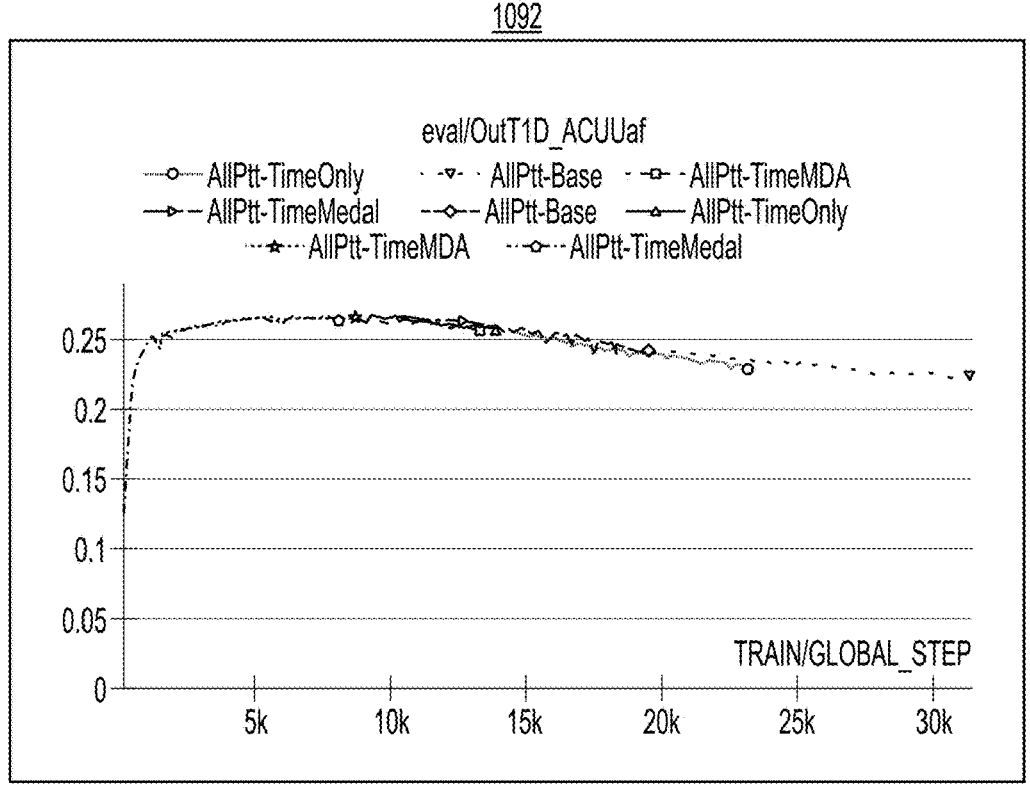
1093
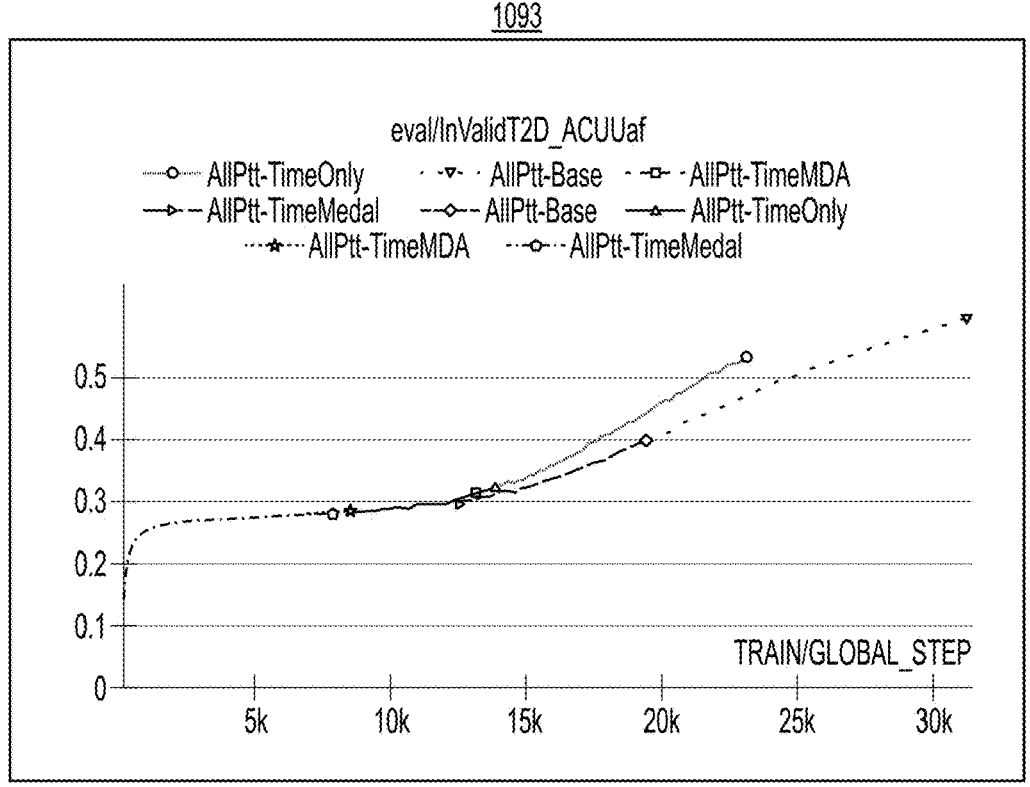
FIG. 10I (CONT. 1)

1094
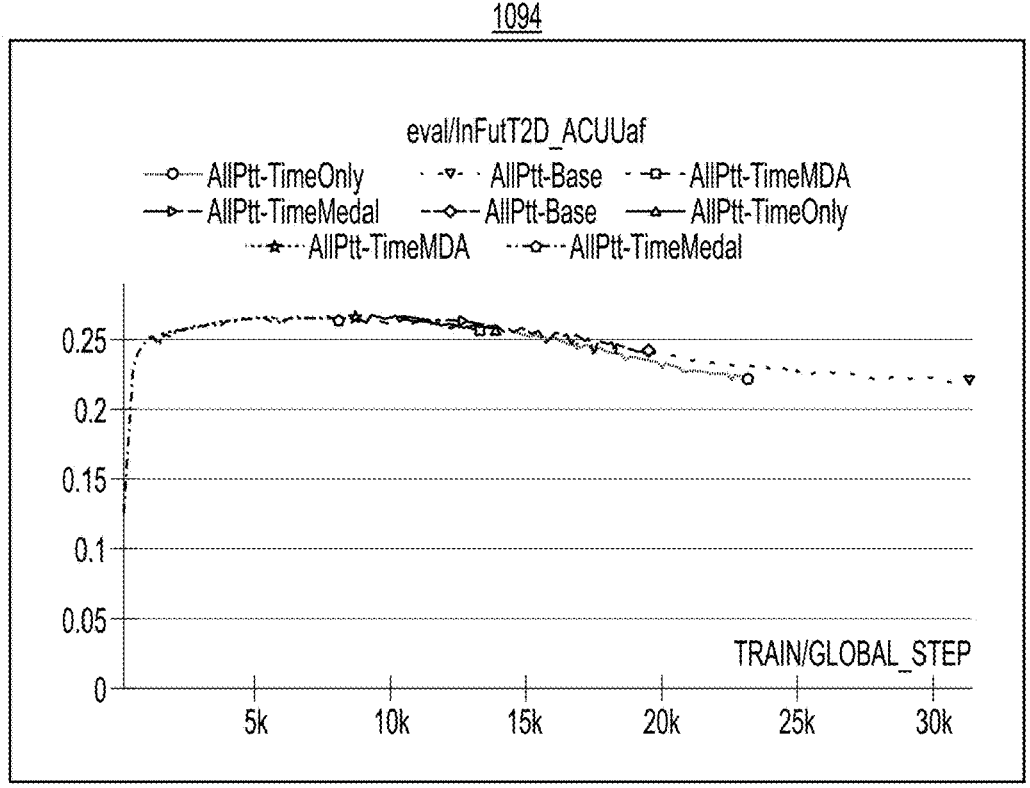
1095
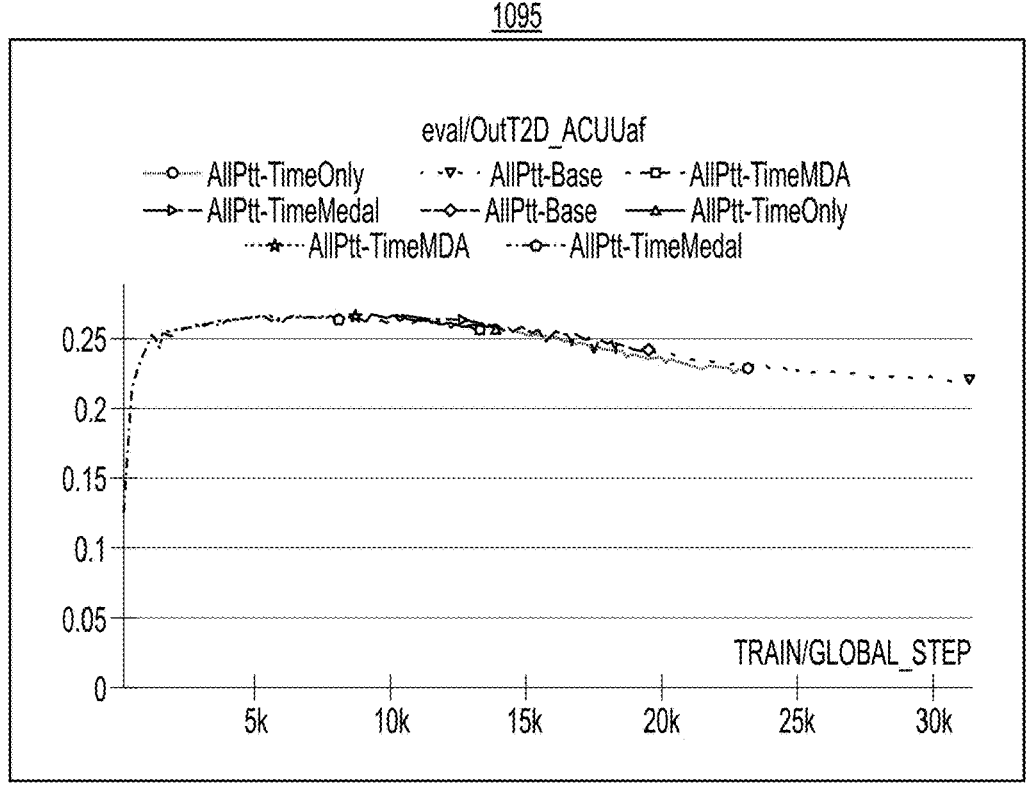
FIG. 10I (CONT. 2)

EVALUATION BASED ON TRAINING DATA FOR INDIVIDUALS WITH TYPE 2 DIABETES

TYPE 1 PATIENTS — EVALUATION METRICS: RMSE (mg/dL)

1170

| DATASET CATEGORY | CONDITION | 30 MIN | 60 MIN | 120 MIN |
|---|---|---|---|---|
| BASELINE (LITERATURE) | TYPE 1 | ~20 | ~30 | NaN |

1175

| DATASET CATEGORY | CONDITION | 30 MIN | 60 MIN | 120 MIN |
|---|---|---|---|---|
| IN_VALID | TYPE 1 | 12.02 | 22.08 | 36.82 |
| IN_TEST | TYPE 1 | 12.66 | 22.59 | 37.15 |
| OUT_TEST | TYPE 1 | 13.50 | 24.15 | 40.41 |
| OUT | TYPE 1 | 12.95 | 23.53 | 39.44 |

TYPE 1 PATIENTS

1180

| DATASET CATEGORY | CONDITION | 30 MIN | 60 MIN | 120 MIN |
|---|---|---|---|---|
| IN_VALID | TYPE 2 | 10.43 | 18.44 | 30.11 |
| IN_TEST | TYPE 2 | 10.96 | 19.12 | 30.86 |
| OUT_TEST | TYPE 2 | 10.32 | 17.85 | 28.40 |
| OUT | TYPE 2 | 9.74 | 16.93 | 27.18 |

| | RMSE (FUTURE 30 MIN) | | | | | | |
|---|---|---|---|---|---|---|---|
| | T1D PATIENT EVALUATION SET | | | | T2D PATIENT EVALUATION SET | | |
| MODEL | BASELINE | T1 & T2 TRAIN SET | T1 TRAIN SET | MODEL | BASELINE | T1 & T2 TRAIN SET | T2 TRAIN SET |
| TEST | 18.00 | 12.00 | 12.17 | TEST | N/A | 10.56 | 10.52 |
| FUTURE TEST | N/A | 12.99 | 13.02 | FUTURE TEST | N/A | 11.25 | 11.17 |
| HOLD-OUT | N/A | 12.81 | 12.81 | HOLD-OUT | N/A | 10.45 | 10.41 |
| HOLD-OUT FUTURE | N/A | 13.54 | 13.46 | HOLD-OUT FUTURE | N/A | 11.24 | 11.23 |

FIG. 11E

| RMSE (FUTURE 1 HOUR) | | | | | | | |
|---|---|---|---|---|---|---|---|
| T1D PATIENTS AS EVALUATION DATASET | | | | T2D PATIENTS AS EVALUATION DATASET | | | |
| MODEL | BASELINE | T1 & T2 TRAIN SET | T1 TRAIN SET | MODEL | BASELINE | T1 & T2 TRAIN SET | T2 TRAIN SET |
| TEST | 30.00 | 22.21 | 22.45 | TEST | N/A | 18.42 | 18.26 |
| FUTURE TEST | N/A | 23.19 | 23.30 | FUTURE TEST | N/A | 19.21 | 19.01 |
| HOLD-OUT | N/A | 23.52 | 23.54 | HOLD-OUT | N/A | 17.58 | 17.47 |
| HOLD-OUT FUTURE | N/A | 24.27 | 24.31 | HOLD-OUT FUTURE | N/A | 18.53 | 18.49 |

RMSE (FUTURE 2 HOURS)

| | T1D PATIENTS AS EVALUATION DATASET | | | | T2D PATIENTS AS EVALUATION DATASET | | | |
|---|---|---|---|---|---|---|---|---|
| MODEL | BASELINE | T1 & T2 TRAIN SET | T1 TRAIN SET | | MODEL | BASELINE | T1 & T2 TRAIN SET | T2 TRAIN SET |
| TEST | N/A | 37.39 | 37.96 | | TEST | N/A | 29.95 | 29.51 |
| FUTURE TEST | N/A | 38.40 | 38.77 | | FUTURE TEST | N/A | 30.69 | 30.20 |
| HOLD-OUT | N/A | 39.80 | 40.08 | | HOLD-OUT | N/A | 27.69 | 27.35 |
| HOLD-OUT FUTURE | N/A | 40.80 | 41.27 | | HOLD-OUT FUTURE | N/A | 28.90 | 28.64 |

FIG. 11G

| PAPER | PATIENT SAMPLE | DATA SIZE | TRAINING METHOD | RESULT |
|---|---|---|---|---|
| LI2019 CRNNFORGLUCOSEPRED | 10 VIRTUAL T1D PATIENTS, 10 REAL T1D PATIENTS. | REAL PATIENTS, 6 MONTHS (5 PATIENT-YEARS) | 50% TRAINING AND 50% TESTING | 30-MINUTE: RMSE = 21.07 ± 2.35 mg/dL<br>60-MINUTE: RMSE = 33.27 ± 4.79 mg/dL |
| LI2019GLUNET | 20 VIRTUAL T1D PATIENTS, 10+6 REAL T1D PATIENTS | ABC4D PROJECT DATASET: 6 MONTHS (5 PATIENT-YEARS)<br>OHIOT1DM DATASET: 8 WEEKS(1 PATIENT-YEAR) | 50% TRAINING AND 50% TESTING | ABC4D ADULT DATASET:<br>30-MINUTE: RMSE = 19.19 ± 2.74 mg/dL<br>60-MINUTE: RMSE = 31.78 ± 4.94 mg/dL<br>OHIOT1DM DATASET:<br>30-MINUTE: RMSE = 19.28 ± 2.76 mg/dL<br>60-MINUTE: RMSE = 31.83 ± 3.49 mg/dL |
| ZHU2022FCNN PERSONALIZEDBGPRED | 12+12+15 REAL T1D PATIENTS | OHIOT1DM DATASET: 8 WEEKS<br>ARISES DATASET: 6 WEEKS<br>ABC4D DATASET: 6 MONTHS | 80% TRAINING AND 20% TESTING | OHIOT1DM DATASET:<br>30-MINUTE: RMSE = 18.64 ± 2.6 mg/dL<br>60-MINUTE: RMSE = 31.07 ± 3.62 mg/dL<br>ARISES DATASET:<br>30-MINUTE: RMSE = 20.23 ± 3.38 mg/dL<br>60-MINUTE: RMSE = 35.40 ± 7.04 mg/dL<br>ABC4D DATASET:<br>30-MINUTE: RMSE = 20.25 ± 2.6 mg/dL<br>60-MINUTE: RMSE = 34.03 ± 4.74 mg/dL |

FIG. 11H

| PAPER | PATIENT SAMPLE | DATA SIZE | TRAINING METHOD | RESULT |
|---|---|---|---|---|
| ZHU2022ENHANCETYPE1-DIABETESNPJ(RNN) | 12 REAL T1D PATIENTS | REAL PATIENTS, 6 WEEKS (1.3 PATIENT-YEARS) | 50% TRAINING AND 50% TESTING | 30-MINUTE RMSE = 20.92 ± 3.55 mg/dL 45-MINUTE RMSE = 28.99 ± 4.41 mg/dL 60-MINUTE RMSE = 35.28 ± 5.77 mg/dL |
| ZHU2023ETFTFORMULTI-HORIZONGLUCOSEPRED | 12 REAL T1D PATIENTS | | 50% TRAINING AND 50% TESTING | 30-MINUTE RMSE = 19.09 ± 2.47 mg/dL 60-MINUTE RMSE = 32.31 ± 2.84 mg/dL |

*FIG. 11I*

SYSTEMS AND METHODS FOR METABOLIC OUTCOME PREDICTIONS

CROSS-REFERENCE TO RELATED APPLICATION(S)

This application claims the benefit of priority to U.S. Provisional Application No. 63/572,514, filed on Apr. 1, 2024; and U.S. Provisional Application No. 63/653,489, filed on May 30, 2024, each of which is incorporated herein by reference in its entireties.

TECHNICAL FIELD

The present disclosure relates generally to predicting a user's future metabolic values (e.g., glucose), and, in some embodiments, more specifically to using one or more machine learning models to determine health related predictions for other metabolic values that can include blood pressure, weight, BMI among others.

INTRODUCTION

Increased healthcare costs have limited user access to appropriate care. At the same time, increased provider workloads lead to limited physician-user interactions. Chronic conditions offer a particularly difficult set of challenges for both providers and the patients who suffer from the condition. Often, one particular source is related to the lack of continuous data around certain metabolic values that can inform the current state and past trends to offer the healthcare provider insights into alternate treatment pathways that can be taken with a patient. Diabetes treatment, for example, often relies on sporadic readings (e.g., finger-stick blood glucose readings) that do not provide ample continuous data to effectively provide treatment options or sufficient data for making predictions of health and/or delivering engagement outcomes. These readings are often used in isolation such that providers are forced to make changes and recommendations based on one, two or very few readings. Any medical, dietary, and/or lifestyle changes recommended as a result of a given reading are therefore limited given the limited data received via the sporadic readings.

The introduction provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

In some aspects, the techniques described herein relate to a computer-implemented method for training a machine learning model for predicting metabolic values, the method including: sensing an individual's glucose levels by a continuous glucose monitoring (CGM) device over a period of time receiving the individual's glucose levels collected by the CGM device over the period of time; determining a first glycemia risk index (GRI) value based on a first amount of time the user is hypoglycemic during the period of time and a second amount of time the user is hyperglycemic during the period of time; determining a time in range (TIR) value of the user's glucose level, wherein the determined TIR value is based on an amount of time the user's glucose level is within a threshold band over the time period, wherein the threshold band is generated based on the lifestyle, habits, and medical test results of the patient; receiving historical metabolic values for an individual having a first medical condition, wherein the individuals historical metabolic values are associated with heart rates, heart related values, ketone values, weight values, cortisol values, hormone levels, body electrical values, repertory values, and the glucose levels collected by the CGM device; providing a first subset of the historical metabolic values, supplementary variables, and supplementary conditions to a machine learning model to train a generative machine learning model, wherein the first subset of the historical metabolic values includes the CGM values over the period of time, wherein the supplementary variables include the TIR value and GRI value, and wherein the supplementary condition is an anticipated dosage, anticipated time for taking a given medication, anticipated example exercise, or an anticipated example food to be consumed by the given individual; generating a first predicted metabolic value based on the first subset of the historical metabolic values, wherein generating the first predicted metabolic value based on the first subset of the historical metabolic values includes generating the first predicted metabolic value at a first interval; calculating a root mean square error (RMSE) between the first predicted metabolic value and a corresponding actual metabolic value of a second subset of the historical metabolic values; training the generative machine learning model to minimize the RMSE, wherein the generative machine learning model is trained to learn the distribution of the historical metabolic values, the generative machine learning model is a statistical model of the joint probability distribution on the historical metabolic values and the predicted metabolic values, wherein the generative machine learning model is used to generate random instances of the historical metabolic values and may select a given historical metabolic value from the random instances that corresponds to a highest probability of occurring, wherein the generative machine learning model determines a conditional probability of a target metabolic value based on historical metabolic values, and wherein the generative machine learning model learns patterns and structure of training data that includes the historical metabolic values to generate new data that has similar characteristic; generating a trained generative machine learning model based on the training, wherein the trained generative machine learning model outputs recommendations for causing the predicted metabolic value to comply with a metabolic value goal or range.

In some aspects, the techniques described herein relate to a computer-implemented method, wherein the first predicted metabolic value is one or more future CGM values over the period of time.

In some aspects, the techniques described herein relate to a computer-implemented method, wherein the first medical condition includes at least one of type 1 diabetes or type 2 diabetes.

In some aspects, the techniques described herein relate to a computer-implemented method, wherein the first interval includes at least one of 30 minutes, 60 minutes, or 2 hours.

In some aspects, the techniques described herein relate to a computer-implemented method, further including: providing recent metabolic values associated with a first individual to the trained generative machine learning model; receiving a first predicted metabolic value from a trained generative machine learning model based on the recent metabolic values; comparing the first predicted metabolic value to a threshold metabolic value; determining a first action based on comparing the first predicted metabolic value to the threshold metabolic value.

In some aspects, the techniques described herein relate to a computer-implemented method for using a metabolic prediction trained machine learning model, the method including: sensing an individual's glucose levels by a continuous glucose monitoring (CGM) device over a period of time; receiving an individual's glucose levels collected by the CGM device over a period of time; receiving historical metabolic values for an individual having a first medical condition, wherein the individuals historical metabolic values are associated with heart rates, heart related values, ketone values, weight values, cortisol values, hormone levels, body electrical values, repertory values, and the glucose levels collected by the CGM device; providing a first subset of the historical metabolic values to a machine learning model to train a generative machine learning model, wherein the first subset of the historical metabolic values includes CGM values over the period of time; generating a first predicted metabolic value based on the first subset of the historical metabolic values, wherein generating the first predicted metabolic value based on the first subset of the historical metabolic values includes generating the first predicted metabolic value at a first interval; calculating a root mean square error (RMSE) between the first predicted metabolic value and a corresponding actual metabolic value of a second subset of the historical metabolic values; training the generative machine learning model to minimize the RMSE, wherein the generative machine learning model is trained to learn the distribution of the historical metabolic values, the generative machine learning model is a statistical model of the joint probability distribution on the historical metabolic values and the predicted metabolic values, wherein the generative machine learning model is used to generate random instances of the historical metabolic values and may select a given historical metabolic value from the random instances that corresponds to a highest probability of occurring, wherein the generative machine learning model determines a conditional probability of a target metabolic value based on historical metabolic values, and wherein the generative machine learning model learns patterns and structure of training data that includes the historical metabolic values to generate new data that has similar characteristic; generating a trained generative machine learning model based on the training; providing recent metabolic values associated with a first individual to a trained generative learning model trained to output predicted metabolic values; receiving a first predicted metabolic value from a trained generative machine learning model based on the recent metabolic values; comparing first predicted metabolic value to a threshold metabolic value; determining a first action based on comparing the first predicted metabolic value to the threshold metabolic value, wherein the first action includes: determining a dosage of a medication based comparing the first predicted metabolic value to the threshold metabolic value; determining a first time to administer the dosage of medication based on the comparing the first predicted metabolic value to the threshold metabolic value; and triggering a medical device to administer the dosage of medication at the first time, wherein the medication is insulin and the medical device is an insulin pump; determining a second action based on comparing the first predicted metabolic value to the threshold metabolic value; wherein the second action includes: providing a notification to the individual, wherein the notification includes at least one of an exercise recommendation, a fluid intake recommendation, a rest recommendation, an education recommendation, a food recommendation, or an insulin recommendation.

In some aspects, the techniques described herein relate to a computer-implemented method, wherein the second action includes sending an instruction to an application of a user device via an application programming interface (API).

In some aspects, the techniques described herein relate to a computer-implemented method, wherein the second action includes generating a food order through a mobile application.

In some aspects, the techniques described herein relate to a computer-implemented method, wherein the second action includes: receiving a plurality of food items available to a user based on accessing a database; identifying a subset of food items from the plurality of food items based on comparing the first predicted metabolic value to the threshold metabolic value; and outputting the subset of food items to a user device.

In some aspects, the techniques described herein relate to a computer-implemented method, wherein the second action includes generating an alert to medical services.

In some aspects, the techniques described herein relate to a system for predicting metabolic values, the system including: a memory having processor-readable instructions stored therein; and a processor configured to access the memory and execute the processor-readable instructions, which, when executed by the processor configures the processor to perform a method, the method including: sensing an individual's glucose levels by a continuous glucose monitoring (CGM) device over a period of time receiving the individual's glucose levels collected by the CGM device over the period of time; determining a first glycemia risk index (GRI) value based on a first amount of time the user is hypoglycemic during the period of time and a second amount of time the user is hyperglycemic during the period of time; determining a time in range (TIR) value of the user's glucose level, wherein the determined TIR value is based on an amount of time the user's glucose level is within a threshold band over the time period, wherein the threshold band is generated based on the lifestyle, habits, and medical test results of the patient; receiving historical metabolic values for an individual having a first medical condition, wherein the individuals historical metabolic values are associated with heart rates, heart related values, ketone values, weight values, cortisol values, hormone levels, body electrical values, repertory values, and the glucose levels collected by the CGM device; providing a first subset of the historical metabolic values, supplementary variables, and supplementary conditions to a machine learning model to train a generative machine learning model, wherein the first subset of the historical metabolic values includes the CGM values over the period of time, wherein the supplementary variables include the TIR value and GRI value, and wherein the supplementary condition is an anticipated dosage, anticipated time for taking a given medication, anticipated example exercise, or an anticipated example food to be consumed by the given individual; generating a first predicted metabolic value based on the first subset of the historical metabolic values, wherein generating the first predicted metabolic value based on the first subset of the historical metabolic values includes generating the first predicted metabolic value at a first interval; calculating a root mean square error (RMSE) between the first predicted metabolic value and a corresponding actual metabolic value of a second subset of the historical metabolic values; training the generative machine learning model to minimize the RMSE, wherein the generative machine learning model is trained to learn the distribution of the historical metabolic values, the generative machine learning model is a statistical model of the joint probability distribution on the historical metabolic values and the predicted metabolic values, wherein the generative machine learning model is used to generate random instances of the historical metabolic values and may select a given historical metabolic value from the random instances that corresponds to a highest probability of occurring, wherein the generative machine learning model determines a conditional probability of a target metabolic value based on historical metabolic values, and wherein the generative machine learning model learns patterns and structure of training data that includes the historical metabolic values to generate new data that has similar characteristic; generating a trained generative machine learning model based on the training, wherein the trained generative machine learning model outputs recommendations for causing the predicted metabolic value to comply with a metabolic value goal or range.

In some aspects, the techniques described herein relate to a system, wherein the first predicted metabolic value is one or more future CGM values over the period of time In some aspects, the techniques described herein relate to a system, wherein the first medical condition includes at least one of type 1 diabetes or type 2 diabetes.

In some aspects, the techniques described herein relate to a system, wherein the first interval includes at least one of 30 minutes, 60 minutes, or 2 hours.

In some aspects, the techniques described herein relate to a system, further including: providing recent metabolic values associated with a first individual to the trained generative machine learning model; receiving a first predicted metabolic value from a trained generative machine learning model based on the recent metabolic values; comparing the first predicted metabolic value to a threshold metabolic value; determining a first action based on comparing the first predicted metabolic value to the threshold metabolic value.

BRIEF DESCRIPTION OF THE DRAWINGS

The accompanying drawings, which are incorporated in and constitute a part of this specification, illustrate examples of the disclosure and together with the description, serve to explain the principles of the disclosure.

FIG. 7A-7B show diagrams depicting the use of glucose and engagement data to predict future health and engagement outcomes, in accordance with one or more embodiments.

FIGS. 11A-11D show example CGM prediction outputs for groups of individuals, in accordance with one or more embodiments.

FIGS. 11E-11G show example CGM prediction outputs for groups of individuals, in accordance with one or more embodiments.

FIGS. 11H-11I show example CGM prediction outputs using conventional methods, in accordance with one or more embodiments.

DETAILED DESCRIPTION

Reference will now be made in detail to examples of the disclosure, which are illustrated in the accompanying drawings. Wherever possible, the same reference numbers will be used throughout the drawings to refer to the same or like parts.

In the discussion that follows, relative terms such as "about," "substantially," "approximately," etc. are used to indicate a possible variation of ±10% in a stated numeric value. It should be noted that the description set forth herein is merely illustrative in nature and is not intended to limit the examples of the subject matter, or the application and uses of such examples. Any embodiments described herein as exemplary are not to be construed as preferred or advantageous over other embodiments. Rather, as alluded to above, the term "exemplary" is used in the sense of example or "illustrative," rather than "ideal." The terms "comprise," "include," "have," "with," and any variations thereof are used synonymously to denote or describe a non-exclusive inclusion. As such, a process, method, article, or apparatus that uses such terms does not include only those steps, structure or elements but may include other steps, structures or elements not expressly listed or inherent to such process, method, article, or apparatus. Further, the terms "first," "second," and the like, herein do not denote any order, quantity, or importance, but rather are used to distinguish one element from another. Moreover, the terms "a" and "an" herein do not denote a limitation of quantity, but rather denote the presence of at least one of the referenced item.

Healthcare and Computing Environment

Figure 1:
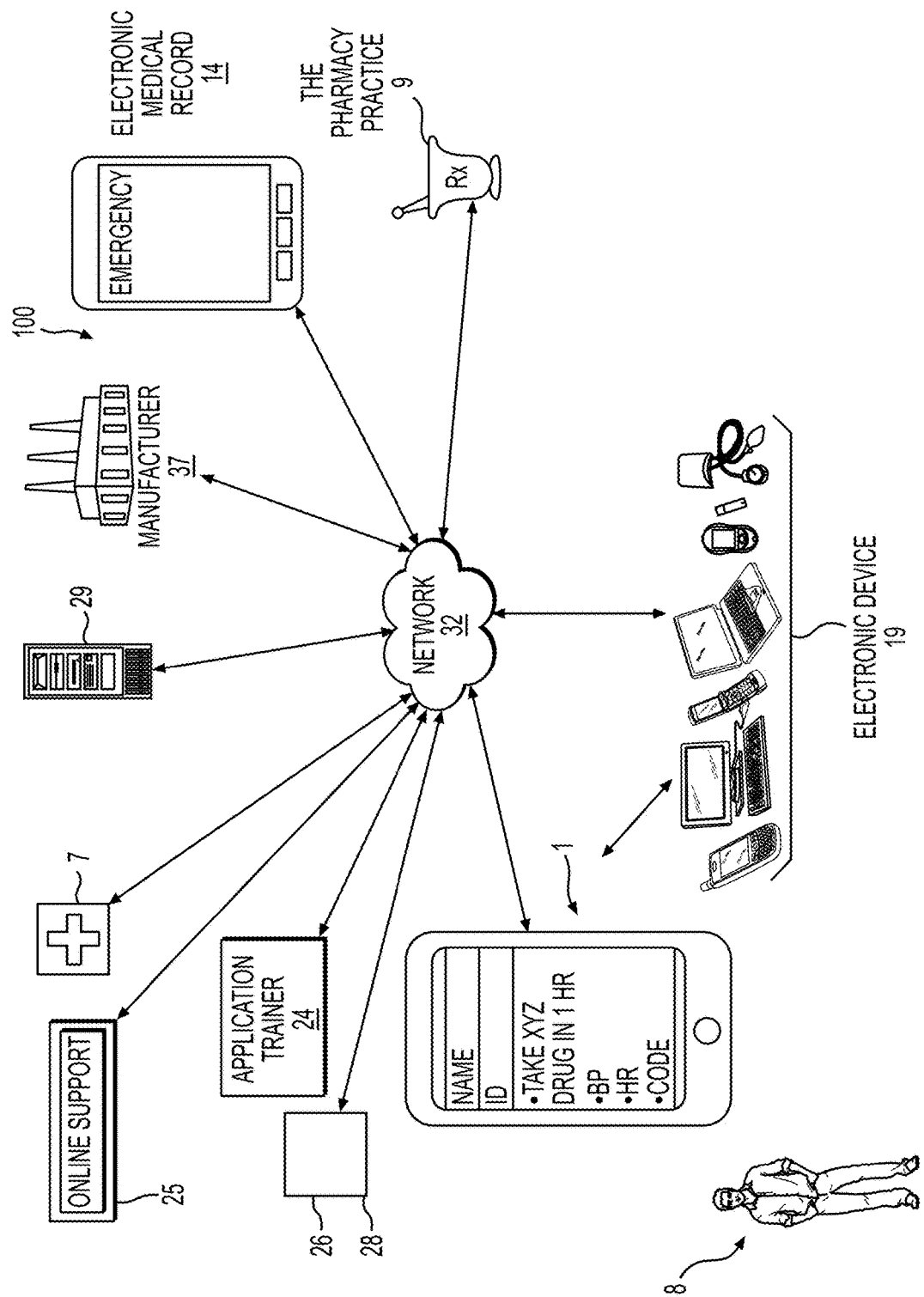
FIG. 1 shows a schematic illustration of a health management system, in accordance with one or more embodiments.

FIG. 1 is a block diagram of a health management system 100, according to an example of the present disclosure. A user (e.g., a patient, consumer, or the like) 8 having an electronic device 19, such as a mobile device, computer, medical device, or any other electronic device configured to access an electronic network 32, such as the Internet, may communicate with or otherwise access a mobile health (mHealth) application 1. In some examples, network 32 may include wireless or wired links, such as mobile telephone networks, Wi-Fi, LANs, WANs, Bluetooth, near-field communication (NFC), or other suitable forms of network communication. Multiple electronic devices 19 may be configured to access electronic network 32. A user 8 may access mHealth application 1 with a single account linked to multiple electronic devices 19 (e.g., via one or more of a mobile phone, a tablet, and a laptop computer). Electronic device 19 also may include, but is not limited to, mobile health devices, a desktop computer or workstation, a laptop computer, a mobile handset, a personal digital assistant (PDA), a cellular telephone, a network appliance, a camera, a smart phone, a smart watch, an enhanced general packet radio service (EGPRS) mobile phone, a media player, a navigation device, a game console, a set-top box, a biometric sensing device with communication capabilities, a smart TV, or any combination of these or other types of computing devices having at least one processor, a local memory, a display (e.g., a monitor or touchscreen display), one or more user input devices, and a network communication interface. The electronic device 19 may include any type or combination of input/output devices, such as a display monitor, keyboard, touchpad, accelerometer, gyroscope, mouse, touchscreen, camera, a projector, a touch panel, a pointing device, a scrolling device, a button, a switch, a motion sensor, an audio sensor, a pressure sensor, a thermal sensor, and/or microphone. Electronic devices 19 also may communicate with each other by any suitable wired or wireless means (e.g., via Wi-Fi, radio frequency (RF), infrared (IR), Bluetooth, Near Field Communication, or any other suitable means) to send and receive information.

mHealth application 1 may be implemented in communication with other entities or networks to send and receive information. In some examples, mHealth application 1 may communicate with one or more applications associated with the user 8 such as, e.g., exercise tracking (e.g., step tracking) applications and/or other health-related applications. mHealth application 1 may be configured to import data from the other applications to analyze and use in generating treatment plans for the user 8. For example, mHealth application 1 may import activity tracking data from another application and use that data to identify patterns between user 8 exercise and glucose values collected prior to the use of mHealth application 1. mHealth application 1 also may import any other suitable data from other mobile health applications such as, e.g., blood pressure, body mass index (BMI), glycated hemoglobin (A1C), exercise type, exercise duration, exercise distance, calories burned, total steps, exercise date, exercise start and stop times, and sleep. mHealth application 1 also may export data to other mobile applications, including, e.g., other mobile health applications having social or interactive features. A healthcare provider 7, such as a physician, may prescribe the application. However, it is also contemplated that mHealth application 1 may not require a prescription, e.g., that it may be a commercially available consumer application accessible without a prescription from a digital distribution platform for computer software. mHealth application 1 may be tailored to a specific user 8 and may be activated in person by the user 8 by visiting a pharmacy 9 or other authorized entity. For example, the user 8 may receive an access code from the pharmacy that authorizes access to mHealth application 1. The user 8 may receive training on using mHealth application 1 by a mHealth support system 25 and/or application trainer 24. mHealth application 1 may include programming 28 of various forms, such as machine learning programming algorithms 26. The user treatment plan may include a prescription (e.g., for a drug, device, and/or therapy), which may be dispensed by the pharmacy 9. The pharmacy 9 may allow the refill of the prescribed product/therapy after receiving authorization based on the user's compliance with his/her healthcare treatment plan. The authorization may be received by the pharmacy 9 by a communication from mHealth application 1, via, e.g., the network 32 and various servers 29. Use of the drug or other medical product/therapy also may be sent to the manufacturer 37 over the network 32 to inform the manufacturer 37 of the amount of medical product or therapy being used by user 8. This information may assist the manufacturer 37 in assessing demand and planning supply of the medical product or therapy. The healthcare provider 7 also may receive a report based on the user information received by mHealth application 1, and may update the user treatment plan based on this information. The user's electronic medical record (EMR) 14 also may be automatically updated via the network 32 based on the user information, which may include electronically transmitted user 8 feedback on the application, received by mHealth application 1. Healthcare provider 7 may be any suitable healthcare provider including, e.g., a doctor, specialist, nurse, educator, social worker, medical assistant (MA), physician assistant or associate (PA), or the like.

Figure 2:
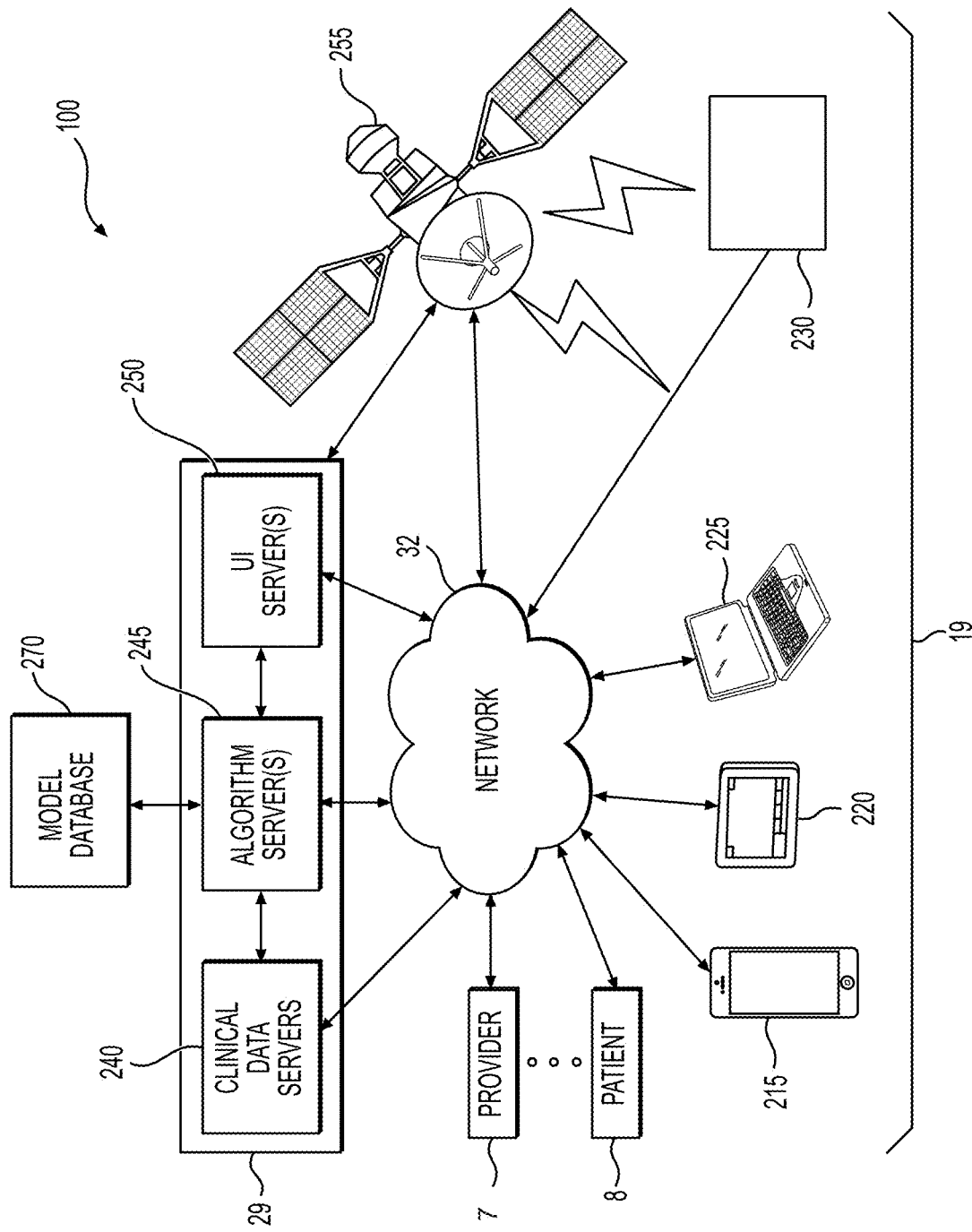
FIG. 2 shows a schematic illustration of a portion of the health management system of FIG. 1, in accordance with one or more embodiments.

FIG. 2 is a schematic diagram of additional aspects of system 100. For example, the system 100 may access decision models stored on a decision model database 270 via network 32. The retrieved decision models may be used for display and/or processing by one or more electronic devices 19, such as a mobile device 215, a tablet device 220, a computer 225 (e.g., a laptop or desktop), a kiosk 230 (e.g., at a kiosk, pharmacy, clinic, or hospital having medical and/or prescription information), and/or any device connected to network 32.

In the example shown in FIG. 2, mobile device 215, tablet device 220, and computer 225 each may be equipped with or include, for example, a global positioning system (GPS) receiver for obtaining and reporting location information, e.g., GPS data, via network 32 to and from any of servers 29 and/or one or more GPS satellites 255.

Each of electronic devices 19, including mobile device 215, tablet device 220, computer 225, and/or kiosk 230, may be configured to send and receive data (e.g., clinical information) to and from a system of servers 29 over network 32. Each of devices 19 may receive information, such as clinical data via the network 32 from servers 29. Servers 29 may include clinical data server 240, algorithm server 245, user interface (UI) server 250, and/or any other suitable servers. Electronic device 19 may include a user interface that is in data communication with UI server 250 via network 32. Each server may access the decision model database 270 to retrieve decision models. Each server may include memory, a processor, and/or a database. For example, the clinical data server 240 may have a processor configured to retrieve clinical data from a provider's database and/or a patient's electronic medical record. The algorithm server 245 may have a database that includes various algorithms, and a processor configured to process the clinical data. The UI server 250 may be configured to receive and process user 8 input, such as clinical decision preferences. The satellite 255 may be configured to send and receive information between servers 29 and devices 19.

The clinical data server 240 may receive clinical data, such as data regarding the user from the electronic device 19 via the network 32 or indirectly via the UI server 250. The clinical data server 240 may save the information in memory, such as a computer readable memory.

The clinical data server 240 also may be in communication with one or more other servers, such as the algorithm server 245 and/or external servers. The servers 29 may include data about provider preferences, and/or user 8 health history. In addition, the clinical data server 240 may include data from other users. The algorithm server 245 may include machine learning, and/or other suitable algorithms. The algorithm server 245 also may be in communication with other external servers and may be updated as desired. For example, the algorithm server 245 may be updated with new algorithms, more powerful programming, and/or more data. The clinical data server 240 and/or the algorithm server 245 may process the information and transmit data to the model database 270 for processing. In one example, algorithm server(s) 245 may obtain a pattern definition in a simple format, predict several time steps in the future by using models, e.g., Markov models, Gaussian, Bayesian, PCA (principal component analysis), multi-variate linear or non-linear regression, and/or classification models such as linear discriminant functions, nonlinear discriminant functions, synthetic discriminant functions random forest algorithms and the like, optimize results based on its predictions, detect transition between patterns, obtain abstract data and extract information to infer higher levels of knowledge, combine higher and lower levels of information to understand about the user 8 and clinical behaviors, infer from multi-temporal (e.g., different time scales) data and associated information, use variable order Markov models, and/or reduce noise over time by employing slope-based and curve smoothing algorithms, clustering algorithms, such as k-means clustering.

Each server in the system of servers 29, including clinical data server 240, algorithm server 245, and UI server 250, may represent any of various types of servers including, but not limited to, a web server, an application server, a proxy server, a network server, or a server farm. Each server in the system of servers 29 may be implemented using, for example, any general-purpose computer capable of serving data to other computing devices including, but not limited to, devices 19 or any other computing device (not shown) via network 32. Such a general-purpose computer can include, but is not limited to, a server device having a processor and memory for executing and storing instructions. The memory may include any type of random access memory (RAM) or read-only memory (ROM) embodied in a physical storage medium, such as magnetic storage including floppy disk, hard disk, or magnetic tape; semiconductor storage such as solid-state disk (SSD) or flash memory; optical disc storage; or magneto-optical disc storage. Software may include one or more applications and an operating system. Hardware can include, but is not limited to, a processor, memory, and graphical UI display. Each server also may have multiple processors and multiple shared or separate memory components that are configured to function together within, for example, a clustered computing environment or server farm.

Figure 3A:
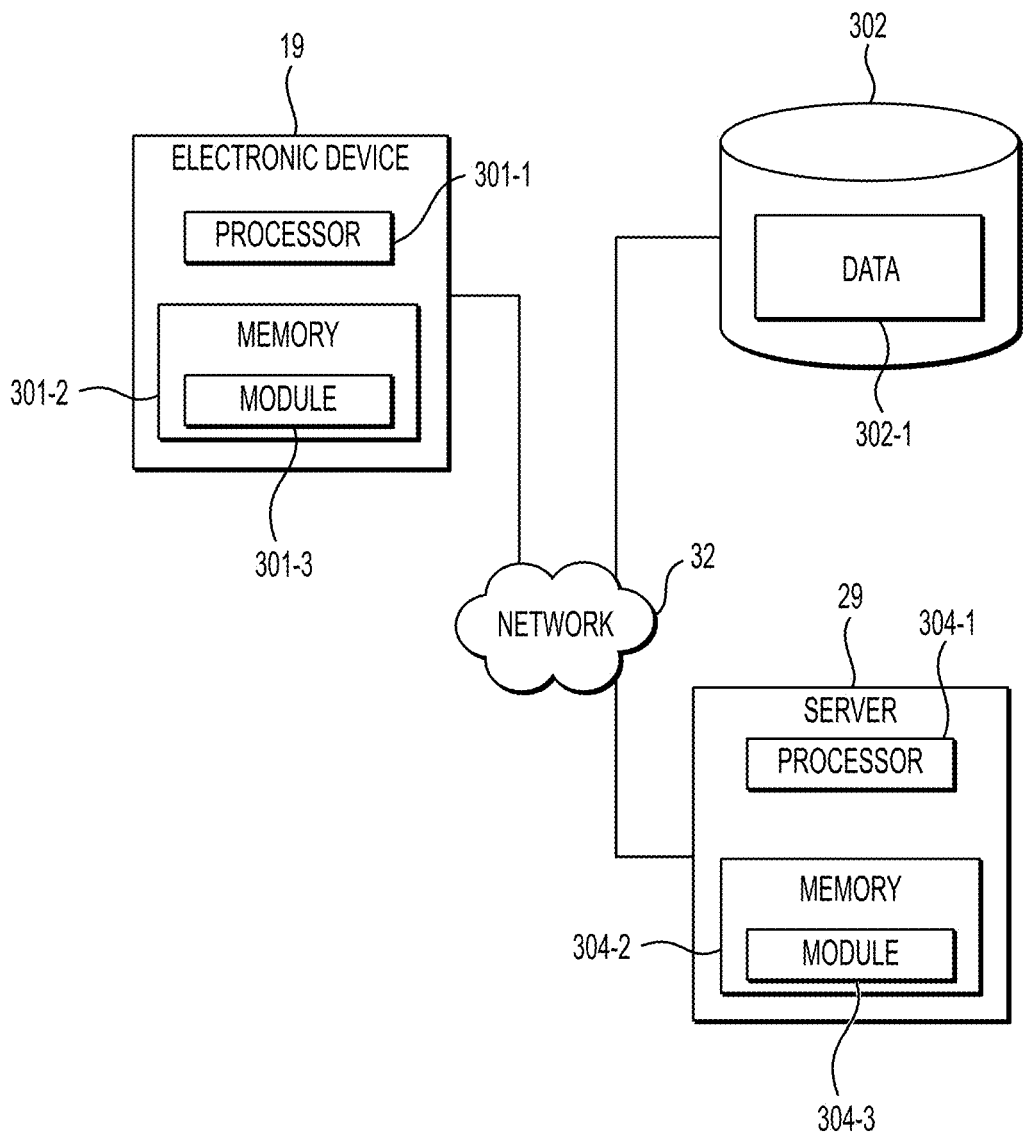
FIG. 3A shows a schematic illustration of another portion of the health management system of FIG. 1, in accordance with one or more embodiments.

FIG. 3A is another representation of a portion of system 100 showing additional details of electronic device 19 and a server 29. Electronic device 19 and server 29 each may contain one or more processors, such as processors 301-1 and 304-1. Processors 301-1 and 304-1 each may be a central processing unit, a microprocessor, a general purpose processor, an application specific processor, or any device that executes instructions. Electronic device 19 and server 29 also may include one or more memories, such as memories 301-2 and 304-2 that store one or more software modules. Memories 301-2 and 304-2 may be implemented using any computer-readable storage medium, such as hard drives, CDs, DVDs, flash memory, RAM, ROM, etc. Memory 301-2 may store a module 301-3, which may be executed by processor 301-1. Similarly, memory 304-2 may store a module 304-3, which may be executed by processor 304-1.

Electronic device 19 may further comprise one or more UIs. The UI may allow one or more interfaces to present information to a user 8, such as a plan or intervention. The UI may be web-based, such as a web page, or a stand-alone application. The UI also may be configured to accept information about a user 8, such as data inputs and user feedback. The user 8 may manually enter the information, or it may be entered automatically. In an example, the user 8 (or the user's caretaker) may enter information such as when medication was taken or what food and drink the user 8 consumed. Electronic device 19 also may include testing equipment (not shown) or an interface for receiving information from testing equipment. Testing equipment may include, for example, a blood glucose meter, glucose meter, heart rate monitor, weight scale, blood pressure cuff, or the like. The electronic device 19 also may include one or more sensors (not shown), such as a camera, microphone, or accelerometer, for collecting feedback from a user 8. In one example, the device may include a glucose meter for reading and automatically reporting the user's glucose levels.

Electronic device 19 also may include a presentation layer. The presentation layer may be a web browser, application, messaging interface (e.g., e-mail, instant message, SMS, etc.), etc. The electronic device 19 may present notifications, alerts, reading materials, references, guides, reminders, or suggestions to a user 8 via presentation layer. For example, the presentation layer may present articles that are determined to be relevant to the user 8, reminders to purchase medications, tutorials on topics (e.g., a tutorial on carbohydrates), testimonials from others with similar symptoms, and/or one or more goals (e.g., a carbohydrate counting goal). The presentation layer also may present information such as a tutorial (e.g., a user guide or instructional video) and/or enable communications between the healthcare provider, and the user 8, e.g., patient. The communications between the healthcare provider, and the user 8, e.g., patient, may be via electronic messaging (e.g., e-mail or SMS), voice, or real-time video. One or more of these items may be presented based on a treatment plan or an updated treatment plan, as described later. The presentation layer also may be used to receive feedback from a user.

The system 100 also may include one or more databases, such as a database 302. Database 302 may be implemented using any database technology known to one of ordinary skill in the art, such as relational database technology or object-oriented database technology. Database 302 may store data 302-1. Data 302-1 may include a knowledge base for making inferences, statistical models, and/or user information. Data 302-1, or portions thereof, may be alternatively or simultaneously stored in server 29 or electronic device 19.

System 100 can be used for a wide range of applications, including, for example, addressing a user's healthcare, maintaining a user's finances, and monitoring and tracking a user's nutrition and/or sleep. In some embodiments of system 100, any received data may be stored in the databases in an encrypted form to increase security of the data against unauthorized access and complying with HIPAA privacy, and/or other legal, healthcare, financial, or other regulations.

For any server or server systems 29 depicted in system 100, the server or server system may include one or more databases. In an example, databases may be any type of data store or recording medium that may be used to store any type of data. For example, database 302 may store data received by or processed by server 29 including information related to a user's treatment plan, including timings and dosages associated with each prescribed medication of a treatment plan. Database 302 also may store information related to the user 8 including their literacy level related to each of a plurality of prescribed medications.

Figure 3B:
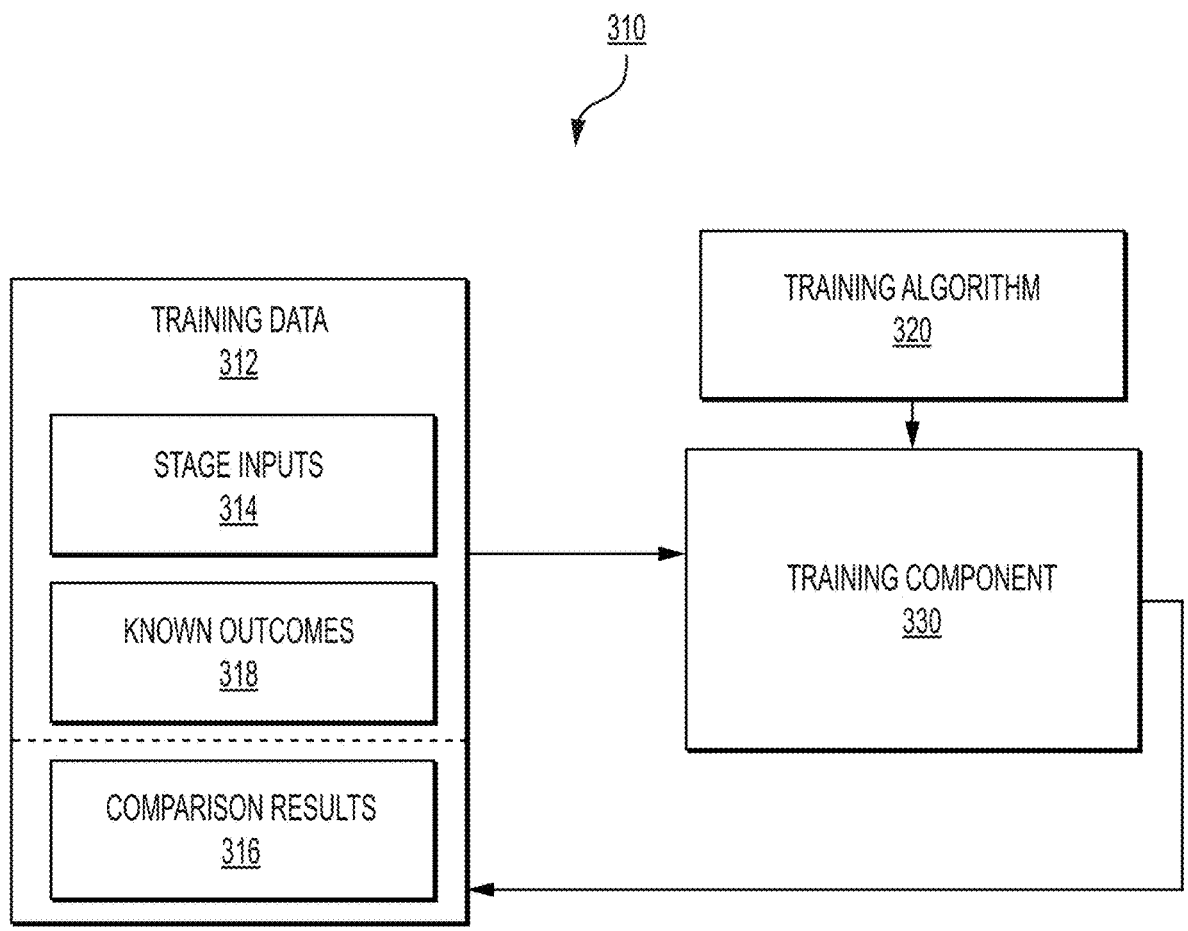
FIG. 3B shows a schematic illustration of training an exemplary machine learning model, in accordance with one or more embodiments.

As further disclosed herein, one or more components of the disclosed subject matter may be implemented using a machine learning model. FIG. 3B shows an example training module 310 to train one or more of the machine learning models disclosed herein. It will be understood that a different training module may be used to train each of the machine learning models disclosed herein and/or a single training module 310 may be used to train two or more machine learning models.

As shown in FIG. 3B, training data 312 may include one or more of stage inputs 314 and known outcomes 318 related to a machine learning model to be trained. The stage inputs 314 may be from any applicable source including a healthcare provider 7, one or more servers 29, electronic devices 19, EMR 14, an output from a step (e.g., one or more outputs from a step from flowchart 500 of FIG. 5 or flowchart 600 of FIG. 6, time in range (TIR) values, time above range (TAR) values, time below range (TBR) values, severity score, continuous glucose monitoring (CGM) classification, GRI values, engagement data, etc.). The known outcomes 318 may be included for machine learning models generated based on supervised or semi-supervised training. An unsupervised machine learning model may not be trained using known outcomes 318. Known outcomes 318 may include known or desired outputs for future inputs similar to or in the same category as stage inputs 314 that do not have corresponding known outputs.

The training data 312 and a training algorithm 320 may be provided to a training component 330 that may apply the training data 312 to the training algorithm 320 to generate a machine learning model. According to an embodiment, the training component 330 may be provided comparison results 316 that compare a previous output of the corresponding machine learning model to apply the previous result to re-train the machine learning model. The comparison result 316 may be used by the training component 330 to update the corresponding machine learning model. The training algorithm 320 may utilize machine learning networks and/or models including, but not limited to a deep learning network such as Deep Neural Networks (DNN), Convolutional Neural Networks (CNN), Fully Convolutional Networks (FCN) and Recurrent Neural Networks (RCN), probabilistic models such as Bayesian Networks and Graphical Models, and/or discriminative models such as Decision Forests and maximum margin methods, or the like.

Health Conditions

Diabetes mellitus (commonly referred to as diabetes) may be a chronic, lifelong metabolic disease (or condition) in which a patient's body is unable to produce any or enough insulin, or is unable to use the insulin it does produce (insulin resistance), leading to elevated levels of glucose in the patient's blood. The three most identifiable types of diagnosed diabetes include: pre-diabetes, type 1 diabetes, and type 2 diabetes. Pre-diabetes is a condition in which blood sugar is high, but not high enough to be type 2 diabetes. Type 2 diabetes is a chronic condition that affects the way the body processes blood sugar. Lastly, type 1 diabetes is a chronic condition in which the pancreas produces little or no insulin.

Diabetes generally is diagnosed in several ways. Diagnosing diabetes may require repeated testing on multiple days to confirm the positive diagnosis of a types of diabetes. Some health parameters that doctors or other suitable healthcare providers use when confirming a diabetes diagnosis include glycated hemoglobin (A1C) levels in the blood, fasting plasma glucose (FPG) levels, oral glucose tolerance tests, and/or random plasma glucose tests. Commonly, a healthcare provider is interested in a patient's A1C level to assist in the diagnosis of diabetes. Glycated hemoglobin is a form of hemoglobin that is measured primarily to identify the three-month average plasma glucose concentration that may be used by doctors and/or other suitable healthcare providers include weight, age, nutritional intake, exercise activity, cholesterol levels, triglyceride levels, obesity, tobacco use, and family history.

Once a diagnosis of a type of diabetes is confirmed by a doctor or other suitable healthcare provider, the patient may undergo treatment to manage their diabetes. Patients having their diabetes tracked or monitored by a doctor or other healthcare provider may be treated by a combination of controlling their blood sugar through diet, exercise, oral medications, and/or insulin treatment. Regular screening for complications is also required for some patients. Depending on how long a patient has been diagnosed with diabetes, mHealth application 1 may suggest a specific treatment plan to manage their condition(s). Oral medications typically include pills taken by mouth to decrease the production of glucose by the liver and make muscle more sensitive to insulin. In other instances, where the diabetes is more severe, additional medication may be required for treating the patient's diabetes, including injections. An injection of basal insulin, also known as background insulin, may be used by healthcare providers to keep glucose levels at consistent levels during periods of fasting. When fasting, the patient's body steadily releases glucose into the blood to supply the cells with energy. An injection of basal insulin is therefore needed to keep glucose levels under control, and to allow the cells to take in glucose for energy. Basal insulin is usually taken once or twice a day depending on the type of insulin. Basal insulin acts over a relatively long period of time and therefore is considered long acting insulin or intermediate insulin. In contrast, a bolus insulin may be used to act quickly. For example, a bolus of insulin that may be specifically taken at meal times to keep glucose levels under control following a meal. In some instances, when a doctor or healthcare provider generates a treatment plan to manage a patient's diabetes, the doctor creates a basal-bolus dose regimen involving, e.g., taking a number of injections throughout the day. A basal-bolus regimen, which may include an injection at each meal, attempts to roughly emulate how a non-diabetic person's body delivers insulin. A basal-bolus regimen may be applicable to people with type 1 and type 2 diabetes. In addition to the basal-bolus regimen requiring injections of insulin, the treatment plan may be augmented with the use of prescribed oral medications. A patient's adherence to a treatment plan may be important in managing the disease state of the patient. In instances where the patient has been diagnosed with diabetes for more than six months, for example, a very specific treatment regimen must be followed by the patient to achieve healthy, or favorable, levels of glucose. Ultimately, weekly patterns of these medication types of treatments may be important in managing diabetes. mHealth application 1 may recommend treatment plans to help patients manage their diabetes.

Exemplary Methods

Diabetes is a chronic condition that results in a patient unable to keep glucose within a normal or recommended target range. Such fluctuating glucose levels (i.e., outside the normal or recommended target range) can lead to significant health complications. Developing meaningful insights and predictions for health and engagement outcomes is difficult with sporadic blood glucose monitoring (BGM), where only a handful of intermittent readings in a week may not serve a basis to understand patterns, and any underlying causes for those patterns (e.g., determining a rising BGM based on a meal type). A similar issue may exist with respect to flash glucose monitoring (FGM), in that readings are sporadic and non-regular or continuous.

Continuous glucose monitoring (CGM) provides the possibility for dense data (e.g., data based on a collection frequency of every 5 minutes or less) to be automatically gathered through wearable sensors (e.g., sub-cutaneous sensors) that provide a periodic glucose value (e.g., a user 8's glucose levels). CGM can improve diabetes care by providing a continuous (e.g., approximately every five minutes or less) or semi-continuous (e.g., more than approximately every five minutes) readout of glucose data to user 8 or other entities (e.g., healthcare provider 7) so that the user 8 or other entities can be more aware of the user 8's glucose levels at all times of the day. Such data may allow a machine learning model to be trained to predict future health and engagement levels and outcomes based on inputs of glucose levels and engagement data.

A CGM monitor may be a continuous analyte sensor system that includes any sensor configuration that provides an output signal indicative of a concentration of an analyte. The CGM monitor may sense the concentration of the analyte to determine, for example, glucose values, based on a bodily fluid (e.g., interstitial fluid). The bodily fluid may be accessed through a user's skin. The output signal, which may be in the form of, for example, sensor data, such as a raw data stream, filtered data, smoothed data, and/or otherwise transformed sensor data, may be sent to a receiver, which may be connected to the CGM monitor via a wired or wireless connection and may be local or remote from the sensor. According to embodiments, the CGM monitor may include a transcutaneous glucose sensor, a subcutaneous glucose sensor, a continuous refillable subcutaneous glucose sensor, a continuous intravascular glucose sensor, or the like. The CGM monitor may be a compact medical system with one or more sensors that is inserted onto a user 8's abdomen and that includes a small cannula that penetrates the user 8's skin. An adhesive patch may hold the monitor in place. The sensor may sense glucose readings in interstitial fluid on a continuous or semi-continuous basis.

A transmitter may be connected to the sensor to allow the CGM monitor to send the glucose readings wirelessly to a monitoring device. The monitoring device may be a CGM monitor specific monitoring device, may be a third party device, an electronic device 19, or any other applicable device. The monitoring device may be a dedicated monitoring device or an electronic device 19 that provides one or more functions in addition to the CGM monitoring. An application or other software may be used to facilitate the analysis and/or display of the glucose readings and associated data via the monitoring device. The monitoring device may be used to analyze and/or view the data associated with the glucose readings. Alternatively, or in addition, the CGM monitor may include a display to view glucose readings and/or associated data. The CGM monitor and/or external device may be configured to generate and/or provide alerts based on the glucose data (e.g., if blood sugar levels are too high or too low, or showing an unfavorable trend).

By using CGM data, a time in range (TIR) value can be determined where a TIR value is based on an amount of time a user 8's glucose level is within a threshold band over a base time period. The threshold band may be pre-determined, be user specific, or may be dynamically determined.

The threshold band may be a pre-determined value based on, for example, a cohort of patients. The lifestyle, habits, medical test results for each of the patients in a cohort may be used to determine the pre-determined value. For example, one or more cohorts of patients may be determined based on the patient's lifestyle, habits, demographics, or the like, and a threshold band may be generated for each of the one or more cohorts. The threshold band may be determined based on optimal results (e.g., preferred A1C values) based on an analysis of glucose levels over a period of time.

A GRI value may be determined using CGM data where a GRI value may be a composite metric from CGM tracings that may be indicative of a quality of glycemia for a user 8 and may assist with basic clinical interpretation of CGM data. A "quality of glycemia" may be characterized by proportions of time with both low/very low, and high/very high glucose concentrations. A GRI value is based on a hypoglycemia component and a hyperglycemia component. The hypoglycemia component may be associated with an amount of time a user 8 was hypoglycemic during a specified time period and the hyperglycemia component may be associated with an amount of time the user 8 was hyperglycemic during the specified time period.

The following equations may be used to determine a GRI value. In the following equations, "VLow" represents a percentage of time a user experiences very low-glucose hypoglycemia and "Low" represents a percentage of time a user experiences low-glucose hypoglycemia. "VHigh" represents a percentage of time a user experiences very high-glucose hyperglycemia and "High" represents a percentage of time a user experiences high-glucose hyperglycemia. "HypoComponent" represents a hypoglycemia component while "HyperComponent" represents a hyperglycemia component.

$$\text{Hypoglycemia Component} = V\text{Low} + (0.8 \times \text{Low})$$

$$\text{Hyperglycemia Component} = V\text{High} + (0.5 \times \text{High})$$

$$\text{GRI} = (3.0 \times \text{HypoComponent}) + (1.6 \times \text{HyperComponent})$$

Another equivalent equation for GRI includes:

$$\text{GRI} = (3.0 \times V\text{Low}) + (2.4 \times \text{Low}) + (1.6 \times V\text{High}) + (0.8 \times \text{High})$$

Figure 4:
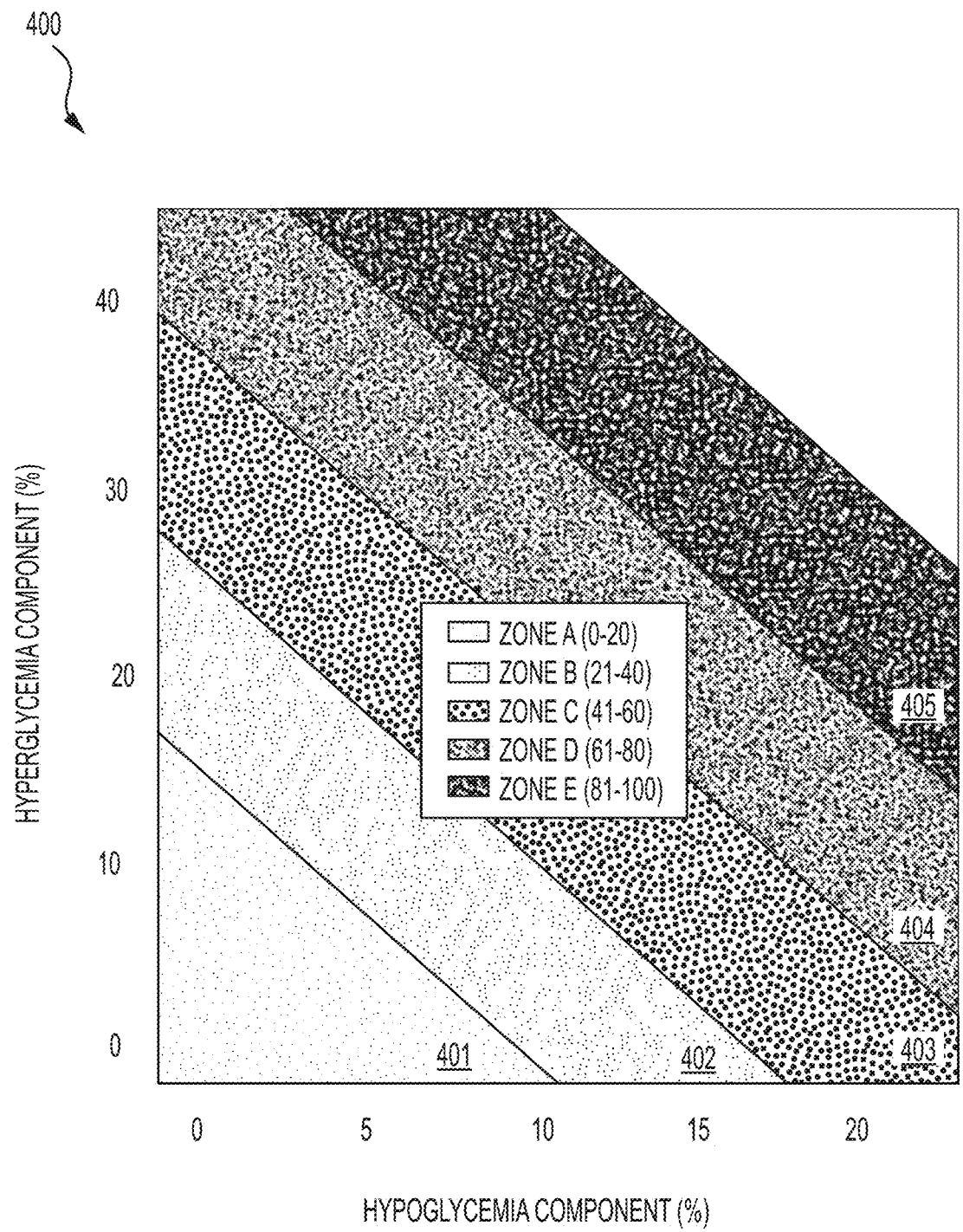
FIG. 4 shows a plot depicting GRI zones, in accordance with one or more embodiments.

FIG. 4 shows a plot 400 depicting five GRI zones, in accordance with one or more embodiments. Because glycemic control is a two-dimensional quality, the GRI's hypoglycemia and hyperglycemia components may be displayed on a two-dimensional plot, as shown in plot 400. In plot 400, the hypoglycemia component is displayed on the horizontal axis and the hyperglycemia component is displayed on the vertical axis. However, it will be understood that the hypoglycemia component and/or hyperglycemia component may be visualized in any applicable manner. A set of diagonal lines divides plot 400 into 5 glycemia risk zones, labeled

401, 402, 403, 404, and 405. Each of these zones corresponds to a quintile for overall quality of glycemia ranging from the best (0-20$^{th}$ percentile, zone A 401) to the worst (81$^{st}$ to 100$^{th}$ percentile, zone E 405). Users with diabetes may receive a GRI score for a given time period and the score may be mapped to one of the five GRI zones. Additional information related to a composite metric for the quality of glycemia from CGM for assisting with basic clinical interpretation of CGM data is provided in Klonoff et al (Klonoff D C, Wang J, Rodbard D et al. A glycemia risk index (GRI) of hypoglycemia and hyperglycemia for continuous glucose monitoring validated by clinician ratings. J Diabetes Sci Technol. 2022 Mar. 29), which is incorporated herein by reference.

Figure 5:
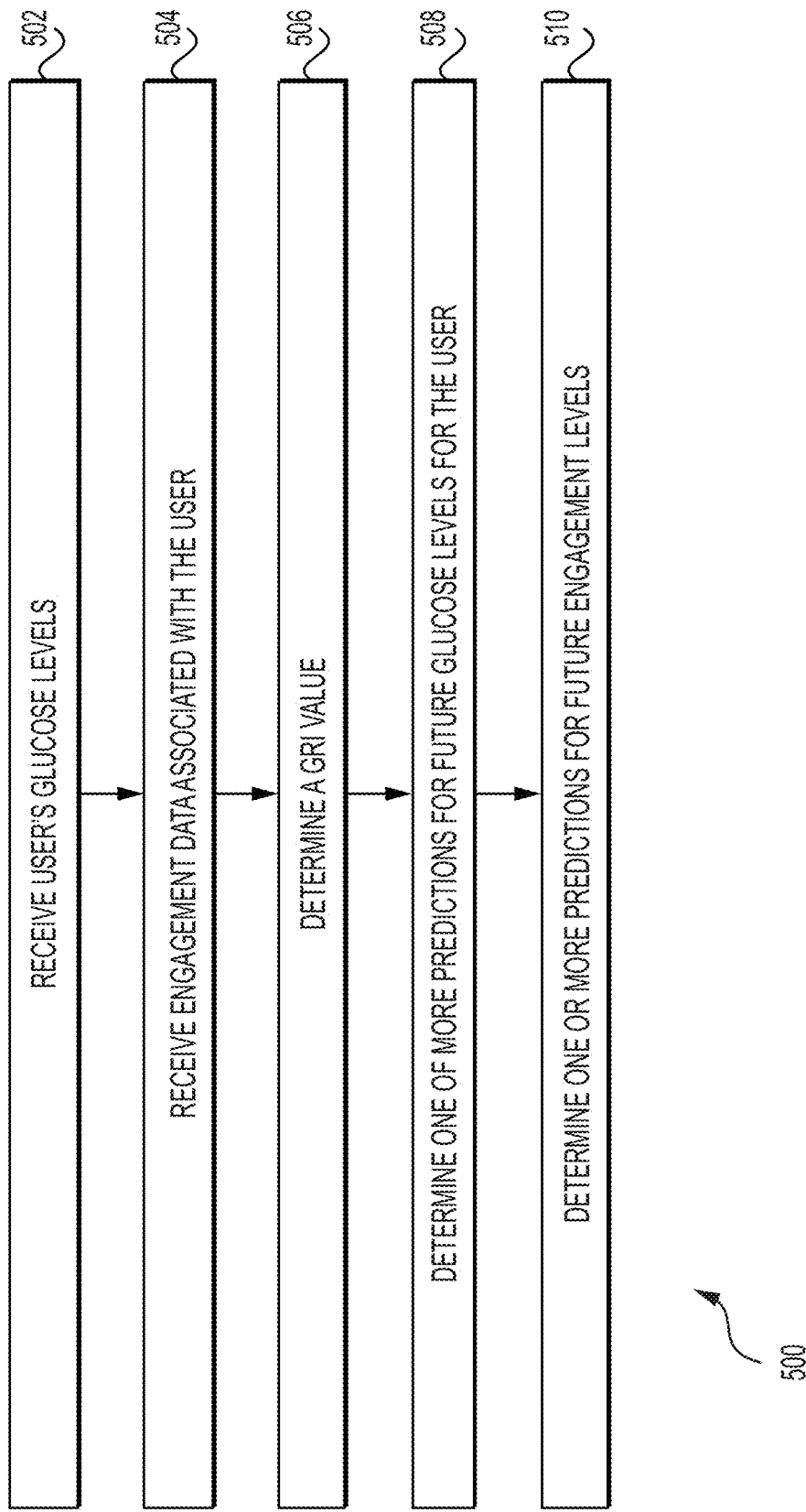
FIG. 5 shows a flowchart for determining one or more predictions for future glucose and engagement levels, in accordance with one or more embodiments.

FIG. 5 shows a flowchart 500 for determining one or more predictions for future glucose and engagement levels, according to one or more embodiments. As used herein, an engagement level may correspond to a level of input or interaction of a user associated with medical, diet, exercise, etc. compliance. At 502, a user 8's blood glucose levels may be received. The blood glucose levels may be provided on a continuous or semi-continuous basis by a CGM monitor, as disclosed herein. The blood glucose levels may also be provided by a standard blood glucose monitor (BGM), by a flash glucose monitor (FGM), or a combination of CGM, BGM, and/or FGM. The blood glucose levels may be received at a component of the CGM monitor itself or may be received at a local or remote component such as an electronic device 19, mHealth application 1, one or more servers 29, or the like. The blood glucose levels may be provided automatically from the CGM monitor to one or more components, may be pushed upon collection of blood glucose levels, or the CGM monitor may be pinged to transmit one or more collected blood glucose levels.

As an example, a user 8 may attach a CGM monitor to her body and the CGM monitor may collect blood glucose level readings approximately every five minutes. The CGM monitor may be connected to the user 8's mobile device (e.g., via a network connection, local area network connection, wide area network connection, WiFi connection, Bluetooth® connection, etc.). According to a first example embodiment, the CGM monitor may automatically transmit a blood glucose level reading to user 8's mobile device each time a reading is collected (e.g., every 5 minutes). Alternatively, or in addition, the CGM monitor may store one or more blood glucose level readings such that they are sent to the user 8's mobile device as a group of multiple readings and/or when the user 8's mobile device or another component requests that the one or more blood glucose level readings are transmitted.

At 504 of FIG. 5, engagement data associated with the user may be received. The engagement data may be collected over a predefined period time (e.g., the same time period for glucose levels collection at step 502) by a computing device, such as electronic device 19. The engagement data may include and/or be associated with user 8's medication intake, diet, physical activity, laboratory results, and/or education activity (e.g., "MEDAL" activities), which are each discussed herein in more detail. The engagement data may also include CGM engagement associated with user 8. CGM engagement may include blood glucose activity which may be collected using a CGM device.

In some cases, engagement data may be collected via user input through an application such as mHealth application 1. For example, user 8 may record, using mHealth application 1, each time any medication is taken by user 8. User 8 may record the time and date of the medication intake as well as the medication name, type, and/or dosage. User 8 may also record a medical intake technique such as whether the medication was taken orally or via some other method of intake (e.g., by injection, inhalation, topical application, etc.). User 8 may record reasons for taking the medication, such as to treat pain or other symptoms. User 8 may further record whether the medication alleviated any of the symptoms, and may further record any side effects that may be experienced from taking the particular medication.

As another example, user 8 may receive a prompt via mHealth application 1 to take a particular medication at a particular time. mHealth application 1 may send a push notification at a prescribed time of medication to remind the user to take the medication. In some cases, mHealth application 1 may prompt user 8 ahead of time (e.g., one hour in advance) to remind user 8 to take a particular medication at a particular time. Following the prompt (e.g., the push notification) to take a medication, mHealth application 1 may follow up requesting input from user 8 that the medication was actually taken. This may be done through a user interface on electronic device 19 via mHealth application 1 that asks for a confirmation of medication intake. In some instances, there may be no prescribed time to take a particular medication and user 8 may not receive a prompt to take a particular mediation. In these instances, user 8 may access mHealth application 1 to enter details about medication intake on a regular basis (e.g., once a week, once a day, multiple times a day).

Medication intake may, in some embodiments, refer to insulin delivery. As discussed herein, insulin delivery may refer to an injection of basal insulin or a bolus of insulin to help the user's body regulate blood sugar levels (i.e., glucose levels). In some cases, user 8 manually performs insulin delivery using a syringe, an insulin pen, an insulin pump, or an insulin inhaler. User 8 may manually calculate and determine when basal and bolus doses are to be administered via any one of these methods. User 8 may also use mHealth application 1 for reminders and calculations regarding the timing and dosage amount of insulin. A combination of manual calculations and automatic reminders and calculations may be employed. For example, a user may receive automatic regular (e.g., hourly) basal doses of insulin via an insulin pump but may need to manually calculate the amount of bolus insulin to administer (often via the same insulin pump) at mealtimes. CGM may be used along with an insulin pump to act as an "artificial pancreas" where a CGM device monitors the blood glucose levels and the basal or bolus dose is determined based on current and predicted glucose levels. As the CGM device and insulin pump work together to administer insulin to user 8, a record of the time, dosage amount, glucose level, and type of insulin for each dose may be stored for future analysis by user 8 or user 8's physician.

Other devices and sensor may be used to measure and record user 8's medication intake. For example, user 8 may place a quantity of pills in a pillbox or pill dispenser, which may be connected to electronic device 19 and/or network 32. The pill dispenser may include one or more sensors to automatically monitor whether the pills (e.g., pills for a particular day) have been removed from the pill dispenser, which may indicate that the medication was taken by user 8. For example, the pill dispenser may include a weight sensor that can sense minute differences in weight and may determine whether a pill is still in the compartment or has been retrieved. The pill dispenser may also include a light sensor that may be blocked by one or more pills, indicating that the pills are still present. There may also be a light that is regularly illuminated and if a full amount of light is received by the light sensor, the pill dispenser may determine that the pills are gone, because one or more pills would block at least some of the light. The light sensor may also determine a color of the pills by measuring the wavelength of any reflected light from the pills. A camera may be used to distinguish shapes and colors of pills which may determine which pills are present and which have been taken. The pill dispenser may also include an automatic dispenser that is programmed to dispense a pill whenever user 8 is supposed to take it. The pill dispenser may keep track of when pills are to be dispensed and may automatically dispense them for user 8. The pill dispenser may keep records of when pills are taken and may transmit these records to electronic device 19 for analysis.

Diet for user 8 may be tracked with user input via mHealth application 1. User 8 may input food eaten during and between meals into mHealth application 1. In some cases, user 8 calculates some or all nutritional information including number of calories, fat content, sugar content, etc. In other cases, mHealth application 1 estimates nutritional information based on a database of foods that includes nutritional information. mHealth application 1 may prompt user 8 at specified times during the day with reminders to record diet information. In one or more embodiments, mHealth application 1 may interact with a CGM device to determine that user 8 has eaten. If glucose levels rise above a threshold or rise at a rate that is above a threshold rate, mHealth application 1 and/or the CGM device may determine that user 8 has eaten. Based on this rise in glucose levels, mHealth application 1 may provide a prompt to user 8 to record diet information. In one or more embodiments, a user may take and provide a photograph of any food before it is eaten as an input for mHealth application 1.

According to an embodiment, mHealth application 1 may use food intake machine learning to determine what the food is and its nutritional details. The food intake machine learning model may be trained using historical or simulated food items and their respective nutritional details. Based on the training, the food intake machine learning model may generate nutritional details based on food intake information such as type of food, type of preparation, ingredients, quantities, and/or the like.

As with medication intake or diet, physical activity may be recorded manually by user 8 via mHealth application 1. Following any kind of physical activity (e.g., workout or exercise), user 8 may record the activity, including the type of activity, the intensity of the activity, feelings and mood before, during, and after the activity, and/or any other notes including unexpected difficulties. User 8 may also record details of the workout related to the particular physical activity. For example, if the activity was a run, user 8 may record the distance covered, time running, percentage of walking during the run, etc.

Physical activity may be collected and recorded automatically via one or more activity trackers (e.g. a smart watch, a smart ring, an activity band, a smart phone, etc.) that utilize one or more sensors to measure one or more metrics related to physical activity. For example, an activity tracker may track a user's steps, elevation gain/loss, heart rate, temperature, etc. The activity tracker may include one or more electronic sensors including an accelerometer, a gyroscope, an altimeter, a photoplethysmography (PPG) sensor, a pulse oximeter sensor (e.g., SpO2 monitor), a bioimpedance sensor (e.g., one or more electrodes or EKG/ECG sensors), an electrodermal activity sensor, a GPS sensor, a light/optical sensor, a compass, a UV sensor, a magnetometer, a gesture sensor, a temperature sensor, a microphone, and/or a skin conductance sensor. One or more of these sensors may work independently or in combination to detect motion, movement, acceleration, elevation, heart rate and/or other heart activity, blood oxygen level, direction, location, orientation and rotation of the device, etc. Raw electronic data may be obtained from these one or more electronic sensors and may be analyzed and synthesized to obtain useful metrics for determining and analyzing physical activity. For example, data related to motion or acceleration may be used to determine a number of steps, the intensity of the steps (e.g., whether the user was walking, jogging, or sprinting). Data related to elevation may be aggregated to the motion data to obtain inferences such as a number of stairs ascended or descended, or distance and elevation gain during a hike.

Other health-related data may be collected, either through user input or automatically via connected electronic devices including, for example, blood pressure and weight. For example, blood pressure may be a useful metric to provide information regarding a user's cardiovascular system and may be measured using an inflatable blood pressure cuff, either manually or automatically. If using a standard blood pressure cuff with manual reading of blood pressure, user 8 may enter the blood pressure in a user interface associated with mHealth application 1. An electronic blood pressure monitor device may measure blood pressure and transmit the value to the mHealth application 1 for storage and analysis. Other methods of measuring blood pressure may include arterial tonometry and oscillometric blood pressure measurement. Similarly, weight of a user may be measured using a standard (e.g., non-electronic) scale with results manually input by user 8 in mHealth application 1. Weight may also be measured using an electronic scale (a "smart scale") that is connected to electronic devices 19 or network 32. Measured weights may be automatically transmitted to mHealth application 1.

Results from lab test or other medical examinations may be collected via user input in mHealth application 1, or by automatic transmission via network 32 directly from the laboratory where lab tests are conducted or the hospital or clinic where the medical examination is conducted. Lab tests or other medical examinations may include A1C tests, lipid profile tests, kidney function tests (e.g., urine albumin tests), eye examinations, foot examinations, liver function tests, thyroid function tests, C-peptide tests, and/or hemoglobin tests.

Education activity may include any activities that a user completes to learn about their condition, management of the condition, and how to prevent or manage complications. By way of example, education activity related to diabetes may take many forms including one-on-one counseling with a healthcare provider or diabetes instructor, group classes or support groups, online resources and apps, and written or audio/visual materials. Diabetes education may cover a variety of topics including understanding the causes and symptoms of diabetes, how to monitor blood sugar levels and interpret the results, the role of medication and insulin therapy in diabetes management, how to manage diet and nutrition to control blood sugar levels, the importance of physical activity and exercise in diabetes management, strategies for preventing or managing diabetes-related complications, such as nerve damage, kidney disease, and vision problems, and tips for coping with the emotional and psychological challenges of living with diabetes.

Education activities may be facilitated via mHealth application 1. For example, user 8 may engage with mHealth application 1 by opening an article about the role of medication and insulin therapy in diabetes management. Another example may include counseling with a healthcare provider or diabetes instructor via mHealth application 1, which may include a videoconference. Engagements with mHealth application 1 such as opening and reading articles or participating in a videoconference with an instructor or provider may be logged and recorded as a completed education activity. User 8 may also manually input in mHealth application 1 completed education activities not facilitated by mHealth application 1.

Engagement data related to medication intake, diet, physical activity, lab results, and education activity (e.g., "MEDAL" data), as discussed above, may be aggregated and synthesized to generate an engagement score (e.g., engagement state) of user 8 over a predefined time period. Engagement, as discussed herein, refers to engagement with mHealth application 1 by manually inputting data into mHealth application 1, by directly interacting with mHealth application 1, and/or by engaging with one or more entities that transmit data to mHealth application 1 on behalf of a user (e.g., automated engagement). For example, the one or more entities may include a laboratory, a support group, a device, a platform, an activity tracker, a pill dispenser, an online calorie tracker, etc. Engagement data, therefore, refers to any data indicating engagement with mHealth application 1, such as manual user inputs from user 8 in mHealth application 1, automated inputs (e.g., using one or more electronic devices 19), received transmissions from third-party sources that received any interaction with user 8 regarding medication intake, diet, physical activity, lab results, and education activity.

In some embodiments, an engagement state may be binary and may be classified as either a high engagement state or a low engagement state. An engagement state may be classified as a high engagement state if user 8 engages with mHealth application 1 or an entity that transmits data to mHealth application 1 at or above a threshold amount. An engagement state may be classified as a low engagement state if user 8 engages with mHealth application 1 or an entity that transmits data to mHealth application 1 below the threshold amount. In some embodiments, an engagement state may be determined based on the number of "engagement activities" that user 8 participates in over a period of time. An engagement activity may be a single activity or interaction with application 1 or an entity that transmits data to mHealth application 1 on behalf of user 8. For example, an engagement activity may include a single user input or entry in mHealth application 1 of a medication taken, a meal and its nutritional information, a workout, lab test results, and/or an education activity. As further examples, an engagement activity may include a transmission received by mHealth application 1 from an activity tracker regarding activity for user 8, from a network-connected pill dispenser, from a third-party lab with lab test results, and/or from a network-connected educational website. According to an embodiment, any time user 8 interacts with mHealth application 1 may be an engagement activity. Any educational activity facilitated via mHealth application 1 or other applicable platform may be recorded as an engagement activity. By way of example of binary engagement states, a threshold for high engagement may be approximately five engagement activities over a period of ten days. Using this example threshold, if user 8 performs approximately five or more engagement activities during a ten day period, then it may be determined that user 8's engagement state is a "high engagement state." If user 8 performs less than approximately five or more engagement activities over the ten day period, then the engagement state may be determined to be a "low engagement state."

There may be more than two engagement states. In one example, there may be three engagement states including a "high engagement state," a "low engagement state," and a "no engagement state." In this example, the high engagement and low engagement states may be the same as for the example above with two engagement states. The difference may be that the no engagement state is registered whenever the number of engagement activities during the time period is zero. There may be a scale of engagement such that instead of a discrete number of engagement states, the number of engagement activities is stored and used for analysis and predictions. Furthermore, in some embodiments, engagement activities may have different weights such that some engagement activities count for a greater level of engagement while others count for a lower level of engagement. The weights of each engagement activity may be accounted for when determining an engagement state.

Engagement data received at 504 may also include a measure of CGM device usage by user 8 ("CGM engagement"). For example, if user 8 continuously uses (e.g., wears) a CGM device day and night, with minimal gaps to switch out a sensor, the received engagement data may indicate a high CGM engagement. In some embodiments, a state of CGM engagement is determined based on a threshold number of CGM readings collected. For example, if user 8's CGM device recorded approximately 70% or more of possible CGM readings during the time period, the CGM engagement state may be classified as a "high engagement state." If user 8's CGM device recorded less than approximately 70% of possible CGM readings during the time period, the CGM engagement state may be classified as a "low engagement state." The number of possible CGM readings in a time period may be approximately 288 readings per day (e.g., one reading approximately every five minutes), and may refer to a frequency at which a CGM device is configured to take a reading of a blood glucose level.

At 506 of FIG. 5, a GRI value may be determined based on hypoglycemia component and a hyperglycemia component according to one or more techniques disclosed herein. The hypoglycemia component may be associated with the amount of time user 8 was hypoglycemic during a time period (e.g., the time period for collecting glucose and engagement levels at steps 502 and 504 respectively). The hyperglycemia component is associated with the amount of time user 8 was hyperglycemic during the same time period. A GRI zone may also be determined based on the GRI value and the hypoglycemia and hyperglycemia components.

In some embodiments, time in range (TIR) values associated with the blood glucose level readings are determined. In-range blood glucose values may correspond to the amount of time blood glucose level readings are within a given range, ratio of blood glucose level readings within range to out of range, count of blood glucose level readings in range to out of range, or the like. For example, TIR values may be based on blood glucose level readings that are between approximately 70 mg/dl and approximately 180 mg/dL. The TIR values may distinguish the user 8's blood glucose levels from the times when they are within the range to the times when they are outside of the range. The determined TIR value may be based on an amount of time user 8's blood glucose level is within a threshold band over a base period of time. The base period of time may be a single 24-hour day or may be a different base period. The base period may be pre-determined (e.g., by user 8, by a healthcare provider 7, pre-programmed, etc.), or may be dynamically determined based on one or more factors. The one or more factors may be patient vectors, patient attributes, a current or previous TIR state, or the like.

According to an embodiment, the TIR value may be for the base period or may be a TIR value associated with the patient over a number of base periods. For example, a TIR value for user 8 may be determined for each day for a total of ten days. The TIR value from each of the ten days may be combined using any applicable technique (e.g., an average) such that the TIR associated with the user 8 over the ten days is the combined TIR value.

At 508 of FIG. 5, one or more predictions for future glucose levels are determined based on user 8's glucose levels and engagement data received at steps 502 and 504. The one or more predictions may be based on user 8's glucose levels and engagement data over a given period of time (e.g., ten days), which may be considered an initial period of time. The one or more predictions may be determined using a machine learning model trained to determine predictions of glucose and/or engagement levels, in accordance with one or more techniques disclosed herein. A prediction may be an estimated or calculated value based on current or historical values (e.g., values determined during the initial period).

Predicted values may include quantitative measurements, such as blood glucose levels, or qualitative metrics derived from the quantitative measurements, such as GRI values. Accordingly, the one or more predictions may include a prediction of one or more future GRI values. A future GRI value may be predicted based on current and historical received and/or determined GRI values. Further, it may be determined whether a future GRI value is greater than or less than the first GRI value determined at step 506. A future GRI zone may also be determined based on the future GRI value. The future GRI zone may be compared to the current determined GRI zone and it may be determined whether the future GRI zone is the same as, or is different from the current determined GRI zone.

In some embodiments, predictions regarding user 8's future glucose levels are based on both the user's current and historical glucose levels and engagement levels. In other embodiments, predictions regarding user 8's future glucose levels are based only on the user's current and historical glucose levels without regard to engagement levels.

The one or more predictions for future glucose levels of step 508 may also include predictions for one or more future TIR values. The predictions may include a prediction of whether a future TIR value is greater than or less than the determined current or historical TIR value responsive to a comparison between the current/historical TIR value and the predicted future TIR value. In some embodiments, the predictions regarding a future TIR value include a prediction of whether the future TIR value is within a certain percentage of the current determined TIR value, or is greater by more or less by more than the certain percentage. For example, it may be predicted that a future TIR value will be within approximately 5% of the current determined or historic TIR value, greater by more than approximately 5%, or less by more than approximately 5%.

At 510 of FIG. 5, one or more predictions for future engagement levels (e.g., future MEDAL levels) are determined based on received engagement levels that were collected over a period of time. According to an embodiment, one or more predictions for future engagement levels may be based on received glucose levels collected over the period of time. The one or more predictions for future engagement levels may be determined using a trained machine learning model trained to take current and/or historical engagement levels and output a prediction for future engagement levels. In some embodiments, the predictions for future engagement levels may be based on current and historical values of glucose levels and engagement levels, or in some cases may be based only on current and historical values of engagement levels, or only on current and historical values of glucose levels. A prediction for future engagement levels may include a prediction of a future engagement state. For example, a predicted future engagement state may be a high engagement state, a low engagement state, no engagement state, an engagement state value or tier, etc. Further, a future predicted engagement state may be compared to the current received or determined engagement state to determine whether the states are different or the same. A prediction for future engagement levels may include predictions for how user 8 may interact and/or engage with mHealth application 1, tracking devices, and/or the like as discussed herein. For example, a machine learning model may receive input engagement data reflecting that user 8 engaged with mHealth application 1 in specific ways (e.g., MEDAL values), and make predictions on how user 8 will engage with mHealth application 1, tracking devices, etc., such as how will user 8 engage with certain foods, certain medications, certain exercise routines, etc.

Future engagement level predictions may also include one or more predictions for future CGM engagement. For example, if user 8's CGM engagement was classified as a high engagement state during the time period of engagement data collection, it may be predicted that user 8 will continue to exhibit high engagement or usage of a CGM device, or additionally based on other factors, that user 8 will in the future exhibit a low engagement state.

One or more sets of features may be derived from the user's glucose levels and/or the engagement data, according to one or more embodiments of the present disclosure. The derived set(s) of features may be provided as inputs to the machine learning model to determine the predictions for future glucose levels and future engagement levels. For example, a machine learning model may be trained to extract derived features based on glucose levels and/or engagement data and/or make feature based predictions based on the derived features.

Figure 6:
FIG. 6 shows a flowchart for training a machine learning model for predicting health and engagement outcomes, in accordance with one or more embodiments.

FIG. 6 shows a flowchart 600 of training a machine learning model for predicting health and engagement levels for a user, according to one or more embodiments. At 602, a first set of glucose levels collected by a CGM device over a first time period are received. In one or more embodiments, two or more first sets of glucose levels is received. For example, a first set of glucose levels may be received for multiple users including user 8. The two or more first sets of glucose levels may also refer to multiple iterations of collecting glucose levels for the same user (e.g., user 8) over multiple fixed time periods. According to an embodiment, the glucose levels received at 602 may be simulated (e.g., using a simulation model configured to output representative glucose levels).

At 604, a second set of glucose levels collected by the CGM device over a second time period are received. The second time period may be subsequent to the first time period and may be the same length of time as the first time period or a different length of time than the first time period. In one or more embodiments, two or more second sets of glucose levels are received, where each set of glucose levels are associated with the same user (e.g., user 8) or, in some cases, a different user. Each first set of glucose levels and each second set of glucose levels corresponding to the same user may be correlated so patterns and relationships between the two may be analyzed and determined.

According to an embodiment, the CGM device used to collect the glucose levels during the first time period and the CGM device used to collect the glucose levels during the second time period may be the same. According to another embodiment, the CGM device used to collect the glucose levels during the first time period and the CGM device used to collect the glucose levels during the second time period may be different. According to this embodiment, differences in CGM devices may be accounted for during training of a machine learning model. For example, the machine learning model may be provided technical information (e.g., drift values, calibration metrics, etc.) associated with each CGM device and may be configured to normalize the CGM values output by each respective CGM device. The first and second set of glucose levels may include the same or substantially similar number of glucose level measurements, but in some cases, the first and second set of glucose levels may include a different amount of glucose level measurements.

At 606, a first set of engagement data is received. In some embodiments, two or more first sets of engagement data are received, where each set is associated with one user (e.g., user 8). Additional sets may be associated with multiple different users or may be engagement data collected multiple times for the same user over multiple fixed time periods. The first set of engagement data is collected by a computing device (e.g., electronic device 19) over the first time period. The first time period over which the first set of engagement data is collected may correspond to the first time period over which the first set of glucose levels were collected (e.g., an initial time period).

At 608, a second set of second engagement data is received. In some embodiments, two or more second sets of engagement data are received, where each set is associated with one user (e.g., user 8). Additional sets may be associated with multiple different users or may be engagement data collected multiple times for the same user over multiple fixed time periods. The second set of engagement data is collected by a computing device (e.g., electronic device 19) over a second time period. The second time period over which the second set of engagement data is collected may correspond to the second time period over which the second set of glucose levels were collected. Both the first and the second sets of engagement data may be associated with one or more of the user's medication intake, diet, physical activity, laboratory results, and education activity (e.g., MEDAL activity).

At 610, one or more machine learning models (e.g., a glucose and engagement machine learning model) is trained based on a machine learning algorithm. A machine learning model may be trained using training data which includes the first glucose levels received at step 602, second glucose levels received at step 604, the first engagement data received at step 606, and second engagement data received at step 608. According to an embodiment, a first machine learning model may be trained specifically for users with type 1 diabetes and a second machine learning model may be trained specifically for users with type 2 diabetes. In some cases, a single machine learning model may be trained for all users with diabetes, regardless of the type.

Sets of features may be derived from the first set of glucose levels received at step 602 and the first engagement data received at step 606. In some cases, features may be derived from the second set of glucose levels received at step 604 and the second engagement data received at step 608. The derived features may be included as a part of the training data or may be determined by the one or more machine learning models based on the input training data from steps 602-608.

According to an embodiment, before being input as training data, the data received at steps 602-608 may be cleaned. Cleaning the data includes identifying and correcting or removing any errors, inconsistencies, or irrelevant information from the dataset. Missing data may be handled by identifying any missing values in the dataset and determining data modifications, including removing a row or column with the missing value, replacing the missing value with an estimate, or using a machine learning algorithm to impute the missing values. Duplicates are removed to avoid skewed results. Data may be standardized if received from multiple different sources, which includes converting the data to a consistent format and/or unit. Outliers (e.g., extreme values that may significantly affect the training) may be modified (e.g., removed or corrected). The data received at steps 602-608 may be examined for human or technical errors and corrected if such errors are identified. Irrelevant data may be removed to target the training on data that is most relevant and important for predicting future health and engagement outcomes.

Relevant features are identified and selected, as discussed herein. According to an embodiment, relevant features may include those that are most important in predicting future health and engagement outcomes (e.g., glucose levels and engagement levels). Irrelevant and/or redundant features may negatively affect the performance of the machine learning model and may increase its complexity, and may be removed. Selecting relevant features may involve exploratory data analysis, correlation analysis, feature importance ranking, and domain knowledge.

Exploratory data analysis may include visualizing the training data and analyzing relationships between different variables, which may be used to identify the features that are highly correlated with the target variable, along with those with a weak relationship. Correlation analysis may involve calculating the correlation coefficient between each feature and the target variable. Features with a high correlation coefficient may be more relevant than those with a low correlation coefficient. Feature importance ranking includes using statistical algorithms such as decision trees or Random Forests to rank the importance of each feature based on their contribution to the accuracy of the model. Domain knowledge may be used to identify relevant features that are not captured by statistical methods. For example, in the present disclosure, it may be known by those in the art that food and medication features are the most relevant for glucose level predictions while comment features (e.g., user input comments in mHealth application 1) and education activity features are not as relevant, and therefore may only add to the complexity of the model, decreasing it usefulness. Once the most relevant features are selected, the training dataset may be transformed to include only those features that are ranked as most important for the model. This reduces the complexity of the model, reduces the risk of overfitting, and improves the overall accuracy of the model in making predictions. In some embodiments, feature selection may be automatic and the most relevant features are selected without manual intervention.

According to an embodiment, any applicable features may be identified such that relevant features are not extracted. Accordingly, such features may include known relevant features as well as features not known to be relevant. The one or more machine learning models may be trained to apply all or a subset of such features based on their applicable weights, layers, biases, synapses, training algorithm and/or the like. According to this embodiment, the one or more machine learning models may be provided or may determine any such applicable features for training or for generating predictive outputs.

According to embodiments disclosed herein, features may be determined based on any applicable attribute such as a category, variance, segment, or the like associated with given data. Such attributes may be based on, but are not limited to, a time or time range (e.g., time of day, hour, day, etc.), type of data (e.g., CGM data, MEDAL data, TIR data, TBR data, GRI data, glucose management indicator (GMI) data, etc.), type of analysis associated with data (e.g., mean, sum, value, etc.), and/or the like.

The model is trained using the training dataset, in accordance with one or more techniques of the present disclosure, including those discussed with respect to FIG. 3B. Training includes using statistical algorithms to find patterns and relationships (e.g., associations, correlations, dependencies, connections, similarities, etc.) in the data that can be used to make predictions. For example, the model is trained with inputs including the first and second sets of glucose levels and the first and second sets of engagement data as discussed in reference to steps 602-608. The model may be trained to, using statistical algorithms, determine patterns and relationships between the first set of glucose levels received at step 602 and the second set of glucose levels received at step 604. Alternatively, or in addition, the model may be trained to determine patterns and relationships between the first set of engagement data received at step 606 and the second set of engagement data received at step 608.

At 612, one or more patterns in the training data are determined. For example, the model may be trained to determine patterns and relationships between the first sets of glucose levels and engagement data and the second sets of glucose levels and engagement data. Determining patterns in the training data may include determining a relationship between the first set of glucose levels received at step 602 and the second set of glucose levels received at step 604. Determining patterns may also include determining a relationship between the first set of engagement data received at step 606 and the second set of engagement data received at step 608. Weights, layers, biases, and/or synapses associated with the machine learning model may be updated based on the determined patterns. Further, testing data may be provided to the machine learning model to determine its accuracy, and the model may be retrained, updated, or tuned based on the results of one or more of the accuracy tests.

In one or more embodiments, as disclosed herein, the machine learning model trained based on the method provided in flowchart 600 may be implemented to make one or more predictions for a new set of unseen data. For example, a third set of glucose levels may be received, where the third set of glucose levels are collected by a CGM device over a third time period that is subsequent to the second time period. A third set of engagement data may also be received, as collected by a computing device over the third time period. Both the third set of glucose levels and the third set of engagement data may be associated with the same user, such as user 8. Using the third set of glucose levels and the third set of engagement data as inputs, the trained machine learning model may be used to determine one or more predictions for future glucose levels or engagement levels (e.g., for a future "fourth" subsequent time period).

Figure 7A:
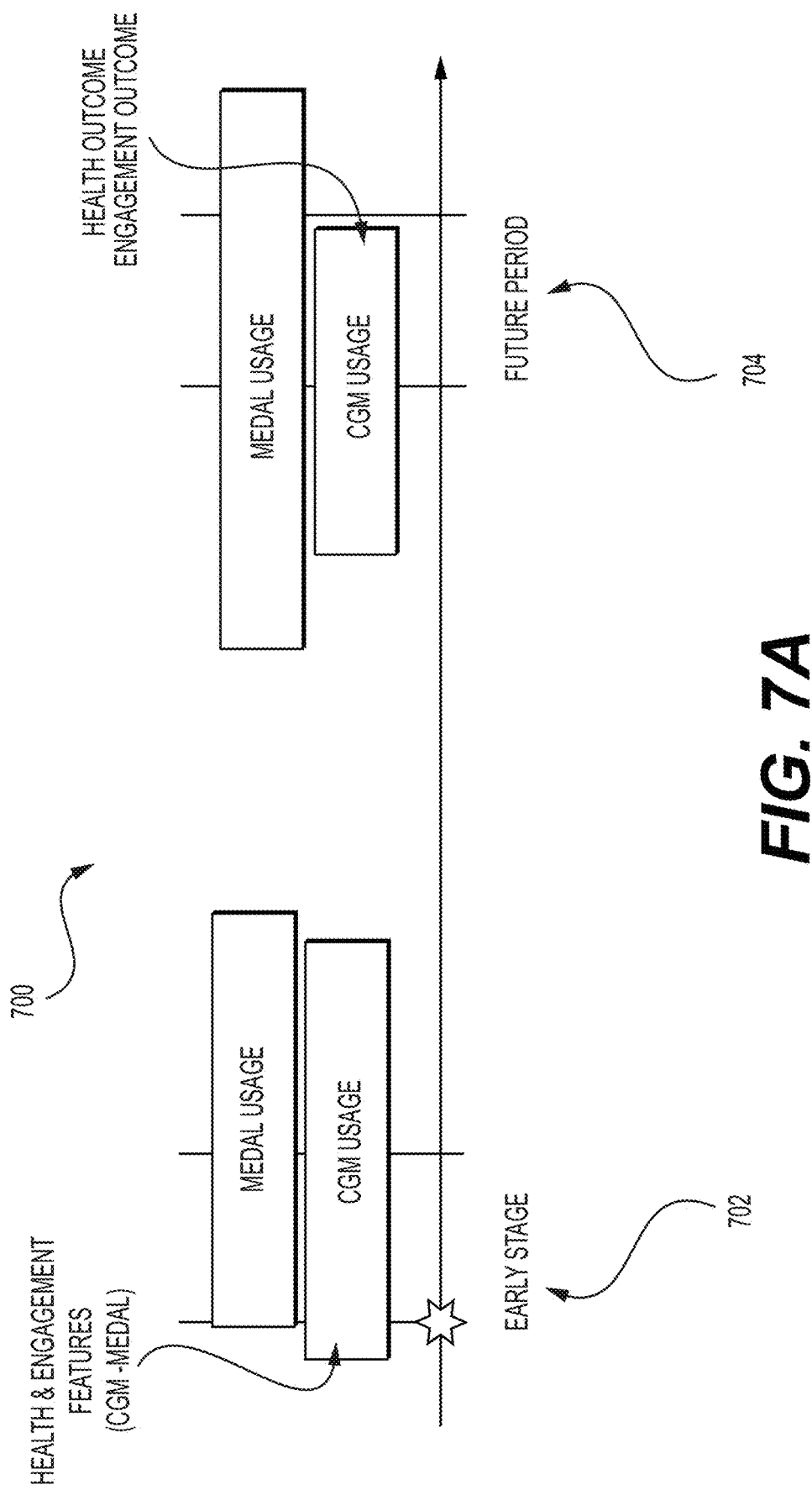

FIG. 7A is a diagram depicting the use of glucose ("CGM usage") and engagement data ("MEDAL usage") to predict future health and engagement outcomes, according to one or more embodiments. Diagram 700 is a timeline with an "early stage" time period 702 (e.g., an initial time period, such as approximately ten days) and a "future period" time period 704. The early stage time period 702 may be a predefined time period where glucose and engagement data is collected to make predictions about glucose and engagement levels during the future period 704. In some embodiments, both the early stage time period 702 and the future period 704 may be the same amount of time, but in some cases they may be different lengths of time. As an example, the early stage time period 702 may range from ten to thirty days and the future period 704 range from approximately five to ninety days. The early stage time period 702 may be directly before the future time period 704, or there may be a gap of time between the early stage time period 702 and the future period 704. There may be a pattern displayed during the early stage time period 702 that is indicative of behavior and outcomes during the future period 704.

FIG. 7B is a table 710 depicting embodiments for future outcome predictions, in accordance with one or more embodiments. Column 712 includes questions about how early stage data may be used to predict different kinds of future health and engagement outcomes. Column 714 includes outcome variables that may be observed to determine respective outcome predictions. Column 716 includes an assigned number for each question asked and the different scenarios that may be output. Column 718 includes a description of different possible outcome predictions for each observed variable. As shown in FIG. 7B, in some embodiments, there may be nine different categories of outcome predictions based on, for example, three different outcome possibilities (e.g., as shown via the questions in column 712). The outcome predictions may be, for example, based on two and three-state direction or value predictions based on a relative difference from a historical input (e.g., based on CGM data, based on compliance data, based on MEDAL data, based on time information, etc.) as compared to a predicted outcome or two state predictions based on value predictions based on a value of a metric (e.g., TIR value, GRI value, MEDAL engagement value, etc.).

According to embodiments of the disclosed subject matter, a generative machine learning model may be trained using historical metabolic values to predict future metabolic values. The generative model may be trained using historical metabolic values for a cohort of individuals. A trained generative model may receive inputs including recent metabolic values for a given individual and may output future biometric values for that given individual. Although CGM values are discussed herein as an example, it will be understood that the techniques disclosed herein may apply to any metabolic values such as, but not limited to, heart rates, heart related values, ketone values, weight values, cortisol values, hormone levels, body electrical values, repertory values, and/or the like.

A generative machine learning model, as applied herein, may be a model that predicts a subsequent value in a sequence of values based on assigning a probability to a sequence of values. Unlike conventional generative machine learning models that predict the next word in a sequence of words, the generative machine learning models discussed herein are trained to output a metabolic value in a sequence of metabolic values. For example, a trained generative model in accordance with the techniques disclosed herein may receive historical and current CGM values for a given individual over a period of time (e.g., over a past day). Such historical and current CGM values may be used to predict future CGM values for a given period of time (e.g., at a specified frequency (e.g., every 5 minutes)) for the next 30 minutes to two hours).

The generative machine learning models discussed herein may be trained to learn the distribution of historical metabolic values (e.g., CGM values). Such a generative machine learning model may be a statistical model of the joint probability distribution on a given observable variable (e.g., historical CGM values) and a target variable (e.g., future CGM values). The generative machine learning models may be used to generate random instances of such observable variables and may select a given observable variable from the random instances that corresponds to a highest probability of occurring (e.g., the most likely future CGM value). Alternatively, or in addition, the generative machine learning model may determine a conditional probability of a target metabolic value based on historical metabolic values. The generative machine learning model may learn patterns and structure of training data that includes historical metabolic values to generate new data that has similar characteristic.

Generative machine learning models, as discussed herein, may be one or more of Generative Adversarial Networks (GANs), Variational Autoencoders (VAEs), and/or Autoregressive models. The training process of a GAN based generative machine learning model may implemented by using two separate networks (e.g., a generator network and a discriminative network) that work to classify training data samples as either being associated with a true distribution or a model distribution. For example, during training, when the discriminative network identifies a difference between the two distributions, the generator network may adjust its parameters to account for the difference. The training may result in the generator network being trained to reproduce a true data distribution such that a randomized generated output by the discriminative network is unable to find a difference. A VAE may utilize a framework of probabilistic graphical models to maximize a lower bound on the log likelihood of the historical metabolic values. An autoregressive model may specify that the output future metabolic values depend linearly on historical metabolic values and on a stochastic term (an imperfectly predictable term). Accordingly, the model may apply a stochastic difference or recurrence relationship.

Large language models (LLMs) are a type of generative AI that can accept image and text inputs to produce text outputs. They have shown promise in various aspects of medical care. LLMs are built using natural language processing (NLP) techniques and trained on large quantities of unlabeled text using self-supervised learning or semi-supervised learning. They are designed to recognize and understand the structure and meaning of human language, classify texts according to their content or purpose, and generate responses that are appropriate and coherent. General-purpose LLMs have shown significant potential in various applications across industries. The proliferation of clinical knowledge encoded and fine-tuned into LLMs, including ClinicalBERT, Med-PaLM2, GatorTron, MedGPT, and Huatuo-GPT, have exhibited significant potential in medical NLP and clinical applications.

Generative Pre-trained Transformer (GPT) models are attention based models, contextualizing meaning from each word that is used to predict the next word, or in the instant application, glucose values. LLM is one such implementations of the GPT architecture. The techniques disclosed herein provide another unique implementation of a GPT architecture.

According to embodiments of the disclosed subject matter, a generative machine learning model may be trained using training data that includes metabolic values of a cohort of individual having a first health condition. The trained machine learning model may be provided, as inputs, recent metabolic values associated with a given individual having a second health condition. The generative machine learning model may be trained to output future metabolic values for the given individual. Accordingly, in accordance with techniques disclosed herein, a generative machine learning model may be trained based on historical data associated with a first medical condition and may predict future metabolic values for an individual having a second medical condition.

For example, as further discussed herein, a generative machine learning model may be trained based on historical CGM values for a cohort of individuals having Type 1 diabetes. The generative machine learning model may be trained to predict future CGM values based on the training associated with the historical CGM values. The trained generative machine learning model may receive, as inputs, CGM values for a given individual that has Type 2 diabetes. The trained generative machine learning model may output future CGM values (e.g., up to approximately 30 minutes in the future, up to approximately 60 minutes into the future, up to approximately two hours into the future, up to approximately one day into the future, etc.). As discussed herein based on experimental data, the trained machine learning model may output such future predicted CGM values that meet a higher accuracy threshold in comparison to conventional techniques.

According to embodiments of the disclosed subject matter, a generative machine learning model may be trained using supplementary variables in addition to and/or in place of metabolic inputs. Such additional inputs may include, for example, the MEDAL values discussed herein, TIR values discussed herein, GRI values discussed herein, and/or the like. Such a generative machine learning model trained based on such supplementary variables may be provided data related to such supplementary variables for a given individual during an inference (e.g., production) stage. The trained generative machine learning model may output future CGM values based on, for example, historical CGM data as well as the supplementary variables.

According to embodiments of the disclosed subject matter, a generative machine learning model trained based on such supplementary variables may be provided a supplementary condition. A supplementary condition may be an input to the generative machine learning model based on, for example, a MEDAL characteristic. For example, the supplementary condition may be an anticipated dosage and/or time for taking a given medication, may be an anticipated or example exercise, may be an anticipated or example food to be consumed by a given individual, and/or the like. The trained generative machine learning model may generate an output that includes future CGM values based on such supplementary conditions. Such a trained generative machine learning model may be trained to adjust future CGM predictions based on such supplementary conditions to account for the effect of such supplementary conditions. Accordingly, a generative machine learning model trained based on supplementary variables may be trained to predict metabolic variables based on input supplementary conditions.

According to embodiments of the disclosed subject matter, a generative machine learning model trained based on supplementary variables may be trained to output supplementary recommendations to meet a metabolic value goal. For example, a generative machine learning model trained based on supplementary variables may be provided a target CGM value goal or range. The trained machine learning model may predict future CGM values based on historical CGM values and/or supplementary conditions. The trained machine learning model may further output recommendations for causing the predicted future CGM values to comply with the CGM value goal or range. For example, the trained machine learning value may output a supplementary condition that would cause the future CGM values to adjust to meet the CGM value goal or range. Such supplementary conditions may include the MEDAL conditions such as a recommended medication or dosage, a recommended exercise, a recommended food item and/or amount, and/or the like.

Figure 8:
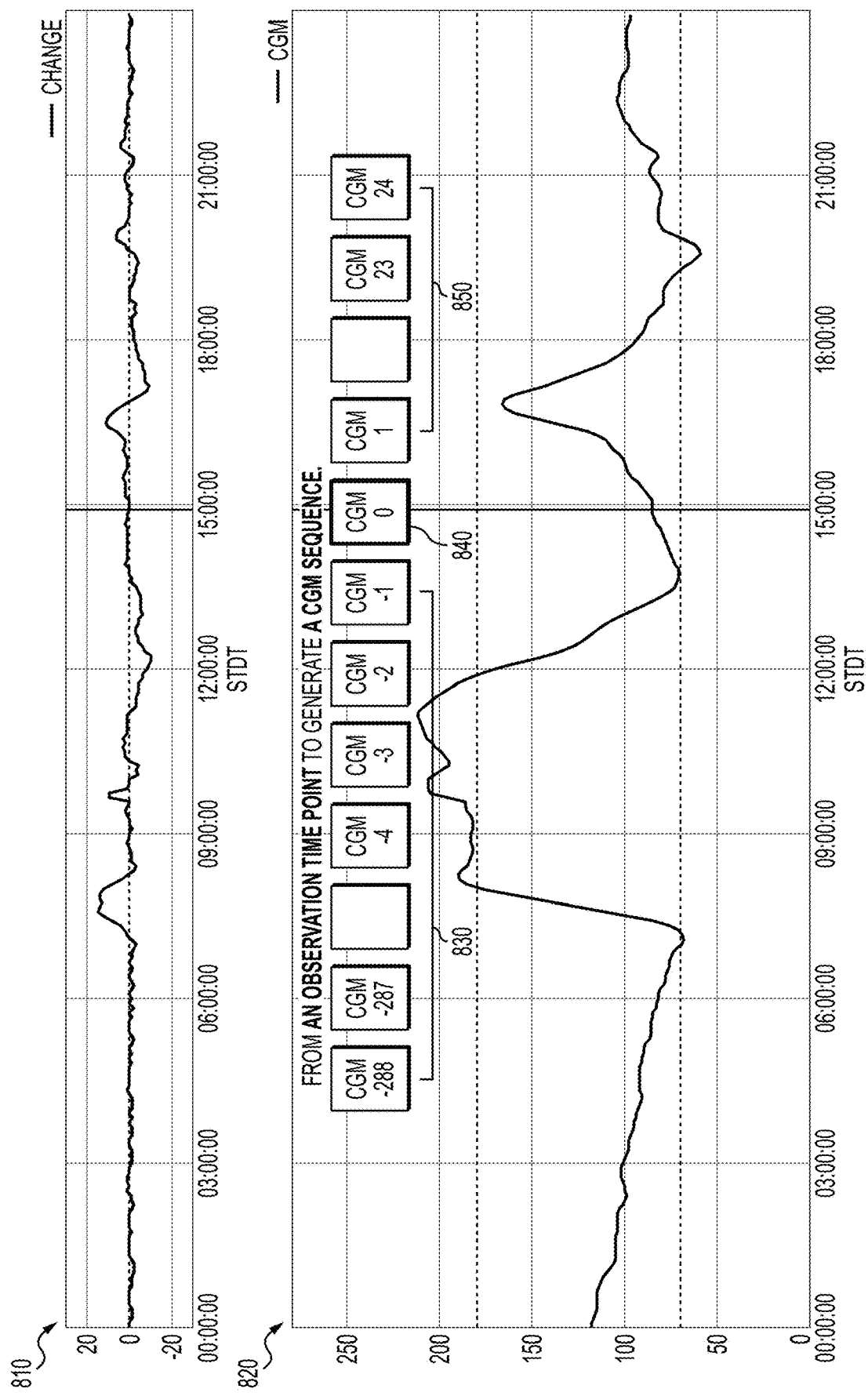
FIG. 8 show example plot of a CGM sequence relating to an observation time point, in accordance with one or more embodiments.

FIG. 8 show example plots of a CGM sequence relating to an observation time point, in accordance with one or more embodiments. Plot 810 depicts a CGM trace with respect to change over time corresponding to plot 820. Plot 820 depicts a CGM trace with respect to the CGM value over time. Plot 820 presents a sequence of CGM values (e.g., CGM −288 through CGM 24). Each CGM value (e.g., CGM 0) represents a data point related to glucose information taken from a user device (e.g. a CGM device output). Each CGM value is taken at a predefined interval (e.g., 5 minutes) totaling 24-hours (e.g., CGM −288 through CGM 0). Plot 820 may include values 830, value 840, and values 850. Values 830 correspond to historical CGM values (e.g., CGM −288 to CGM −1). Value 840 corresponds to a current CGM value (e.g., CGM 0). Values 850 correspond to predicted CGM values (e.g., CGM 1 to CGM 24) output by a generative machine learning model, as discussed herein. Plot 820 highlights CGM 0 at time 15:00:00, identifying the current glucose data taken. As explained in further detail below, the CGM model can predict future CGM values (e.g., up to approximately 2-hours) after the current CGM value (CGM 0). One or more embodiments may predict future CGM values at 30 minutes, 60 minutes, and 2-hour intervals.

Plot 810 and plot 820 of FIG. 8 depict a training phase for a generative machine learning model, as discussed herein. The generative machine learning model is trained based on training data that includes CGM −288 to CGM 0. The generative machine learning model predicts the future values CGM 1 to CGM 24 iteratively (e.g., in sequence). For example, CGM 1 is predicted based on CGM −288 to CGM 0. CGM 2 is predicted based on CGM −288 to CGM 1. The predicted CGM 1 to CGM 24 values are compared to known (e.g., tagged) CGM values to perform the training, as further discussed in reference to FIG. 9 below.

Figure 9:
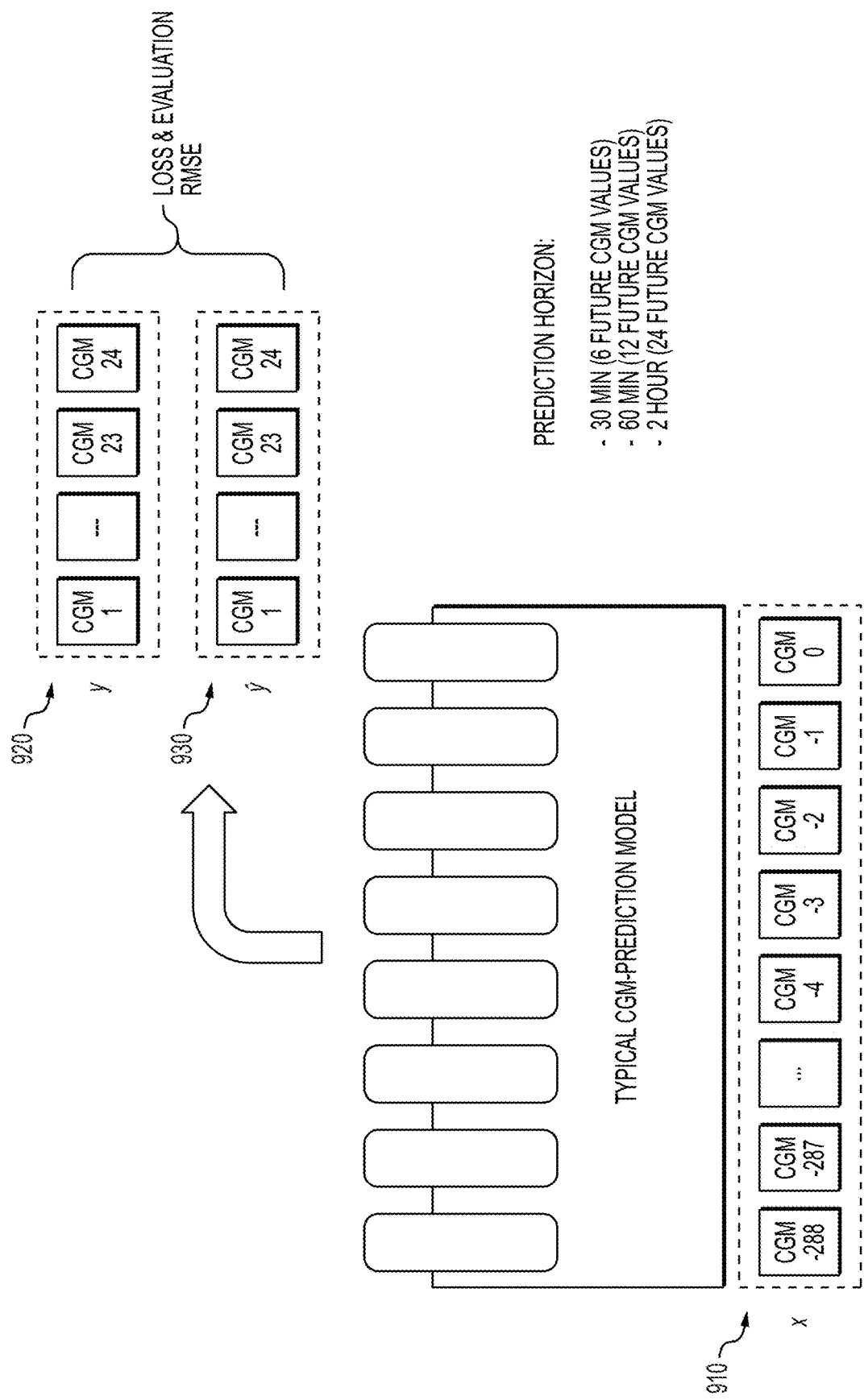
FIG. 9 show diagrams depicting CGM prediction training and inference, in accordance with one or more embodiments.

FIG. 9 show diagrams depicting CGM prediction training, in accordance with one or more embodiments. The CGM prediction model uses CGM values x 910 (e.g., CGM −288 to CGM 0) to generate and predict CGM value ŷ 930. CGM y 920 is the actual known CGM value corresponding to the point in time associated with predicted CGM value ŷ 930. The CGM prediction model may then apply differential logic (e.g., root mean squared error (RMSE)) to identify a difference (e.g., loss) as a mechanism to minimize the difference between the actual CGM value y 920 versus the predicted CGM value ŷ 930 over different time intervals (e.g., 30 minutes, 60 minutes, 2 hours, etc.). According to this example, the CGM prediction model may use 288 previous data points (e.g. 24-hours) to predict upcoming CGM values for the next 2 hours. However, it will be understood that any applicable number of historical metabolic values may be used to predict any applicable number for future metabolic values. The CGM prediction model may use the actual CGM y1 920 to predict CGM ŷ1 930, applying RMSE the CGM prediction model minimizes the loss to predict CGM ŷ2 930. The CGM prediction model evaluates the loss at each CGM value point (e.g., sequence by sequence or CGM point by CGM point) to better predict each future CGM ŷ 930 value.

The process described in FIG. 9 depicts an example training based on the metabolic values for a single individual. As further discussed below, the generative machine learning model may be trained by repeating the process of FIG. 9 across a plurality of individuals. The training using such data for a plurality of individuals may result in the trained generative machine learning models discussed herein. Such trained generative machine learning models may be used at an inference (e.g., production) stage. At such an inference stage, the trained machine learning model may receive recent metabolic values (e.g., CGM values collected over 24-hours) as inputs. The trained machine learning model may output predicted future metabolic values based on the inputs. As further discussed herein, such predicted future metabolic values output by the trained generative machine learning models discussed herein may meet an accuracy threshold greater than those output using conventional techniques.

Figure 10A:
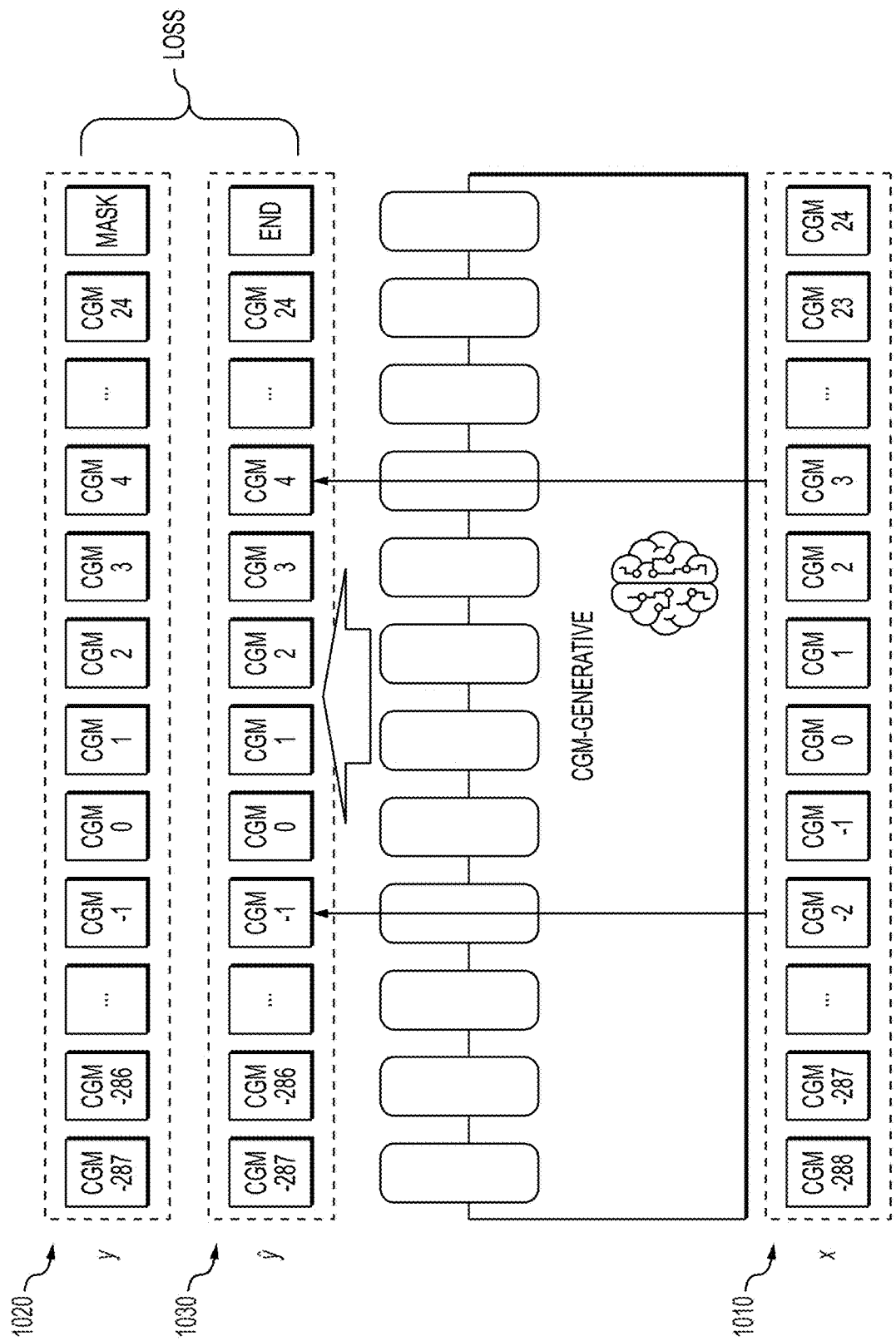
FIGS. 10A-10D show diagrams depicting CGM prediction training inference, in accordance with one or more embodiments.

FIGS. 10A-10D show diagrams depicting CGM prediction training, in accordance with one or more embodiments. FIG. 10A depicts the CGM generative model based next step prediction training. The CGM prediction model may receive, for example, CGM x values 1010 (e.g., 288 CGM values), which may be implemented into the CGM generative model. The CGM generative model may then output and predict the next set of CGM ŷ values 1030. Each future value, CGM y values 1020 and CGM ŷ values 1030, may be used with the previous values to predict the next future CMG value. This is repeated to minimize loss (e.g., decrease error) between predicted CGM values.

Figure 10B:
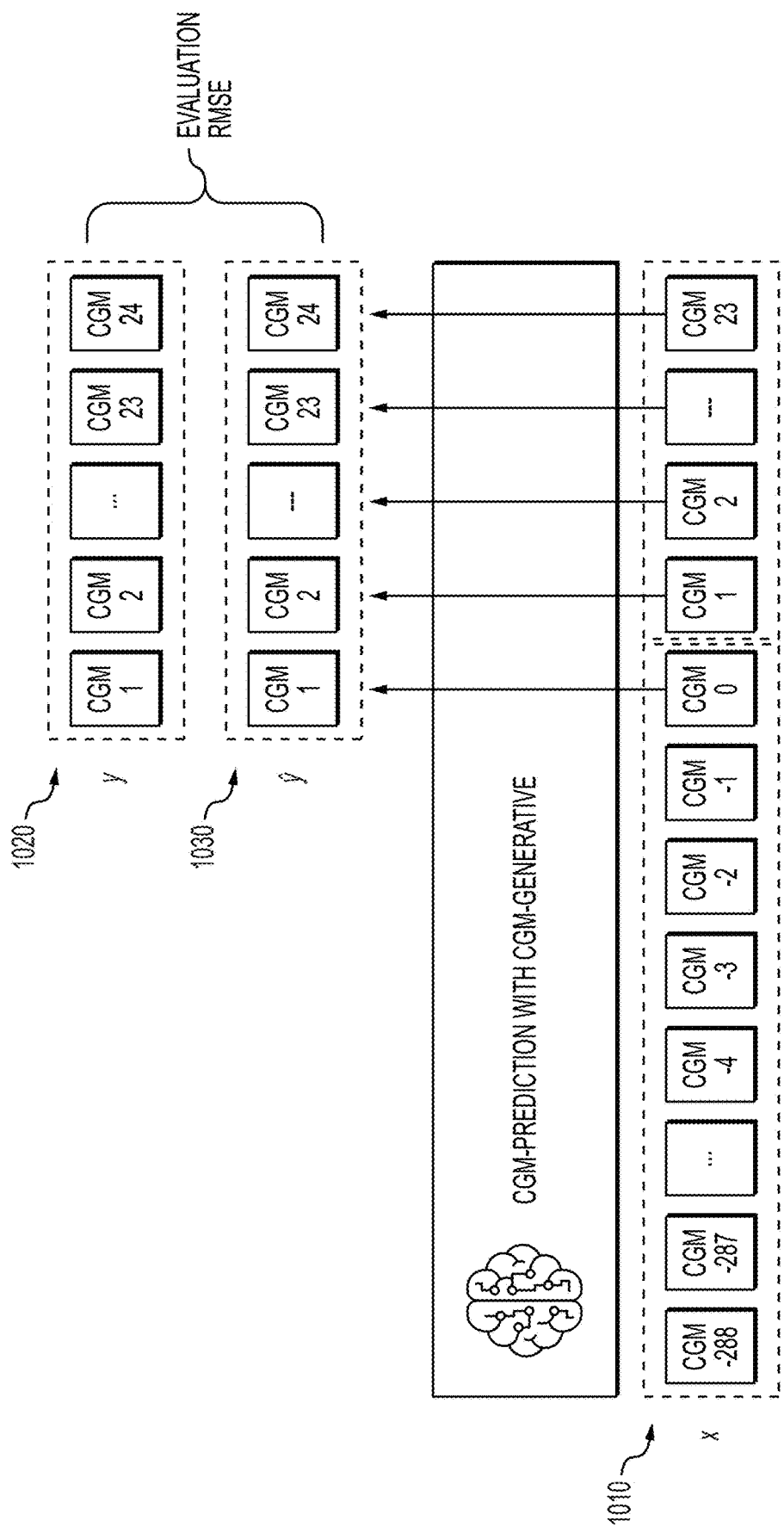

FIG. 10B depicts the CGM GPT prediction inference. Using the CGM GPT prediction (see FIG. 10A), CGM x values 1010 (e.g., 288 CGM values over 24-hours) are fed into the CGM GPT prediction model. The CGM GPT prediction model may start with CGM 0 to predict CGM ŷ1 value 1030. As described above, the model may then calculate, using RMSE, the difference between the predicated CGM ŷ1 value 1030 and the actual CGM y1 value 1020. This information may be fed back into the CGM GPT prediction model to predict CGM ŷ2 value 1030. This calculation and prediction may continue for each CGM ŷ value 1030 (e.g., a progressive RMSE difference is applied to one CGM value at a time to predict the next CGM ŷ).

Figure 10C:
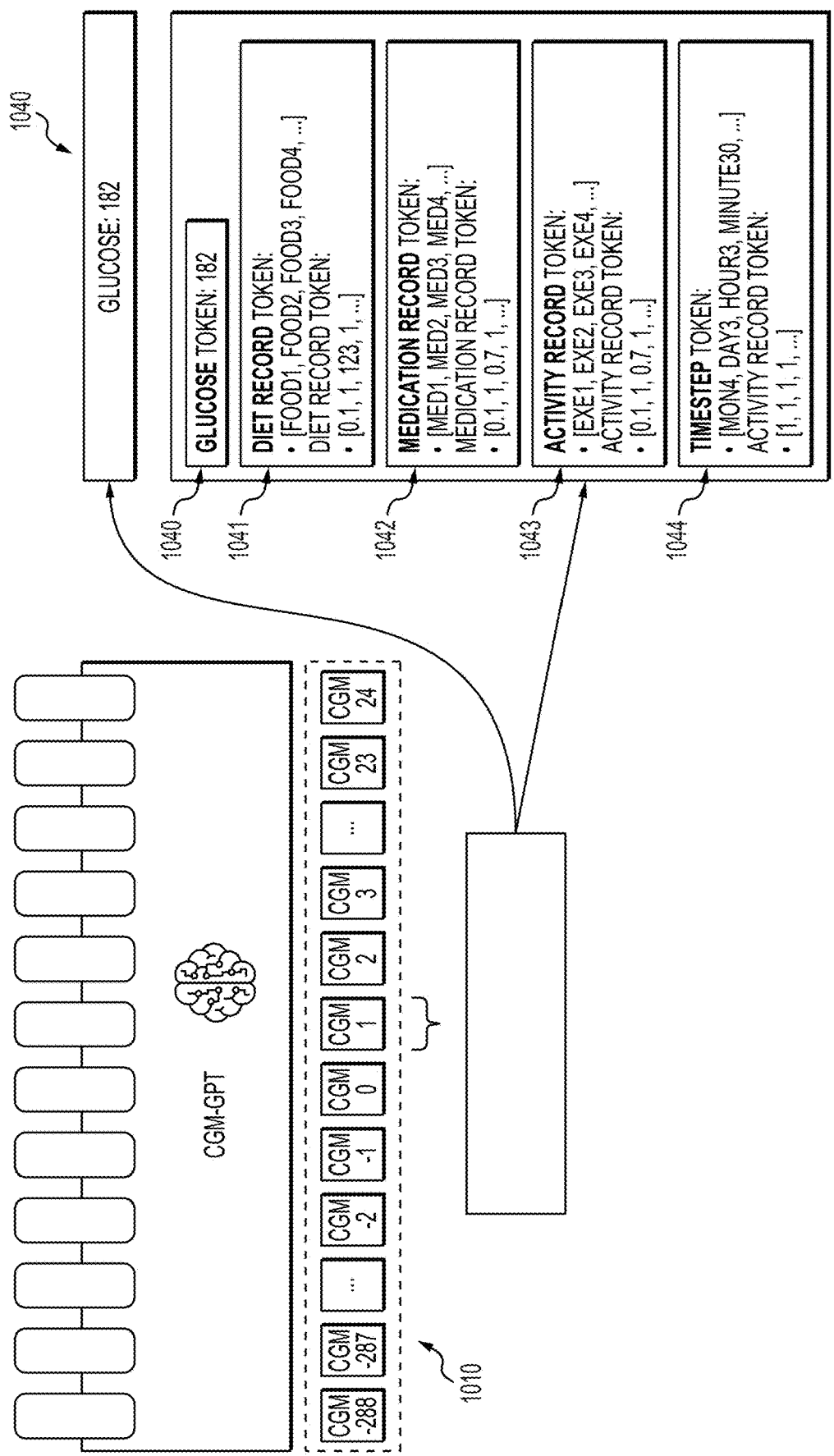

FIG. 10C depicts an example CGM GPT prediction interface. Using the CGM GPT prediction (see FIG. 10A, CGM x values 1010 (e.g., 288 CGM values over 24-hours) are fed into the CGM GPT prediction model as similarly described in FIG. 10B. The CGM GPT prediction model may include a CGM token 1040 (e.g., at least one CGM value). One or more embodiments may include a diet token 1041, a medication token 1042, an activity token 1043, and/or a timestep token 1044. Each token may include additional information (e.g., records) associated with each token to be used within the CMG GPT prediction model. The use of additional tokens (e.g., a diet token 1041, a medication token 1042, an activity token 1043, and/or a timestep token 1044) increases the accuracy of the CGM GPT prediction model.

Figure 10D:
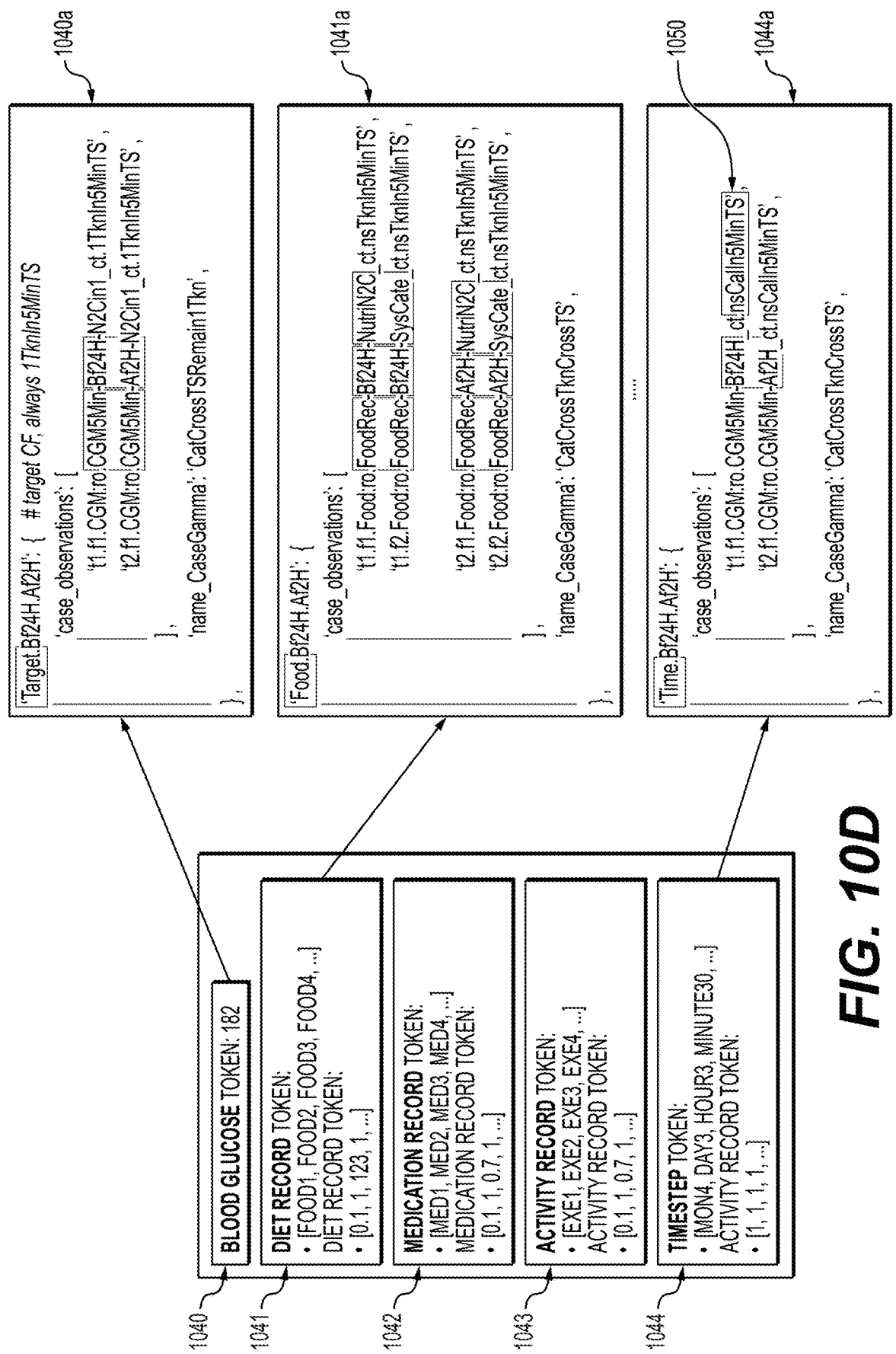

FIG. 10D depicts the CGM prediction model tokens as described in FIG. 10C. A token (e.g., diet token 1041, medication token 1042, activity token 1043, and/or timestep token 1044) may include additional information. For example, CGM token 1040 may include CGM information 1040*a*, diet token 1041 may include food information 1041*a*, and timestep token 1044 may include timestep information 1044*a*. One or more of the additional information items (e.g., CGM information 1040*a*, food information 1041*a*, and/or timestep information 1044*a*) may include a calendar token 1050. Calendar token 1050 may include additional information relating to a calendar associated with a user. The CGM prediction model may have access to the user's calendar information. The use of the user's calendar information may assist in the prediction of future CGM values. The calendar token 1050 may allow for information associated with the predicted CGM values to be imported or exported to one or more applications associated with the user.

Figure 10E:
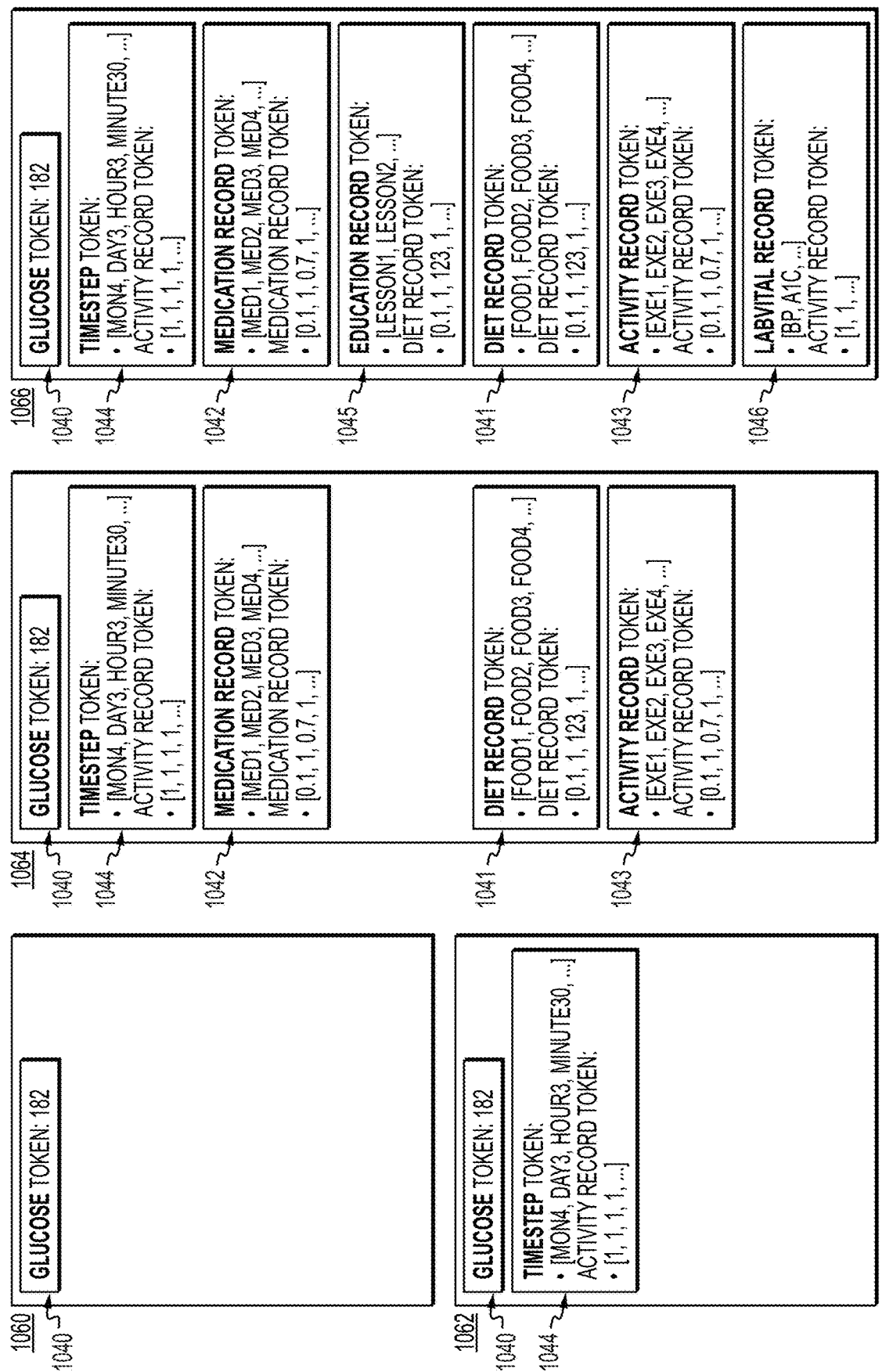
FIG. 10E shows different CGM models using various combinations of tokens, in accordance with one or more embodiments.

FIG. 10E depicts different CGM models using various combinations of tokens. The CGM prediction models may include CGMGPT-Base 1060, CGMGPT-TimeOnly 1062, CGMGPT-MDA 1064, and/or CGMGPT-MEDAL 1066. CGMGPT-Base 1060 may include the use the CGM token 1040. The CGMGPT-TimeOnly 1062 model may include the CGM token 1040 and the Timestep token 1044. The CGMGPT-MDA 1064 model may include the CGM token 1040, Timestep token 1044, Medication token 1042, Diet token 1041, and Activity token 1043. The CGMGPT-MEDAL 1066 model may include the CGM token 1040, Timestep token 1044, Medication token 1042, Education token 1045, Diet token 1041, and Activity token 1043, and LabVital token 1046. Each of the CGM models (e.g., CGMGPT-Base 1060, CGMGPT-TimeOnly 1062, CGMGPT-MDA 1064, and CGMGPT-MEDAL 1066) may be used to predict CGM values.

Figure 10F:
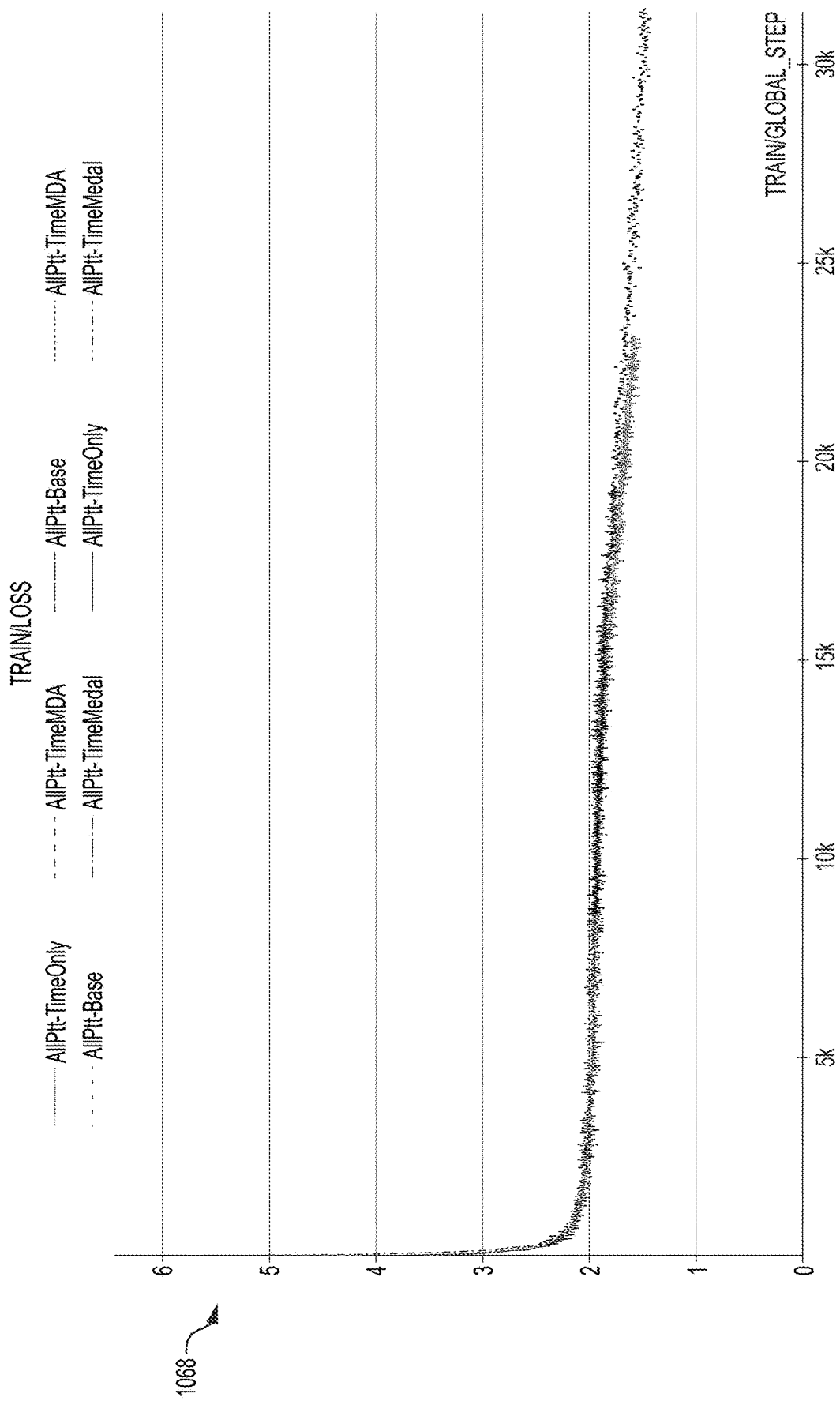
FIGS. 10F-10I shows example CGM prediction outputs for groups of individuals, in accordance with one or more embodiments.

FIGS. 10F-10I shows example plots of a CGM sequence relating to an observation time point, in accordance with one or more embodiments. FIG. 10F depicts plot 1068 including one or more plots for each of the CGM models as described in FIG. 10E.

Figure 10G:
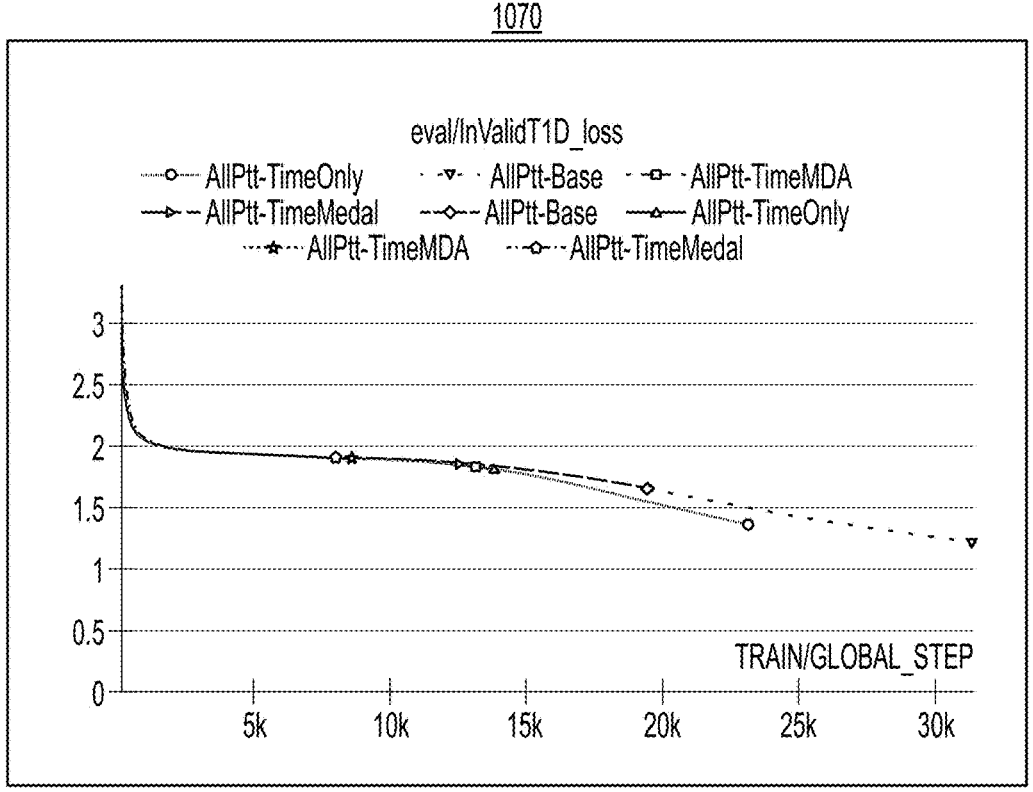
Figure 10G:
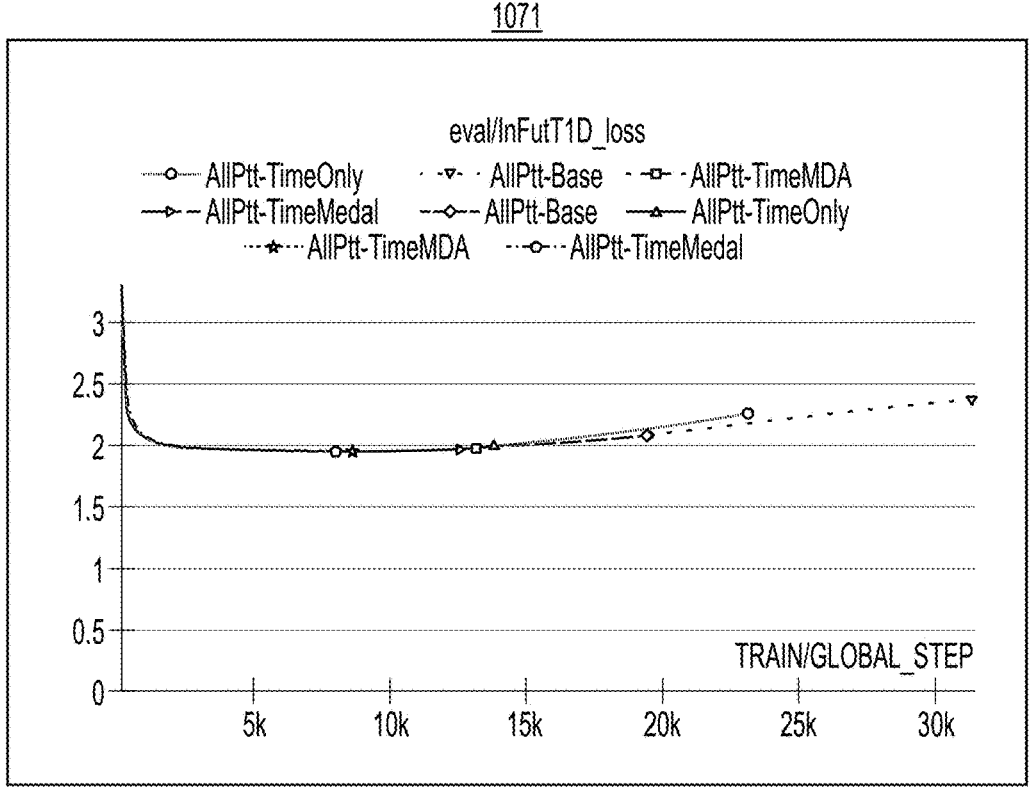

FIG. 10G depicts one or more plots during evaluation of each CGM prediction model, each CGM prediction model being evaluated using patients of type 1 diabetes and a separate set of patients of type 2 diabetes. Plot 1070 depicts a CGM trace for InValid patients having type 1 diabetes, each CGM trace depicted within plot 1070 relates to the CGMGPT model used. Plot 1071 depicts a CGM trace for InFut patients having type 1 diabetes, each CGM trace depicted within plot 1071 relates to the CGMGPT model used. Plot 1072 depicts CGM trace for Out patients having type 1 diabetes, each CGM trace depicted in plot 1072 relates to the CGMGPT model used. Plot 1073 depicts CGM trace for InValid patients having type 2 diabetes, each CGM trace depicted in plot 1073 relates to the CGMGPT model used. Plot 1074 depicts CGM trace for InFut patients having type 2 diabetes, each CGM trace depicted in plot 1074 relates to the CGMGPT model used. Plot 1075 depicts CGM trace for Out patients having type 2 diabetes, each CGM trace depicted in plot 1075 relates to the CGMGPT model used.

Figure 10H:
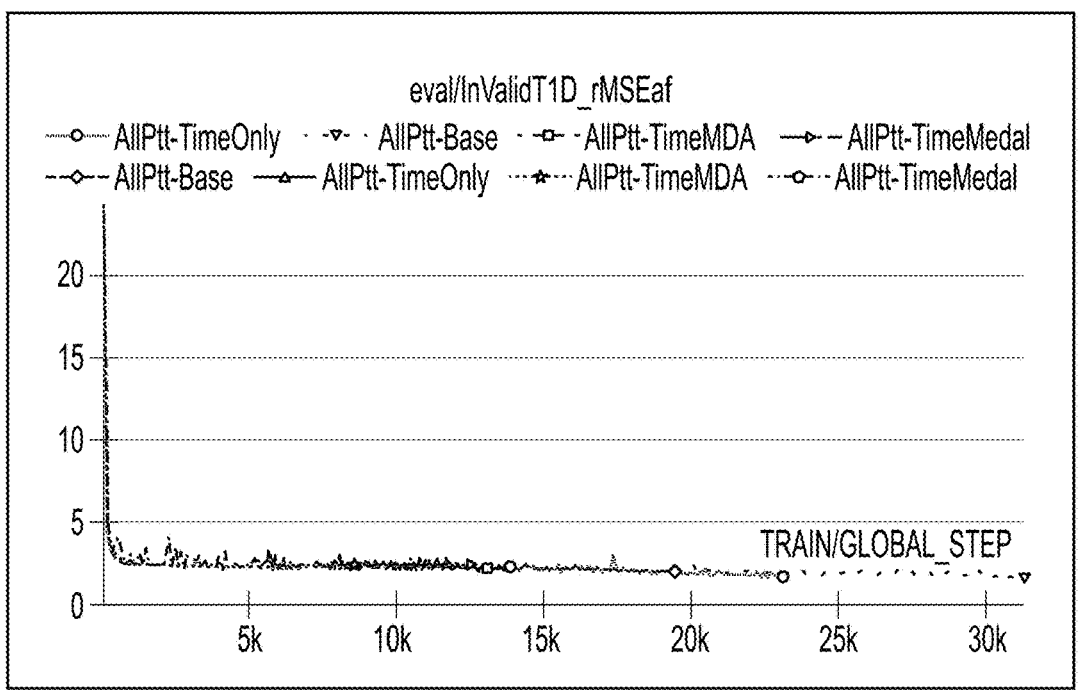
Figure 10H:
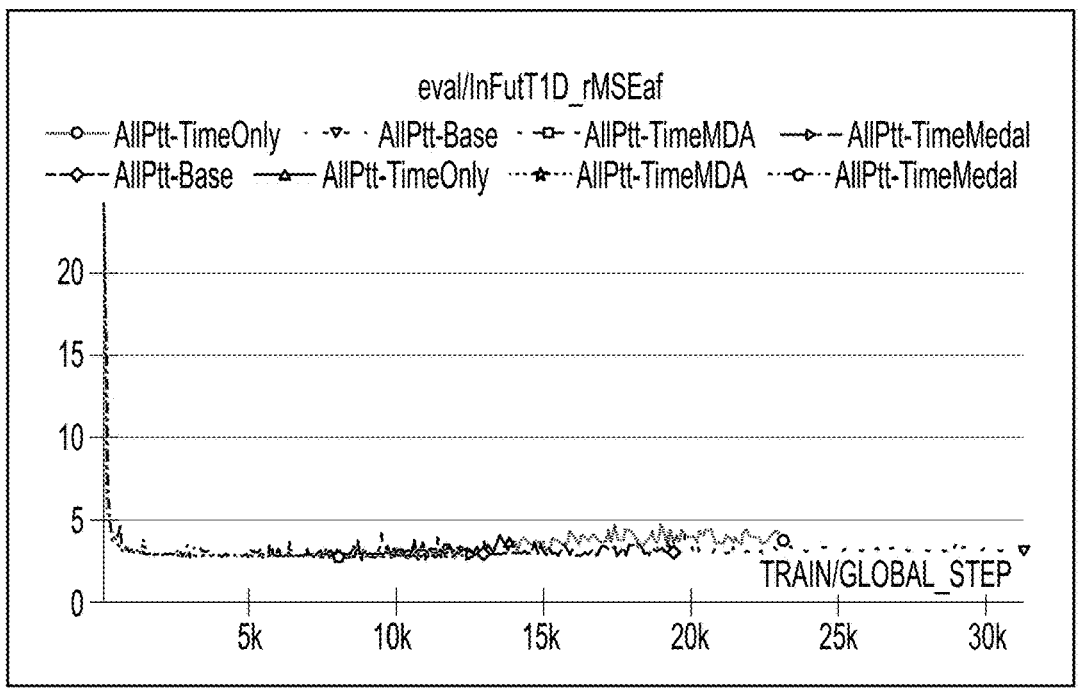

FIG. 10H depicts one or more plots during evaluation of each CGM prediction model using RMSE, each CGM prediction model being evaluated using patients of type 1 diabetes and a separate set of patients of type 2 diabetes. Plot 1080 depicts CGM trace for InValid patients having type 1 diabetes, each CGM trace depicted in plot 1080 relates to the CGMGPT model used. Plot 1081 depicts CGM trace for InFut patients having type 1 diabetes, each CGM trace depicted in plot 1081 relates to the CGMGPT model used. Plot 1082 depicts CGM trace for Out patients having type 1 diabetes, each CGM trace depicted in plot 1082 relates to the CGMGPT model used. Plot 1083 depicts CGM trace for InValid patients having type 2 diabetes, each CGM trace depicted in plot 1083 relates to the CGMGPT model used. Plot 1084 depicts CGM trace for InFut patients having type 2 diabetes, each CGM trace depicted in plot 1084 relates to the CGMGPT model used. Plot 1085 depicts CGM trace for Out patients having type 2 diabetes, each CGM trace depicted in plot 1085 relates to the CGMGPT model used.

Figure 10I:
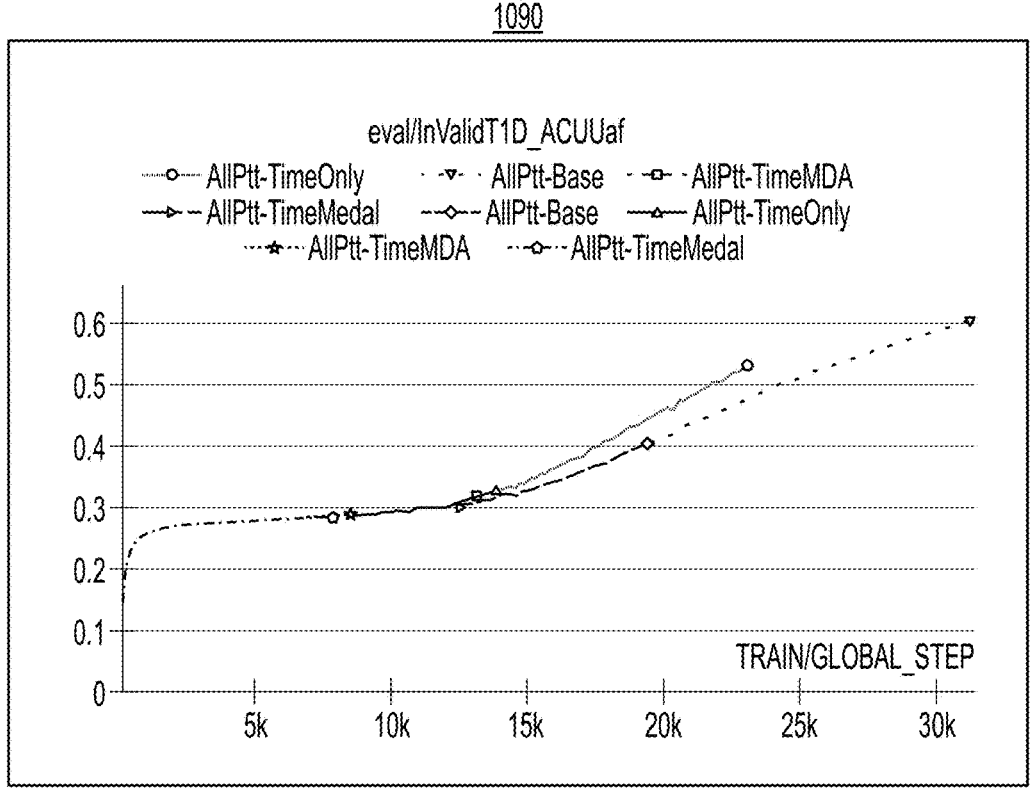
Figure 10I:
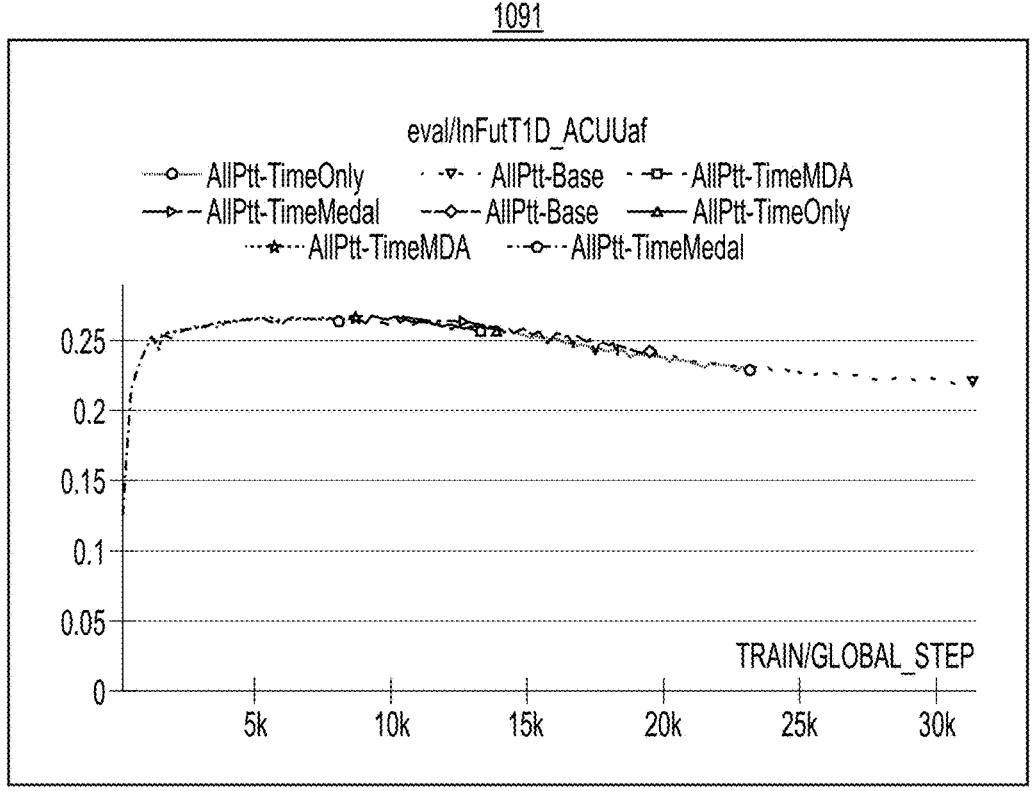

FIG. 10I depicts one or more plots during evaluation of each CGM prediction model, each CGM prediction model being evaluated using patients of type 1 diabetes and a separate set of patients of type 2 diabetes. Plot 1090 depicts CGM trace for InValid patients having type 1 diabetes, each CGM trace depicted in plot 1090 relates to the CGMGPT model used. Plot 1091 depicts CGM trace for InFut patients having type 1 diabetes, each CGM trace depicted in plot 1091 relates to the CGMGPT model used. Plot 1092 depicts CGM trace for Out patients having type 1 diabetes, each CGM trace depicted in plot 1092 relates to the CGMGPT model used. Plot 1093 depicts CGM trace for InValid patients having type 2 diabetes, each CGM trace depicted in plot 1093 relates to the CGMGPT model used. Plot 1094 depicts CGM trace for InFut patients having type 2 diabetes, each CGM trace depicted in plot 1094 relates to the CGMGPT model used. Plot 1095 depicts CGM trace for Out patients having type 2 diabetes, each CGM trace depicted in plot 1095 relates to the CGMGPT model used.

One or more embodiments may include Greedy encoding and/or Multinomial sampling. Greedy coding selects the next word in a sequence strictly based on the highest probability, leading to deterministic and predictable outputs that may lack diversity. Multinomial sampling introduces randomness into the selection process by choosing the next word based on a probability distribution, allowing for more varied and creative outputs but sometimes at the cost of coherence and grammatical correctness. These differences make greedy encoding suitable for applications requiring high accuracy and consistency, while multinomial sampling is better for tasks where creativity and variety are desired.

For example, using numb_beams specifies a number of beams higher than 1, effectively switching from greedy search to beam search. This strategy evaluates several hypotheses at each time step and eventually chooses the hypothesis that has the overall highest probability for the entire sequence. This has the advantage of identifying high-probability sequences that start with a lower probability initial tokens and would have been ignored by the greedy search. Additionally, using do_sample, if set to True, enables decoding strategies such as multinomial sampling, beam-search multinomial sampling, Top-K sampling, and Top-p sampling. One or more of these strategies select the next token from the probability distribution over the entire vocabulary with various strategy-specific adjustments.

Generation task may be performed in different ways and may include a class that holds a configuration for a generation task. A generate call supports the following generation methods for text-decoder, text-to-text, speech-to-text, and vision-to-text models:

greedy decoding by calling_greedy_search( ), if num_beams=1 and do_sample=False constastive search by calling_constrastive_search( ), if penalty_alpha>0, and top_k>1 multinomial sampling by calling_sample( ), if num_beams=1 and do_sample=True beam-search decoding by calling_beam_search( ), if num_ beams>1 and do_sample=False beam-search multinomial sampling by calling_beam sample( ), if num_beams>1 and do_sample=True diverse beam-search decoding by calling_group_beam_search( ), if num_beams>1 and num_beam_group>1 constrained beam-search decoding by calling_constrained_beam_search( ), if constraints!=None or force_words_ids!=None assisted decoding by calling_assisted_decoding( ), if assistant_model or prompt_lookup_num_tokens is passed to .generate( )

Figure 11A:
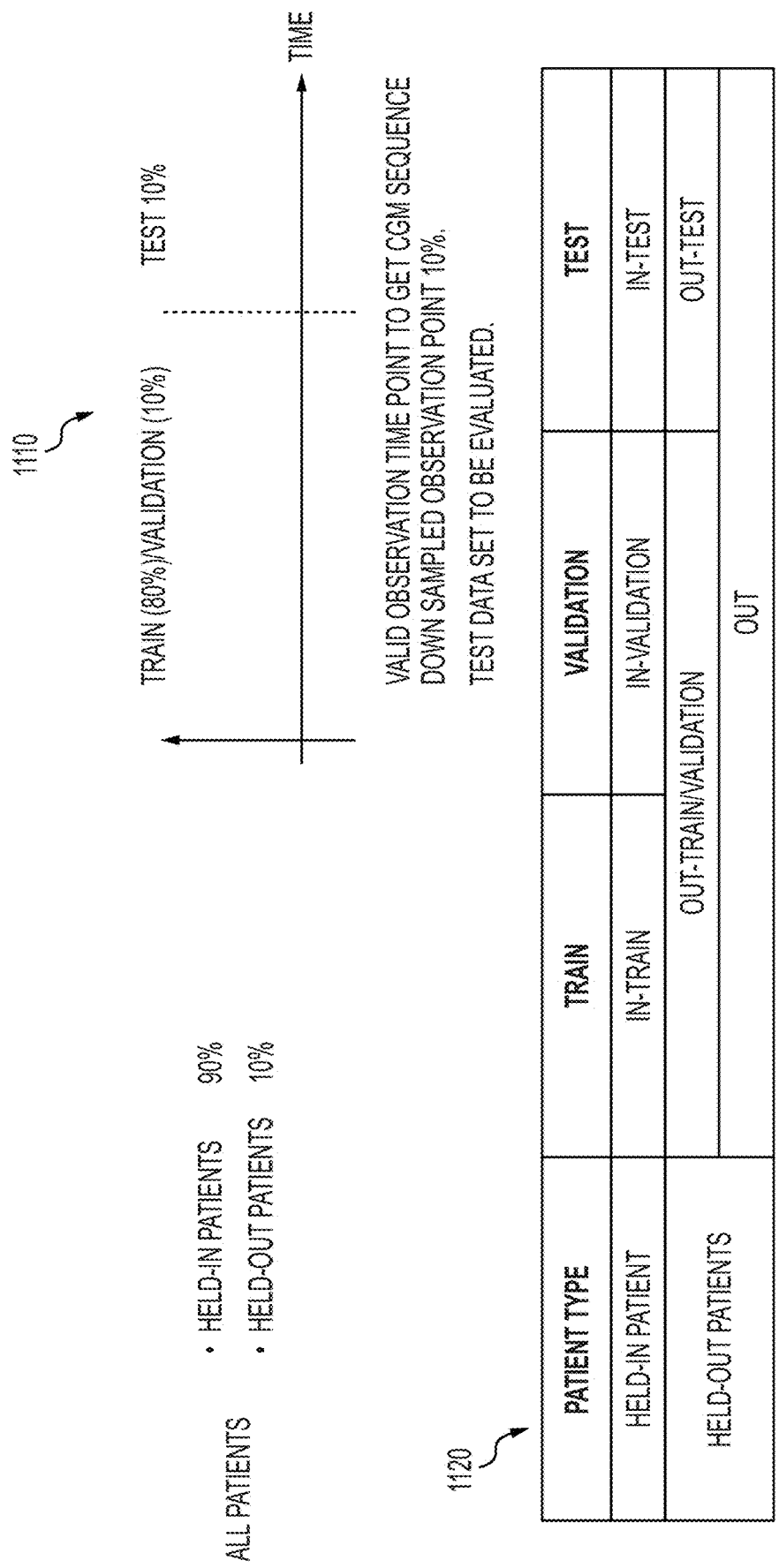

FIGS. 11A-11D show example plots of CGM prediction for groups of individuals, in accordance with one or more embodiments. FIGS. 11A-11D are generated based on experimental results obtained in accordance with the techniques disclosed herein. FIG. 11A depicts plot 1110 representing the CGM prediction model during training and testing. Table 1120 depicts the types of information used during training and testing. The CGM prediction model is trained using data from held-in patients (e.g., approximately 90 percent of the total patient population). The remaining data (e.g., approximately 10 percent) from held-in patients may then be used for validation and testing of the CGM prediction model. The CGM prediction model may then be given data from a set of held-out patients (e.g., data that has not been used for training purposes) for test evaluation (e.g., assessing the generalization of the prediction model). This process results in a trained model that is trained and validated using data from held-in patients and is further tested on data from completely different sources. As discussed below, generative machine learning models trained in accordance with the techniques disclosed herein produce comparable results (e.g., similar error rate at each interval for a different data set) between held-in and held-out patients. Further, metabolic value predictions made by such generative machine learning models exceed the accuracy provided by conventional techniques.

Figure 11B:
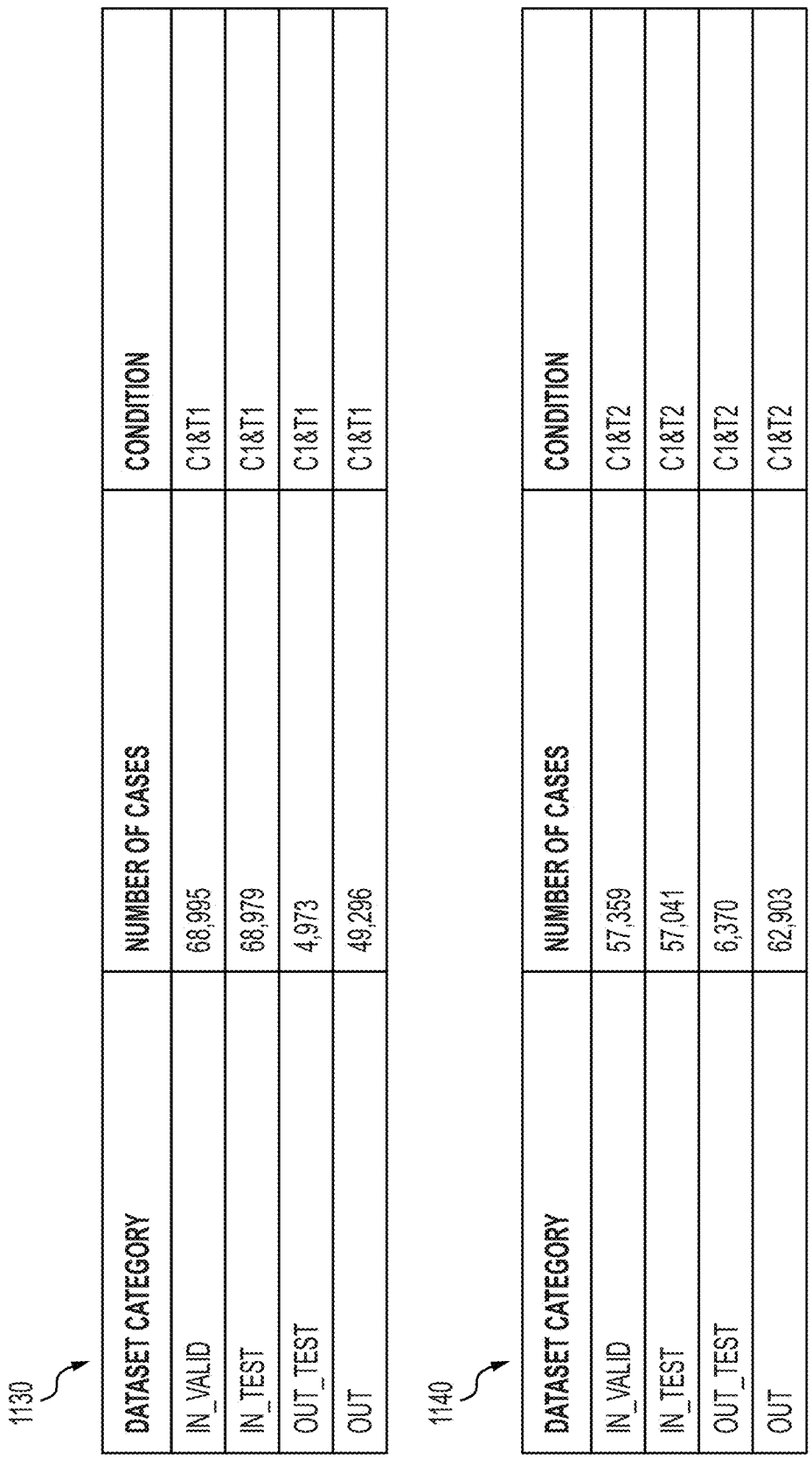

FIG. 11B depicts table 1130 and table 1140 with corresponding data used in training the CGM prediction model as described with FIG. 11A. For example, table 1130 includes in_valid data with 68,995 number of cases from C1&t1 (e.g., cohort 1 with type 1 diabetes) used to train the CGM prediction model. The CGM prediction model is then tested on in_test data with 68,979 number of cases from C1&t1. The CGM prediction model is then given out_test data with 4,973 cases from C1&t1. And, finally CGM prediction model is given out data with 49,296 cases from C1&t1. The process may be continued in a similar manner with the data from the table 1140 using C1&t2 (e.g., cohort 1 and type 2 diabetes). Referring back to FIG. 11A, the CGM prediction model is trained used a portion of the patient population and tested and validated using the remaining population before receiving a held-out data set for testing and evaluation.

Figure 11C:
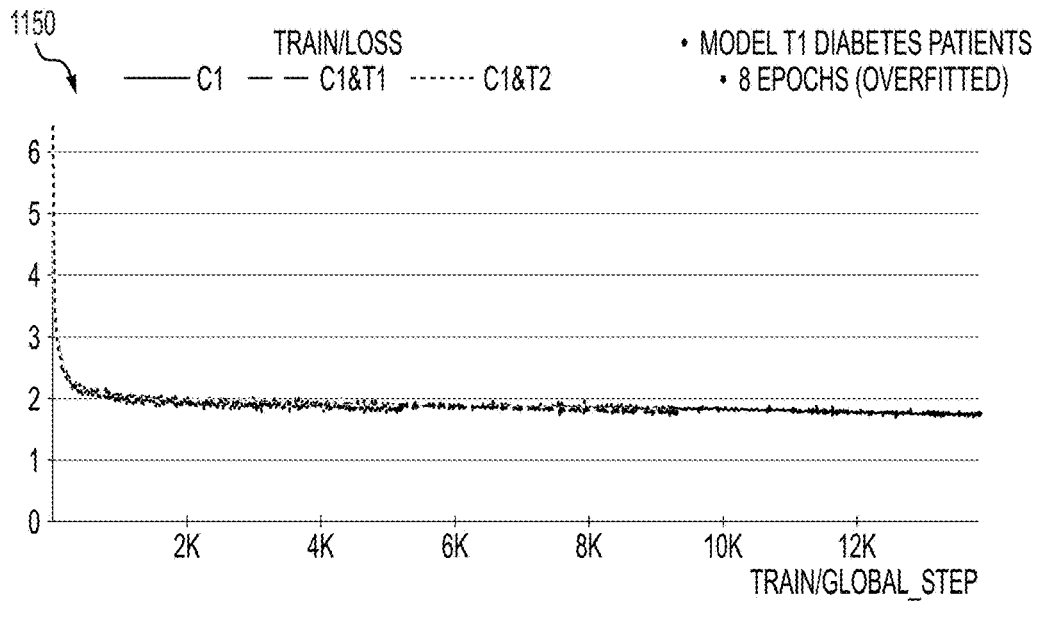
Figure 11C:
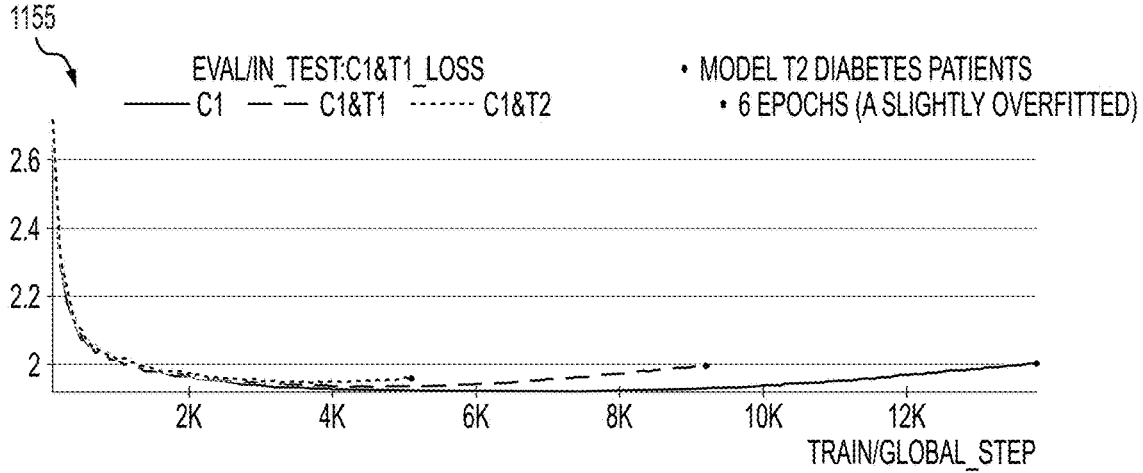
Figure 11C:
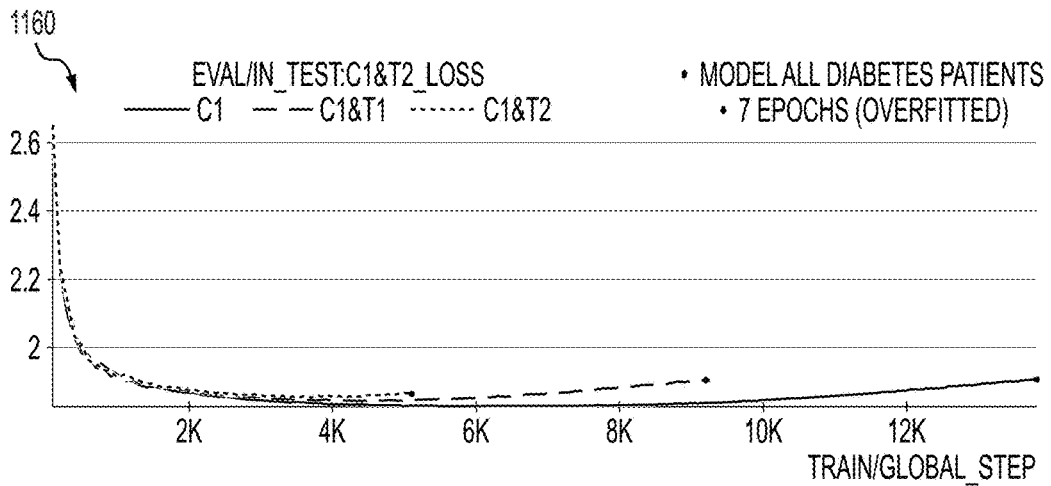

FIG. 11C depicts a set of plots for differently trained CGM prediction models. Each plot displays the x axis relating to the number of training batches, each batch having approximately 7 days worth of data points. Each plot depicts a curve associated with C1 patients (e.g., cohort 1), C1&t1 patients (e.g., cohort 1 with type 1 diabetes), and C1&t2 patients (e.g., cohort 1 with type 2 diabetes). Each plot depicts the trained CGM model using a specific patient data set (e.g., only type 1 diabetes). Plot 1150 depicts a trained CGM prediction model using type 1 diabetes patients. The test results of the CGM prediction model are shown to be overfitted (e.g., by looking at a few data points, the model has learned the exact pattern that it needs to identify the test data set, validation data set, and training data set). This trained model has the advantage of extremely high accuracy, but discriminatory nature is also very high (e.g., discriminate something it hasn't observed in its training). For example, an overfitted trained model may be advantageous in detecting a specific cancer cell (e.g., high accuracy and high discrimination for that specific cancer cell).

Plot 1155 depicts a trained CGM prediction model using type 2 diabetes patients. The test results of the CGM prediction model are shown to be slightly overfitted (e.g., moderate accuracy with moderate discrimination). A slightly overfitted model after about 4 k training steps may start to diverge and the errors may start to increase. An advantage of a slightly overfitted model is the generalization of the model. Meaning the model may be trained using one set of data but tested on a different set of data and still perform with a similar error rate, this is the preferred model. For example, training a model to detect squares of all sizes using squares having two pixel width lines. A slight overfitted model will detect squares of different sizes even those having different pixel width lines. On the other hand, an overfitted model trained in the same manner, will struggle to detect squares having three or four pixel width lines.

Plot 1160 depicts the use of a model trained using patients with all diabetes types (e.g., not just Type 1 and Type 2). The advantage of the plots depicted shows the differences of how training a prediction model affects the accuracy and discrimination with respect to different types of data used after training is complete. The goal is the train a model using specific patient types (e.g., type 1 diabetes only) to then apply the model to predict results for a different type of patient (e.g., type 2 diabetes). The result displays a transferability from type 1 diabetes to type 2 diabetes.

FIG. 11D depicts the evaluation of the trained model. After the CGM prediction model has been trained using a set of data, the model is given a new data set to test. For example, the CGM prediction model discussed in accordance with this example was trained using patients having type 2 diabetes. The trained CGM prediction model is then tested and evaluated to predict CGM values for patients having type 1 diabetes. Referring to baseline table 1170, a baseline prediction model trained using a set of data with a condition of type 1 diabetes may predict a CGM value at 30 minutes and 60 minutes with approximately 20 mg/dl and 30 mg/dl error rates, respectively. The CGM generative prediction model, trained using the same training data, may predict CGM values at intervals of 30 minutes, 60 minutes, and 2 hours. The CGM generative trained prediction model may normalized the CGM values using RMSE, as described above, to lower the error rate. Compared to baseline table 1170, table 1175 depicts the CGM GPT trained prediction model predicting CGM values at 30 minutes with an approximate 12.02 mg/dl error rate, at 60 minutes with an approximate 22.08 mg/dl error rate, and at 2-hours with an approximate 36.82 mg/dl error rate. As the model is used with the in-valid group resulting in approximately 12.02 mg/dl error rate, in-test group resulting in approximately 12.66 mg/dl error rate, and out-test resulting in approximately 13.5 mg/dl error rate. The trained model is then evaluated on out group (e.g., type 1 diabetes patient data) resulting in approximately 12.95 mg/dL error rate. Accordingly, as shown by the experimental results depicted in FIG. 11D, a model trained using type 1 diabetes data may result in a low error rate for predicting CGM values of type 2 diabetes patients. A similar process is depicted in table 1180 while training the CGM prediction model using patients having type 2 diabetes for testing and evaluation of patients having type 2 diabetes. As shown, error rates between 9.74 mg/dl and 10.96 mg/dl are observed for CGM value predictions 30 minutes into the future.

FIGS. 11E-11G show example plots of CGM prediction for groups of individuals, in accordance with one or more embodiments. FIGS. 11E-11G are results from a second experiment, as similarly described in FIGS. 11A-11D. FIG. 11E includes table 1182 depicting the CGM prediction model has been trained using multiple sets of data and the results of the model. For example, the CGM prediction model discussed in accordance with this example was trained using two sets of patients, (e.g., a first set of patients having type 1 and type 2 diabetes and a second set of patients having type 1 diabetes) to predict CGM values in type 1 diabetes patients. The CGM prediction model discussed in accordance with this example was also trained using two sets of patients (e.g., a first set of patients having type 1 and type 2 diabetes and a second set of patients having type 2 diabetes) to predict CGM values in type 2 diabetes patients. Referring to table 1182, the CGM generative prediction model, trained using the same training data, may predict CGM values at intervals of 30 minutes (See FIG. 11E), 60 minutes (See FIG. 11F), and 2 hours (See FIG. 11G). The CGM generative trained prediction model may normalized the CGM values using RMSE, as described above, to lower the error rate. Table 1182 depicts the CGM GPT trained prediction model using the first set of patients (e.g., type 1 and types 2 diabetes) to predict CGM values at 30 minutes for patients with type 1 diabetes with an approximate 12.00 mg/dl error rate. As the model is used with the future test group resulting in approximately 12.99 mg/dl error rate. The hold-out group resulting in approximately 12.81 mg/dl error rate and the hold-out future group resulting in approximately 13.54 mg/dL error rate. Using the second patient set (e.g., type 1 diabetes) the CGM GPT trained model predicts CGM values at 30 minutes for patients with type 1 diabetes with an approximate 12.17 mg/dl error rate. As the model is used with the future test group resulting in an approximate 13.02 mg/dl error rate. The hold-out group resulting in approximately 12.81 mg/dl error rate and the hold-out future group resulting in approximately 13.46 mg/dl error rate.

Table 1182 further includes the CGM GPT trained prediction model using a first set of patients (e.g., type 1 and types 2 diabetes) and a second set of patients (e.g., type 1 diabetes) to predict CGM values at 30 minutes for patient having type 2 diabetes. The CGM GPT model uses the first set of patients (e.g., type 1 and types 2 diabetes) with an approximate 10.56 mg/dl error rate. As the model is used with the future test group resulting in an approximate 11.25 mg/dl error rate. The hold-out group resulting in an approximate 11.25 mg/dl error rate and the hold-out future group resulting in approximately 11.24 mg/dl error rate. The CGM GPT model using the second set of patients (e.g., type 2 diabetes) to predict CM values for type 2 diabetes patients at 30 minutes with an approximate 10.52 mg/dl error rate. As the model uses the future test group resulting in an approximate 11.17 mg/dl error rate. The hold-out group resulting in an approximate 10.41 mg/dl error rate and the hold-out future group with an approximate 11.23 mg/dl error rate.

FIG. 11F depicts table 1184 as similarly described with table 1182 in FIG. 11E. For example, the CGM prediction model discussed in accordance with this example was trained using two sets of patients, (e.g., a first set of patients having type 1 and type 2 diabetes and a second set of patients having type 1 diabetes) to predict CGM values in type 1 diabetes patients. The CGM prediction model discussed in accordance with this example was also trained using two sets of patients (e.g., a first set of patients having type 1 and type 2 diabetes and a second set of patients having type 2 diabetes) to predict CGM values in type 2 diabetes patients. The CGM generative trained prediction model may normalized the CGM values using RMSE, as described above, to lower the error rate. Table 1184 depicts the CGM GPT trained prediction model using the first set of patients (e.g., type 1 and types 2 diabetes) to predict CGM values at 60 minutes for patients with type 1 diabetes with an approximate 22.21 mg/dl error rate. As the model is used with the future test group resulting in approximately 23.19 mg/dl error rate. The hold-out group resulting in approximately 23.52 mg/dl error rate and the hold-out future group resulting in approximately 24.27 mg/dl error rate. Using the second patient set (e.g., type 1 diabetes) the CGM GPT trained model predicts CGM values at 60 minutes for patients with type 1 diabetes with an approximate 22.45 mg/dl error rate. As the model is used with the future test group resulting in an approximate 23.30 mg/dl error rate. The hold-out group resulting in approximately 23.54 mg/dl error rate and the hold-out future group resulting in approximately 24.31 mg/dL error rate.

Table 1184 further includes the CGM GPT trained prediction model using a first set of patients (e.g., type 1 and types 2 diabetes) and a second set of patients (e.g., type 1 diabetes) to predict CGM values at 60 minutes for patient having type 2 diabetes. The CGM GPT model uses the first set of patients (e.g., type 1 and types 2 diabetes) with an approximate 18.42 mg/dl error rate. As the model is used with the future test group resulting in an approximate 19.21 mg/dl error rate. The hold-out group resulting in an approximate 17.58 mg/dl error rate and the hold-out future group resulting in approximately 18.53 mg/dl error rate. The CGM GPT model using the second set of patients (e.g., type 2 diabetes) to predict CM values for type 2 diabetes patients at 60 minutes with an approximate 18.26 mg/dl error rate. As the model uses the future test group resulting in an approximate 19.01 mg/dl error rate. The hold-out group resulting in an approximate 17.47 mg/dl error rate and the hold-out future group with an approximate 18.49 mg/dl error rate.

FIG. 11G depicts table 1186 as similarly described with table 1182 in FIG. 11E and table 1184 in FIG. 11F. For example, the CGM prediction model discussed in accordance with this example was trained using two sets of patients, (e.g., a first set of patients having type 1 and type 2 diabetes and a second set of patients having type 1 diabetes) to predict CGM values in type 1 diabetes patients. The CGM prediction model discussed in accordance with this example was also trained using two sets of patients (e.g., a first set of patients having type 1 and type 2 diabetes and a second set of patients having type 2 diabetes) to predict CGM values in type 2 diabetes patients. The CGM generative trained prediction model may normalized the CGM values using RMSE, as described above, to lower the error rate. Table 1186 depicts the CGM GPT trained prediction model using the first set of patients (e.g., type 1 and types 2 diabetes) to predict CGM values at 2 hours for patients with type 1 diabetes with an approximate 37.39 mg/dL error rate. As the model is used with the future test group resulting in approximately 38.40 mg/dL error rate. The hold-out group resulting in approximately 39.80 mg/dl error rate and the hold-out future group resulting in approximately 40.80 mg/dl error rate. Using the second patient set (e.g., type 1 diabetes) the CGM GPT trained model predicts CGM values at 2 hours for patients with type 1 diabetes with an approximate 37.96 mg/dl error rate. As the model is used with the future test group resulting in an approximate 38.77 mg/dL error rate. The hold-out group resulting in approximately 40.08 mg/dl error rate and the hold-out future group resulting in approximately 41.27 mg/dl error rate.

Table 1186 further includes the CGM GPT trained prediction model using a first set of patients (e.g., type 1 and types 2 diabetes) and a second set of patients (e.g., type 1 diabetes) to predict CGM values at 2 hours for patient having type 2 diabetes. The CGM GPT model uses the first set of patients (e.g., type 1 and types 2 diabetes) with an approximate 29.95 mg/dl error rate. As the model is used with the future test group resulting in an approximate 30.69 mg/dl error rate. The hold-out group resulting in an approximate 37.69 mg/dl error rate and the hold-out future group resulting in approximately 28.90 mg/dl error rate. The CGM GPT model using the second set of patients (e.g., type 2 diabetes) to predict CM values for type 2 diabetes patients at 2 hours with an approximate 29.51 mg/dl error rate. As the model uses the future test group resulting in an approximate 30.20 mg/dl error rate. The hold-out group resulting in an approximate 27.35 mg/dl error rate and the hold-out future group with an approximate 28.64 mg/dL error rate.

FIGS. 11H-11I depict error rates associated with CGM value predictions using conventional methods. As shown, the error rates using such conventional methods are higher than those output by the generative machine learning model based techniques disclosed herein. For example, as shown in table 1190 in FIG. 11H, the error rate observed in the Li2019CRNNforGlucosePred study resulted in a 30 minute CGM value predicted error rate of 21.07 mg/dl and a 60 minute error rate of 33.27 mg/dL. Table 1190 further depicts an error rate observed in the Li2019GluNet study resulted in a 30 minute CGM value predicted error rate of 19.19 mg/dl and a 60 minute CGM value predicted error rate of 31.78 mg/dl using the ABC4D Project Dataset. The Li2019GluNet study further resulted in a 30 minute CGM value predicted error rate of 19.28 mg/dl and a 60 minute CGM value predicted error rate of 31.83 mg/dl using the OhioT1DM Dataset. Table 1190 further depicts an error rate observed in the Zhu2022FCNN PersonalizedBGPred study resulted in a 30 minute CGM value predicted error rate of 18.64 mg/dl and a 60 minute CGM value predicted error rate of 31.07 mg/dl using the OhioT1DM Dataset. The Zhu2022FCNN PersonalizedBGPred study further resulted in a 30 minute CGM value predicted error rate of 20.23 mg/dL and a 60 minute CGM value predicted error rate of 35.40 mg/dl using the ARISES Dataset. The Zhu2022FCNN PersonalizedBGPred study further resulted in a 30 minute CGM value predicted error rate of 20.25 mg/dl and a 60 minute CGM value predicted error rate of 34.03 mg/dl using the ABC4D Dataset.

Table 1195 in FIG. 11I depicts the error rate observed in the Zhu2022EnhanceType1DiabetesNPL (RNN) study resulted in a 30 minute CGM value predicted error rate of 20.92 mg/dL, a 45 minute CGM value predicted error rate of 28.99 mg/dL, and a 60 minute CGM value predicted error rate of 35.28 mg/dL. Table 1195 further depicts an error rate observed in the Zhu2023ETFTforMultiHorizonGlucosePred study resulted in a 30 minute CGM value predicted error rate of 19.09 mg/dL and a 60 minute CGM value predicted error rate of 32.31 mg/dL.

Figure 12A:
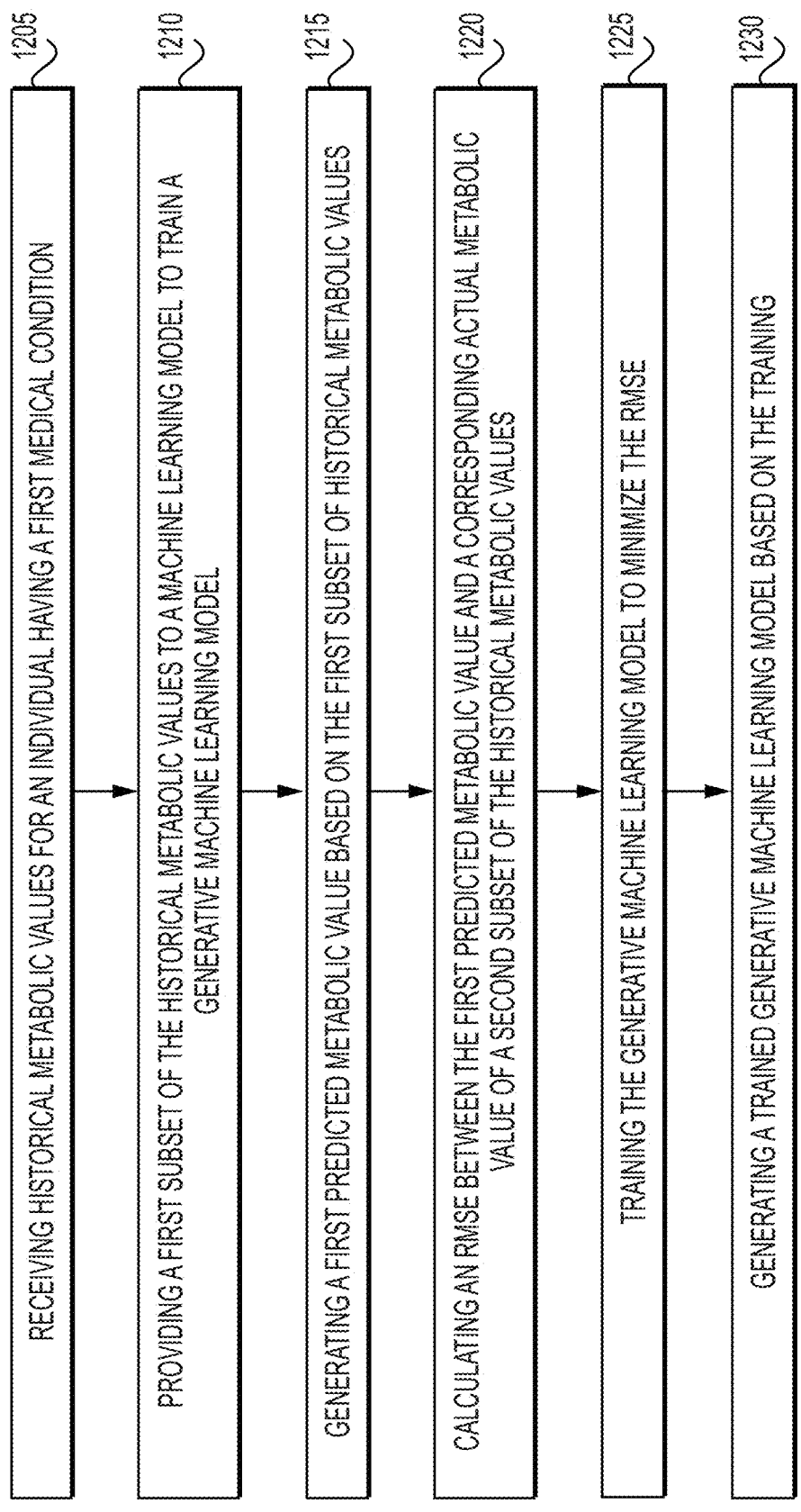
FIGS. 12A-12B show example flow diagrams, in accordance with one or more embodiments.
Figure 12B:
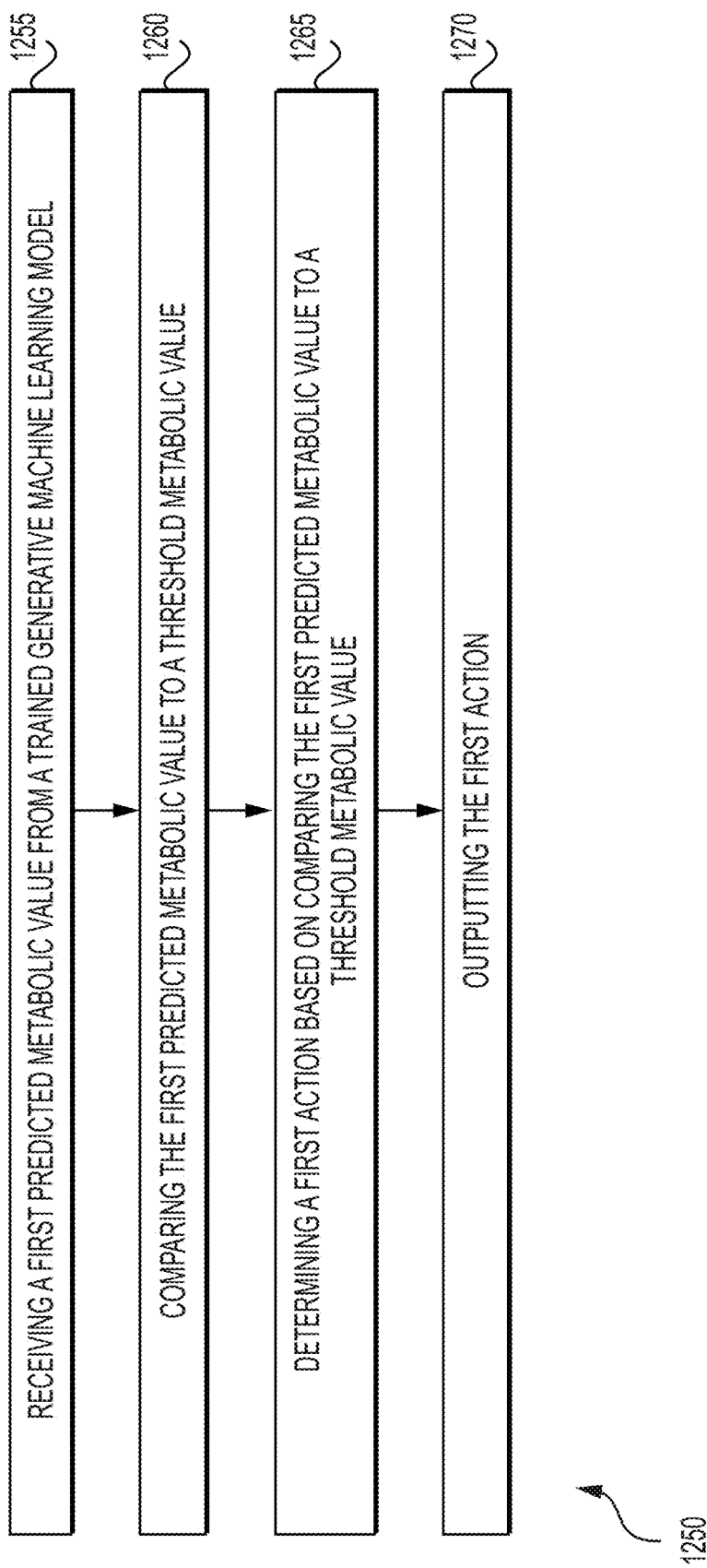

FIGS. 12A-12B show example flow diagrams, in accordance with one or more embodiments. FIG. 12A shows an example flow diagram, in accordance with one or more embodiments, for training a generative machine learning model. Flow diagram 1200 may start with step 1205 of receiving historical metabolic values for an individual having a first medical condition. Next, step 1210 may include providing a first subset of the historical metabolic values to a machine learning model to train a generative machine learning model. Next, step 1215 may include generating a first predicted metabolic value based on the first subset of historical metabolic values. Next, step 1220 may include calculating a difference (e.g., an RMSE) between the first predicted metabolic value and a corresponding actual metabolic value of a second subset of the historical metabolic values. Next, step 1225 may include training the generative machine learning model to minimize the difference (e.g., RMSE). Next, step 1230 may include generating a trained generative machine learning model based on the training. Although the steps are described in a specific order, the steps may be performed out of order or repeated as necessary.

FIG. 12B shows an example flow diagram, in accordance with one or more embodiments, for using the trained generative machine learning model. Flow diagram 1250 may start with step 1255 and include receiving a first predetermined metabolic value from a trained generative machine learning model. The trained generative machine learning model may include the trained model as described in FIG. 12A. Next, step 1260 may include comparing the first predicted metabolic value to a threshold metabolic value. Next, step 1265 may include determining a first action based on comparing the first predicted metabolic value to the threshold metabolic value. Next, step 1270 may include outputting the first action.

Accordingly, in accordance with techniques disclosed herein, a generative machine learning model may be trained using training data that includes metabolic values from a cohort of individuals. The model may be validated based on metabolic values from a subset of the cohort of individuals whose data was not used for the training. The model may be tested on metabolic value data from a separate cohort of individuals.

The trained model may be used in an inference phase to predict metabolic values for one or more given individuals. Such predictions may be augmented using MEDAL factor or other supplementary variables and/or supplementary conditions, as discussed herein.

Additionally, the predicted metabolic values output by a trained machine learning model may be provided to a processor configured to trigger an action based on the predicted metabolic values. For example, predicted CGM values may be compared to goal CGM values. Based on a difference between the predicted CGM values and the goal CGM values, the processor may trigger a medical device (e.g., insulin pump) to output a medication (e.g., insulin) to the given individual associated with the predicted and goal CGM values. The processor may trigger the medical device at a given time and/or based on a given dosage determined based on the comparison between the predicted CGM value and goal CGM values (e.g., based on a threshold difference between the predicted and goal CGM values and a future point in time). The trigger action may include generating a notification on a user device to alert the user to take an action (e.g., a MEDAL action, an exercise recommendation, a fluid intake recommendation, a rest recommendation, a food recommendation, or an insulin recommendation, etc.). The trigger action may include automatically placing a food order using an application programing interface (API) for communication with an application on a user device. The trigger action may include receiving food items available to a user based on accessing a database (e.g., smart appliance refrigerator) and identifying one or more food items based on comparing the predicted and goal CGM values.

One or more generative prediction models may be trained using similar functions as described above, for conditions other than diabetes (e.g., using metabolic variables other than CGM variables). For example, while in the above scenario, the purpose of the training model is to output CGM values for diabetes patients, the transferability of a similarly trained model may use heart rate electrocardiogram (ECG), heart rate, weight (e.g., for the purpose of congestive heart failure), and/or other metabolic values to train a generative machine learning model to output corresponding future metabolic values during an inference phase. Training a first model using date from patients having one diagnosis (e.g., heart failure with preserved ejection fraction (HFpEF)) and applying the trained model on patients having a different diagnosis (e.g., heart failure with reduced ejection fraction (HFrEF)). Congestive heart failure patients have to manage their weight based on water retention, and variability depends on how much fluid one is retaining. For example, a small change (e.g., 1-2 pounds) may be okay, while a larger change (e.g., more than 5 pounds) may be bad, showing the patient to have significant edema which may cause the heart to decompensate. Using a generative trained model, as described above, may predict water weight retention and determine the path (e.g., predicted values over a period of time) of water weight. The model may predict outcomes and solutions during the path to make corrections (e.g., take another pill, avoid sodium, etc.). Additional systems having discrete time signals that may include metabolic characteristics with rapidly changing and/or fluctuating values may be used by the trained generative model to generate similar predictions.

As discussed herein, in one example, predictions from the CGM model may be used in conjunction with MEDAL characteristics, as described above. For example, a CMG model may predict a CGM value for a user at the 2-hour interval. The user may query the model requesting additional information about the CMG value and different activities or outcomes based on eating certain food (e.g., carbohydrates) or exercise (e.g., run two miles). The model may output one or more scenarios to include the effects of the CGM values at the 2-hour interval if the user were to eat or exercise as queried. The user may also query the model to see what MEDAL characteristics are available to maintain the current or predicted CGM value at a particular interval (e.g., user can eat 10 g of carbohydrates or run 2 miles and will maintain a similar CGM value at the 2-hour interval).

Another example may include the use of trained model in conjunction with Instacart® or another food delivery service. A user may query the model by inputting the food order from Instacart® for the model to then predict the effects the food may have on the user at different time intervals. The model may output suggestions on the types and/or amounts of the food ordered to maintain consistent or healthy CGM values. Or in the alternative, predict the CGM values based on some or all of the food ordered being consumed.

Another example may include a connection to a user's home appliance network (e.g., smart refrigerator). A user may query the model to take inventory of the food inside the refrigerator and give suggestions based on the predicted CGM values as to what food may be consumed or avoided. A user may also query the home appliance when grocery shopping to determine the types of food to purchase in order to maintain a healthy blood glucose level.

Figure 13:
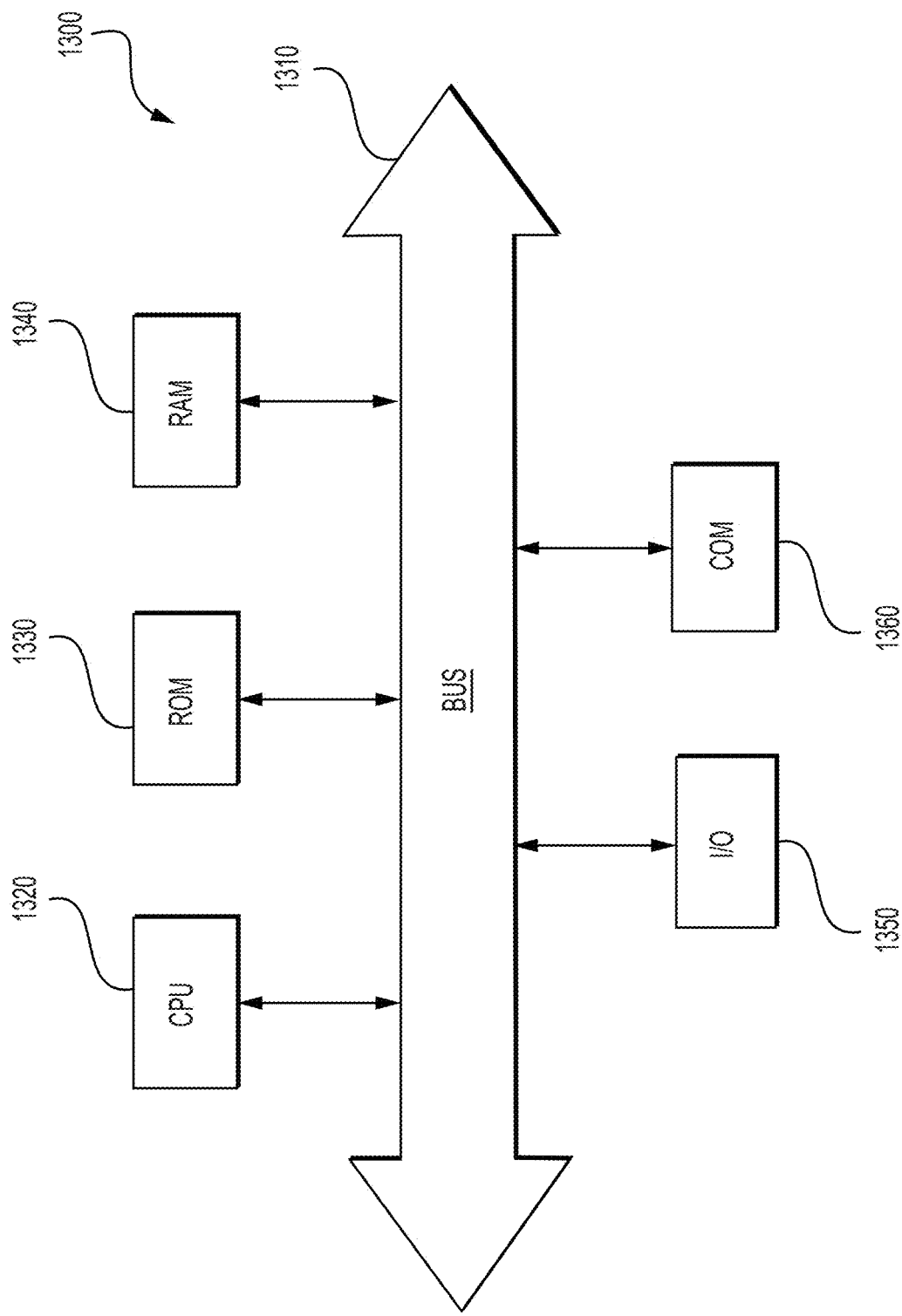
FIG. 13 is a simplified functional block diagram of a computer, in accordance with one or more embodiments.

FIG. 13 is a simplified functional block diagram of a computer, in accordance with one or more embodiments. A device 1300 for a computer or server or the like, for example, may include a data communication interface ports 1360 for packet data communication. The device also may include a central processing unit (CPU) 1320, in the form of one or more processors, for executing program instructions. The platform typically includes an internal communication bus 1310, program storage, and data storage for various data files to be processed and/or communicated by the platform such as ROM 1330 and RAM 1340 or the like. The hardware elements, operating systems, and programming languages of such equipment are conventional in nature, and it is presumed that those skilled in the art are adequately familiar therewith. The device 1300 also may include input and output ports 1350 to connect with input and output devices such as keyboards, mice, touchscreens, monitors, displays, etc., and data communication interface ports 1360. Of course, the various server functions may be implemented in a distributed fashion on a number of similar platforms to distribute the processing load. Alternatively, the servers may be implemented by appropriate programming of one computer hardware platform.

It would be apparent to one of skill in the relevant art that the present disclosure, as described herein, can be implemented in many different examples of software, hardware, firmware, and/or the entities illustrated in the figures. Any actual software code with the specialized control of hardware to implement examples is not limiting of the detailed description. Thus, examples are described herein with the understanding that modifications and variations of the examples are possible, given the level of detail presented herein. Aspects of the described subject matter may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Figure 14A:
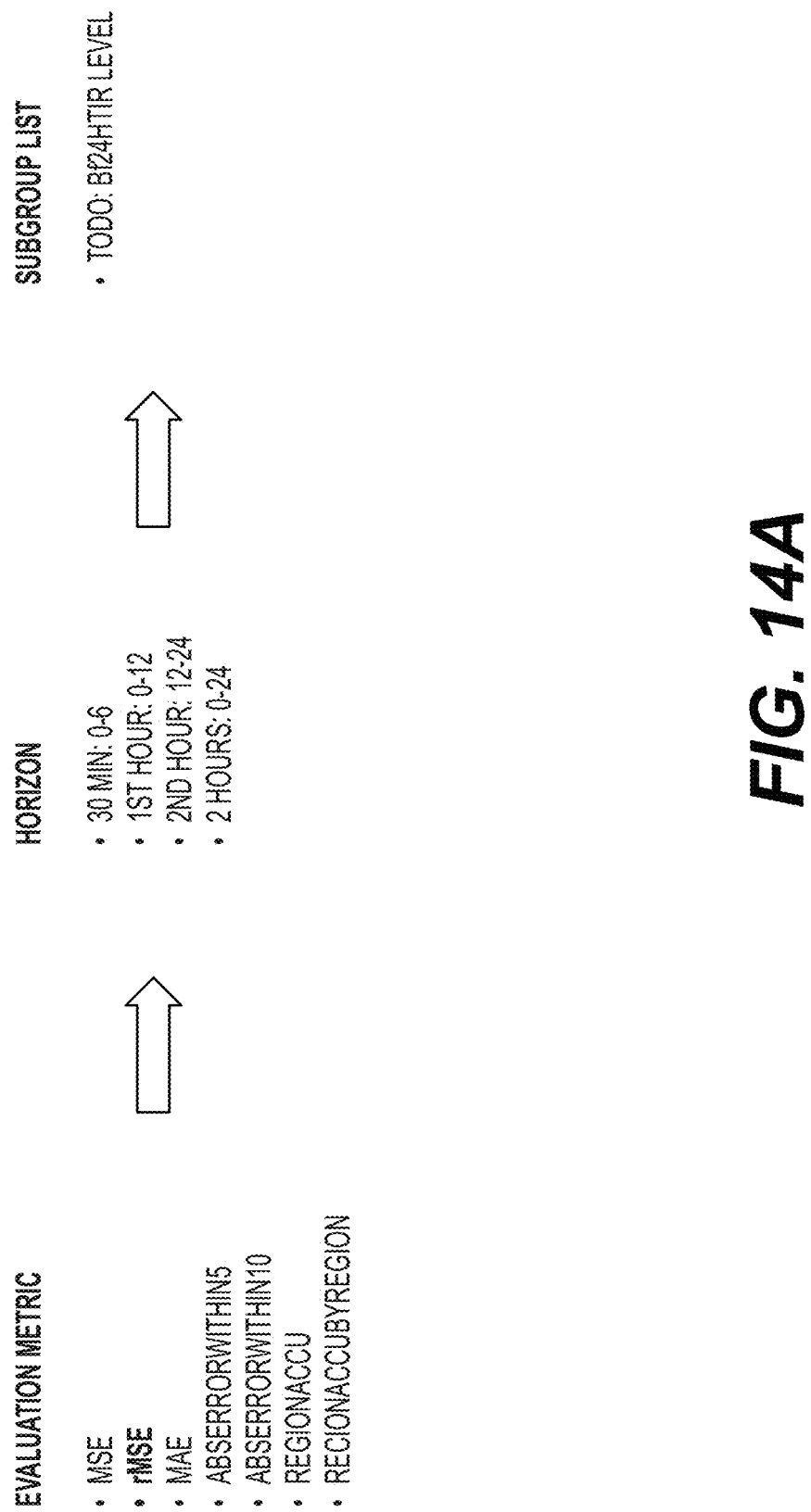
FIG. 14A shows a flow chart for an evaluation method, in accordance with one or more embodiments.

FIG. 14A shows a flow chart for an evaluation method, in accordance with one or more embodiments. One or more embodiments may include the use of different evaluation metrics. Flow chart 1400A may include mean squared error (MSE), root mean squared error (RMSE), mean absolute error (MAE), absolute error (ABS) (e.g., within approximately 5 or within approximately 10, etc.), region accuracy, and region accuracy by region. Each of the evaluation metrics used may include a horizon and a subgroup list. The horizon may include, for example, 30 minutes, $1^{st}$ hour, $2^{nd}$ hour, and 2 hours. The subgroup list may include, for example, InOutSplit, Hour, AgeGroup, Gender, MEDAL record number, and TODO: Bf24HTIR level.

Figure 14B:
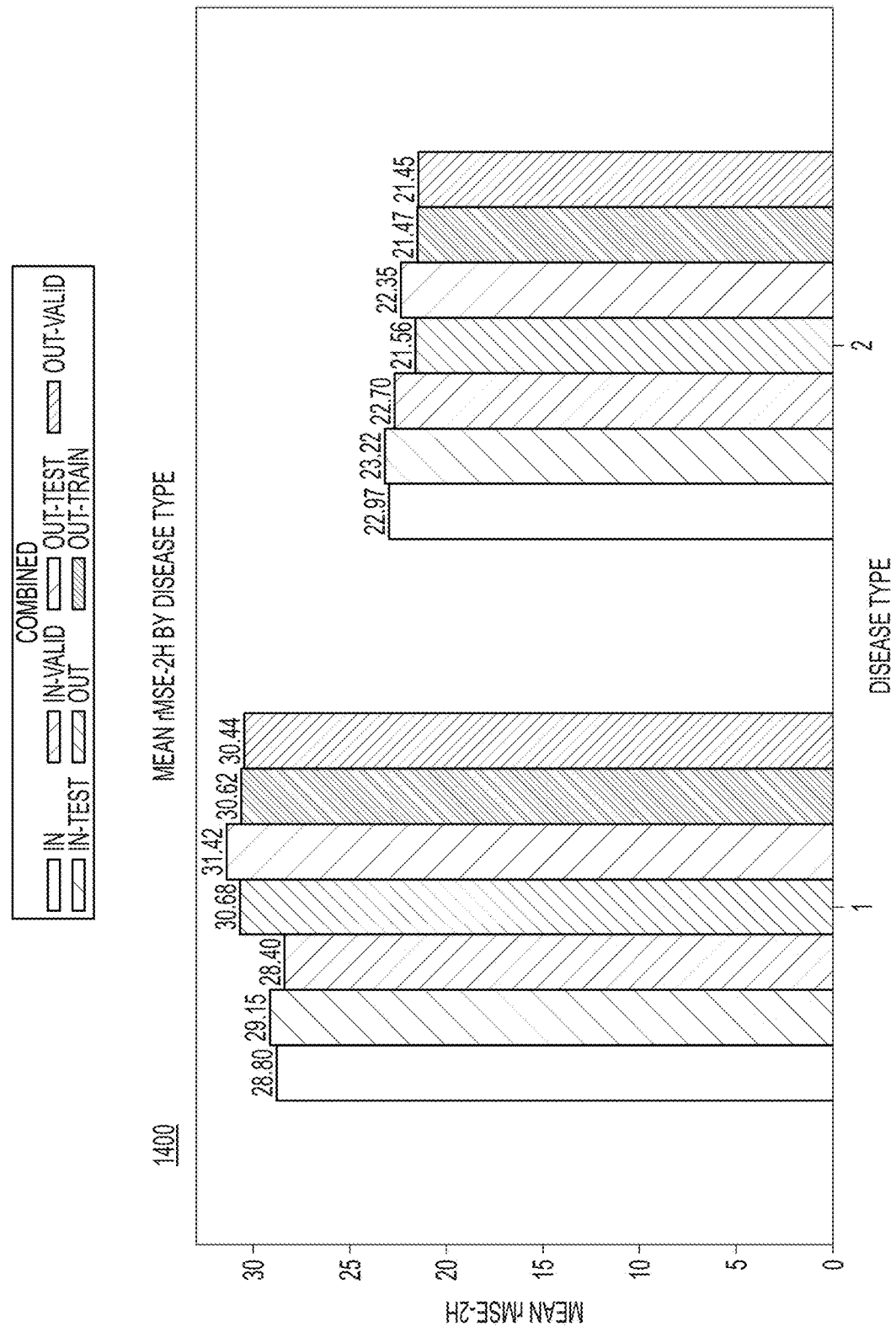
FIGS. 14B-14N shows example CGM prediction outputs for groups of individuals, in accordance with one or more embodiments.
Figure 14C:
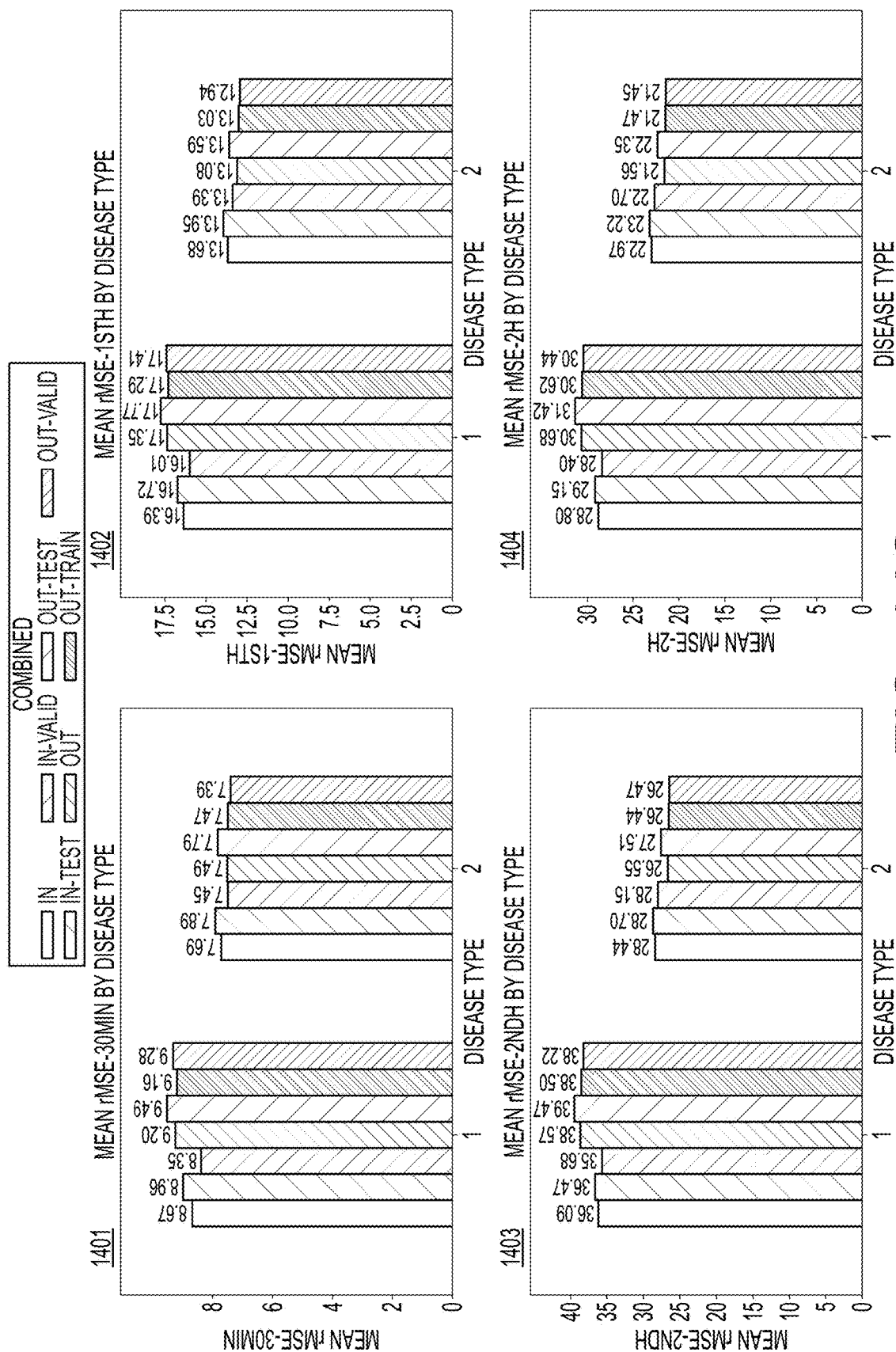

FIGS. 14B-14N shows example CGM prediction outputs for groups of individuals, in accordance with one or more embodiments. FIG. 14B depicts plot 1400 showing predicted CGM values for type 1 and type 2 diabetes patients using RMSE at the 2-hour interval. FIG. 14C depicts plot 1401, plot 1402, plot 1403, and plot 1404. Plot 1401 shows the predicted CGM values for type 1 and type 2 diabetes patients using RMSE at the 30 minute interval. Plot 1402 shows the predicted CGM values for type 1 and type 2 diabetes patients using RMSE at the $1^{st}$ hour interval. Plot 1403 shows the predicted CGM values for type 1 and type 2 diabetes patients using RMSE at the $2^{nd}$ hour interval. Plot 1404 shows the predicted CGM values for type 1 and type 2 diabetes patients at the 2-hour interval.

Figure 14D:
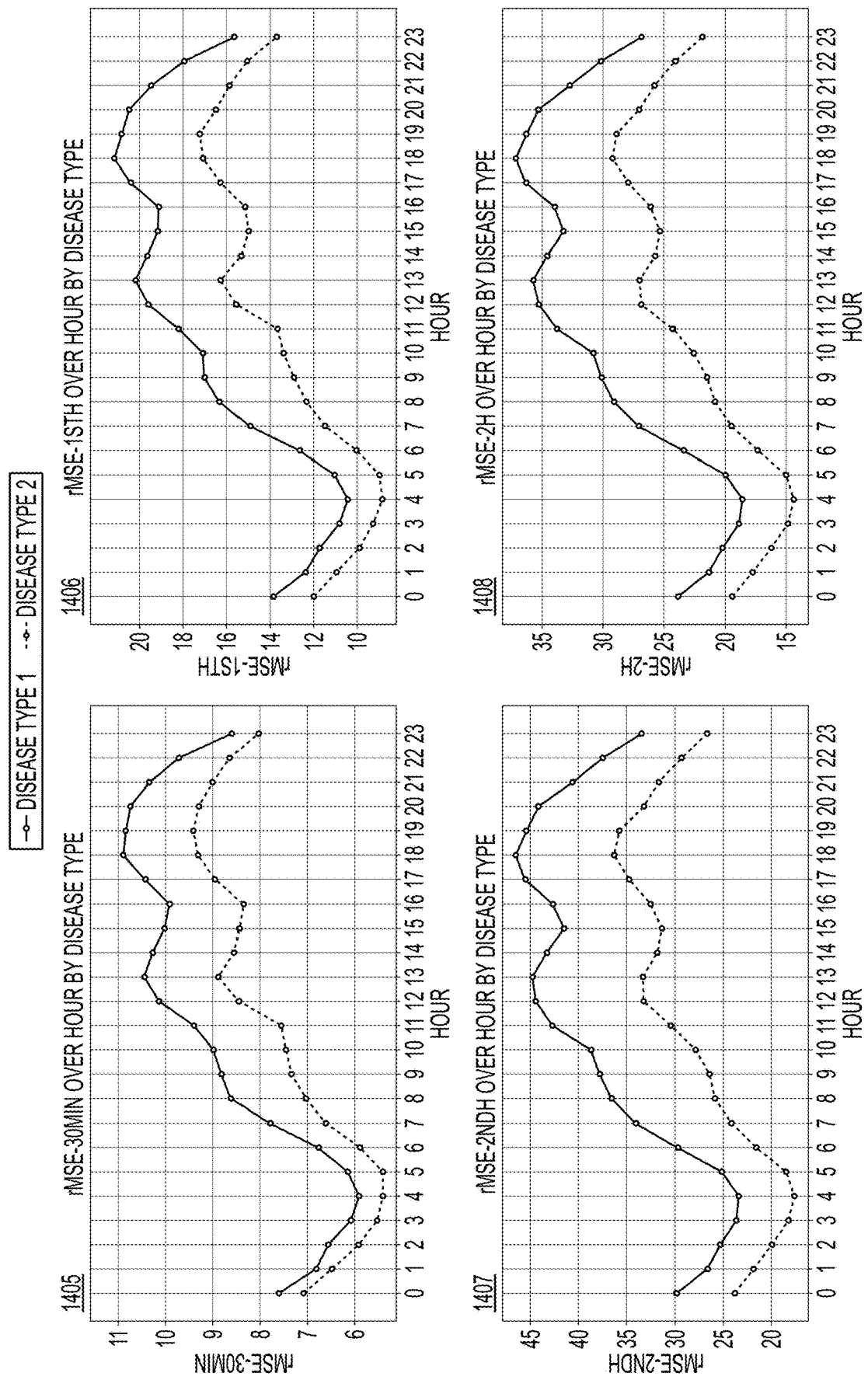

FIG. 14D depicts plot 1405, plot 1406, plot 1407, and plot 1408 showing the predicted CGM values for type 1 and type 2 diabetes patients by the hour. Plot 1405 shows the predicted CGM values by the hour for type 1 and type 2 diabetes patients using RMSE at the 30 minute interval. Plot 1406 shows the predicted CGM values by the hour for type 1 and type 2 diabetes patients using RMSE at the $1^{st}$ hour interval. Plot 1407 shows the predicted CGM values by the hour for type 1 and type 2 diabetes patients using RMSE at the $2^{nd}$ hour interval. Plot 1408 shows the predicted CGM values for by the hour type 1 and type 2 diabetes patients at the 2-hour interval.

Figure 14E:
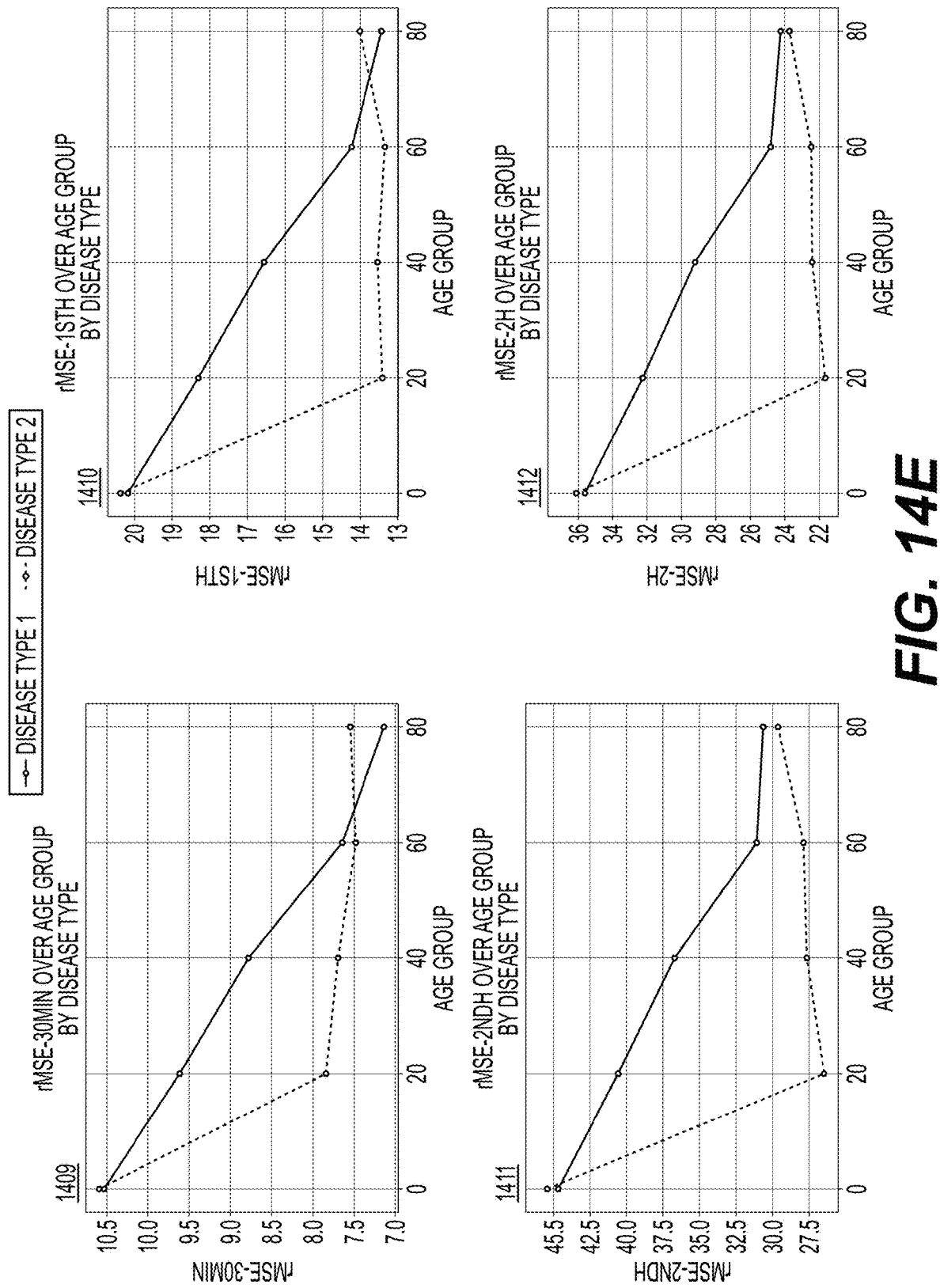

FIG. 14E depicts plot 1409, plot 1410, plot 1411, and plot 1412 showing the predicted CGM values for type 1 and type 2 diabetes patients by age group. Plot 1409 shows the predicted CGM values for type 1 and type 2 diabetes patients using RMSE at the 30 minute interval. Plot 1410 shows the predicted CGM values for type 1 and type 2 diabetes patients using RMSE at the $1^{st}$ hour interval. Plot 1411 shows the predicted CGM values for type 1 and type 2 diabetes patients using RMSE at the $2^{nd}$ hour interval. Plot 1412 shows the predicted CGM values for type 1 and type 2 diabetes patients at the 2-hour interval.

Figure 14F:
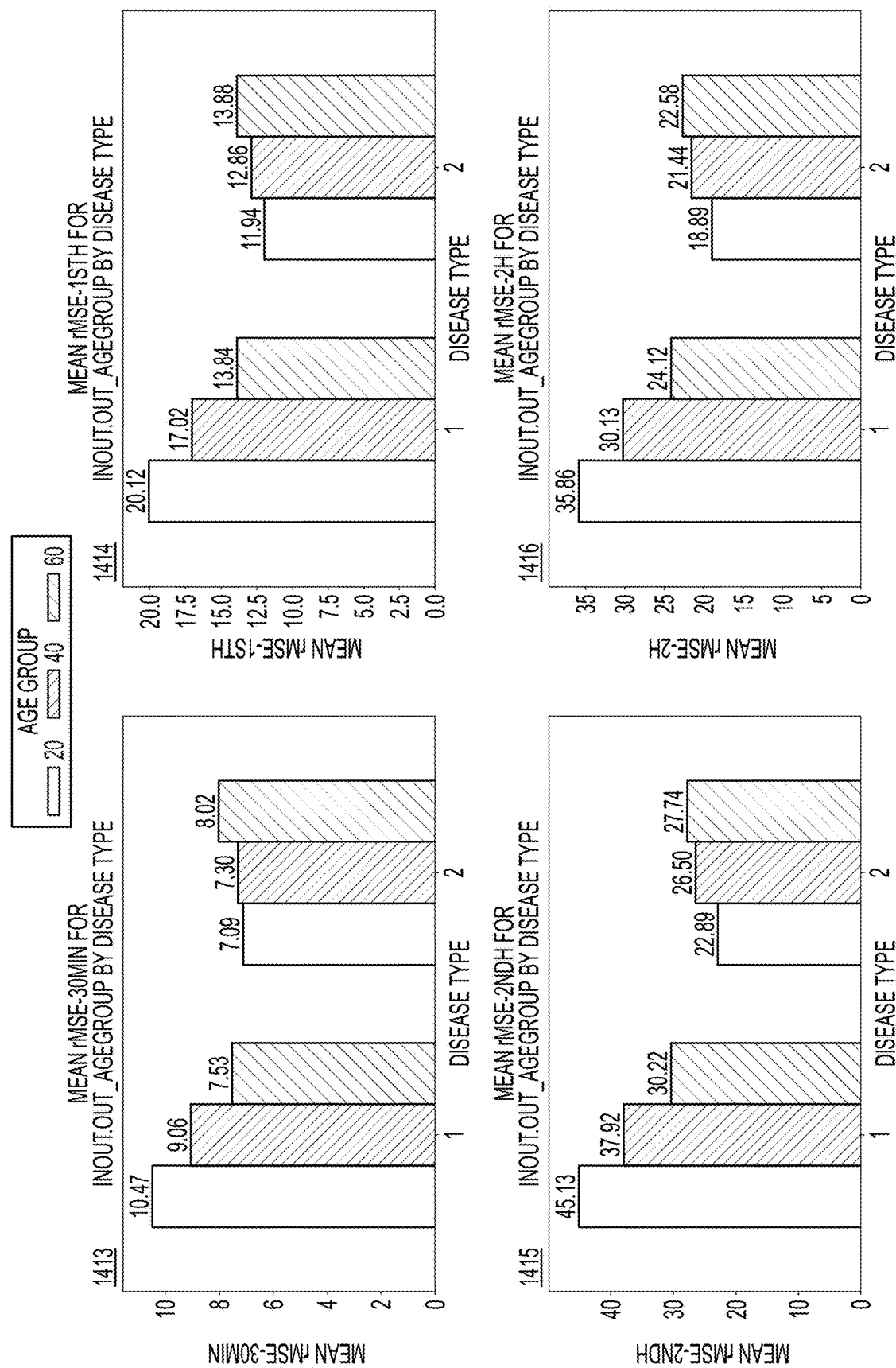

FIG. 14F depicts plot 1413, plot 1414, plot 1415, and plot 1416 showing the predicted CGM values for type 1 and type 2 diabetes patients by InOut_Out_Age group. Plot 1413 shows the predicted CGM values for type 1 and type 2 diabetes patients using RMSE at the 30 minute interval. Plot 1414 shows the predicted CGM values for type 1 and type 2 diabetes patients using RMSE at the $1^{st}$ hour interval. Plot 1415 shows the predicted CGM values for type 1 and type 2 diabetes patients using RMSE at the $2^{nd}$ hour interval. Plot 1416 shows the predicted CGM values for type 1 and type 2 diabetes patients at the 2-hour interval.

Figure 14G:
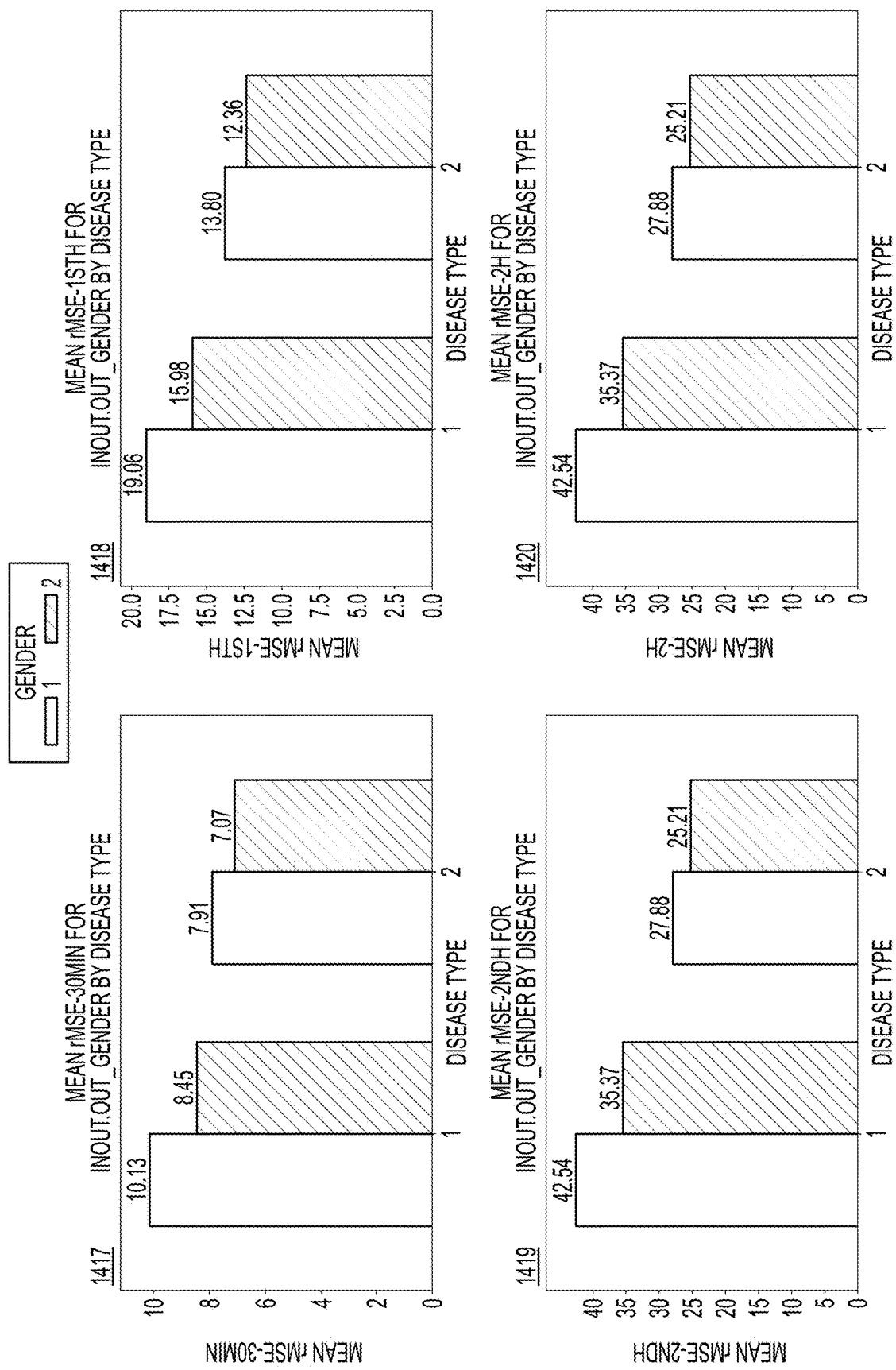

FIG. 14G depicts plot 1417, plot 1418, plot 1419, and plot 1420 showing the predicted CGM values for type 1 and type 2 diabetes patients for InOut_Out by gender. Plot 1417 shows the predicted CGM values for type 1 and type 2 diabetes patients using RMSE at the 30 minute interval. Plot 1418 shows the predicted CGM values for type 1 and type 2 diabetes patients using RMSE at the $1^{st}$ hour interval. Plot 1419 shows the predicted CGM values for type 1 and type 2 diabetes patients using RMSE at the $2^{nd}$ hour interval. Plot 1420 shows the predicted CGM values for type 1 and type 2 diabetes patients at the 2-hour interval.

Figure 14H:
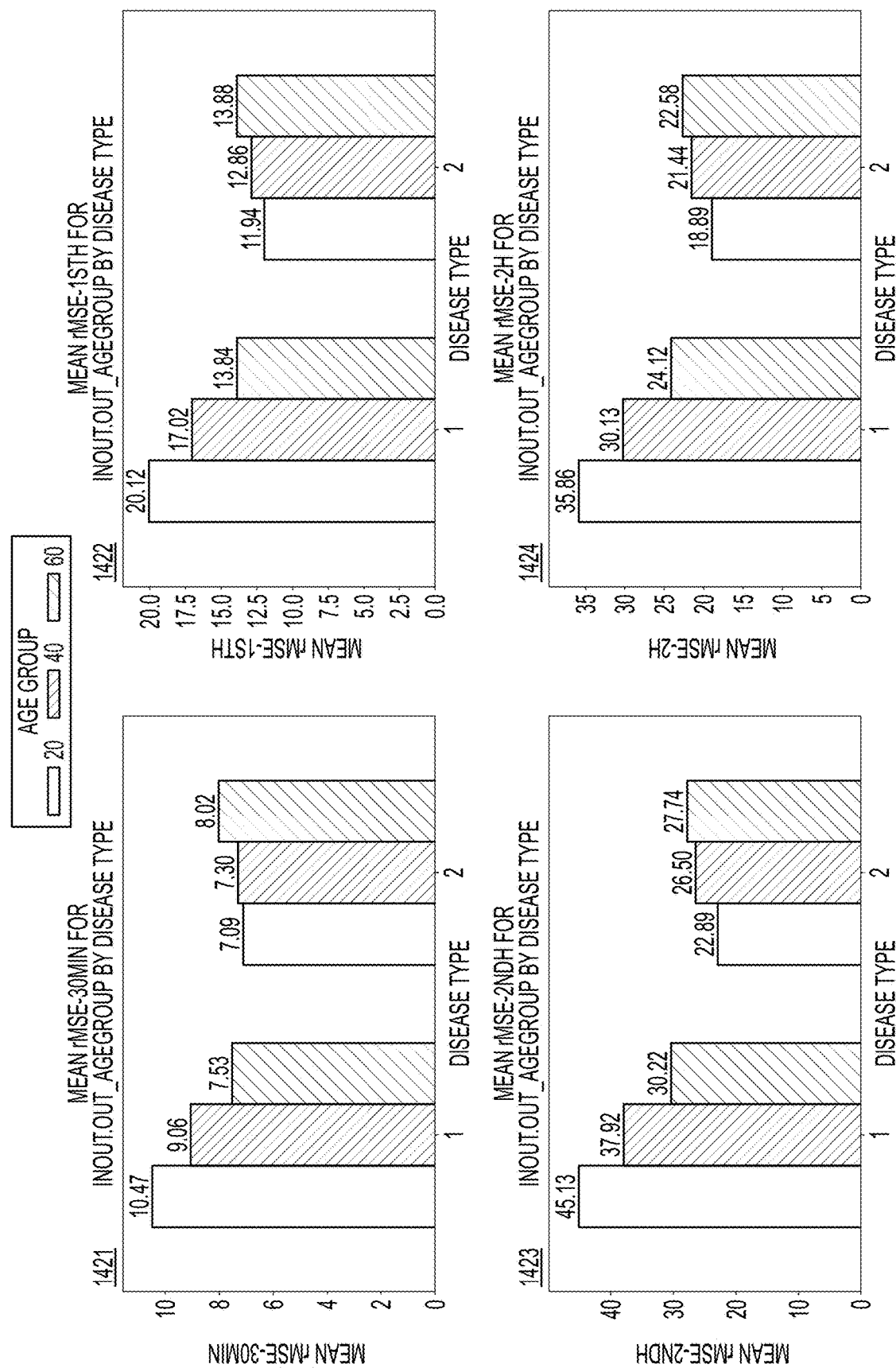

FIG. 14H depicts plot 1421, plot 1422, plot 1423, and plot 1424 showing the predicted CGM values for type 1 and type 2 diabetes patients using MEDAL tokens by age group. Plot 1421 shows the predicted CGM values for type 1 and type 2 diabetes patients using RMSE at the 30 minute interval. Plot 1422 shows the predicted CGM values for type 1 and type 2 diabetes patients using RMSE at the $1^{st}$ hour interval. Plot 1423 shows the predicted CGM values for type 1 and type 2 diabetes patients using RMSE at the $2^{nd}$ hour interval. Plot 1424 shows the predicted CGM values for type 1 and type 2 diabetes patients at the 2-hour interval.

Figure 14I:
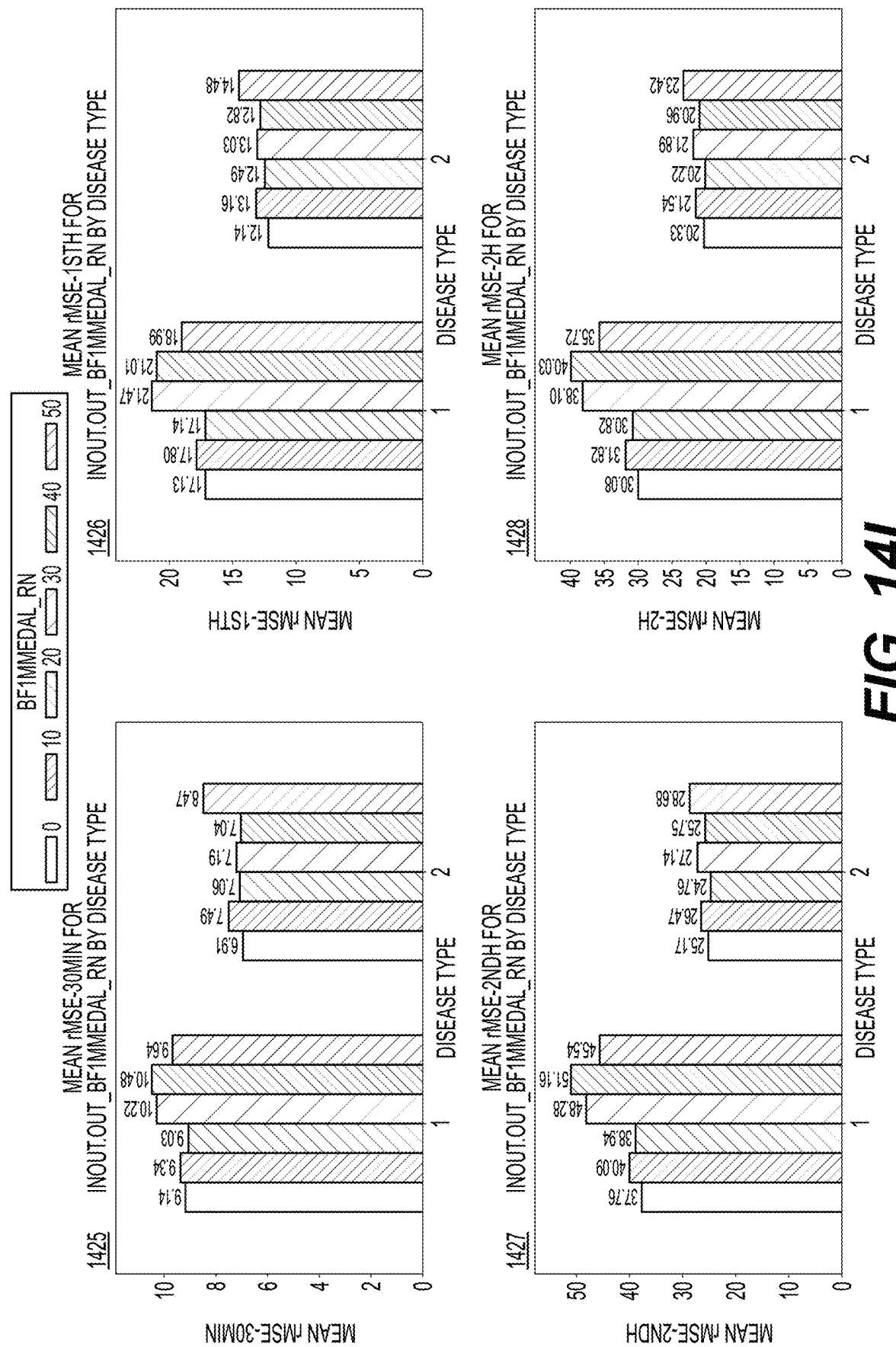

FIG. 14I depicts plot 1425, plot 1426, plot 1427, and plot 1428 showing the predicted CGM values for type 1 and type 2 diabetes patients using Bf1mMEDAL. Plot 1425 shows the predicted CGM values for type 1 and type 2 diabetes patients using RMSE at the 30 minute interval. Plot 1426 shows the predicted CGM values for type 1 and type 2 diabetes patients using RMSE at the $1^{st}$ hour interval. Plot 1427 shows the predicted CGM values for type 1 and type 2 diabetes patients using RMSE at the $2^{nd}$ hour interval. Plot 1428 shows the predicted CGM values for type 1 and type 2 diabetes patients at the 2-hour interval.

Figure 14J:
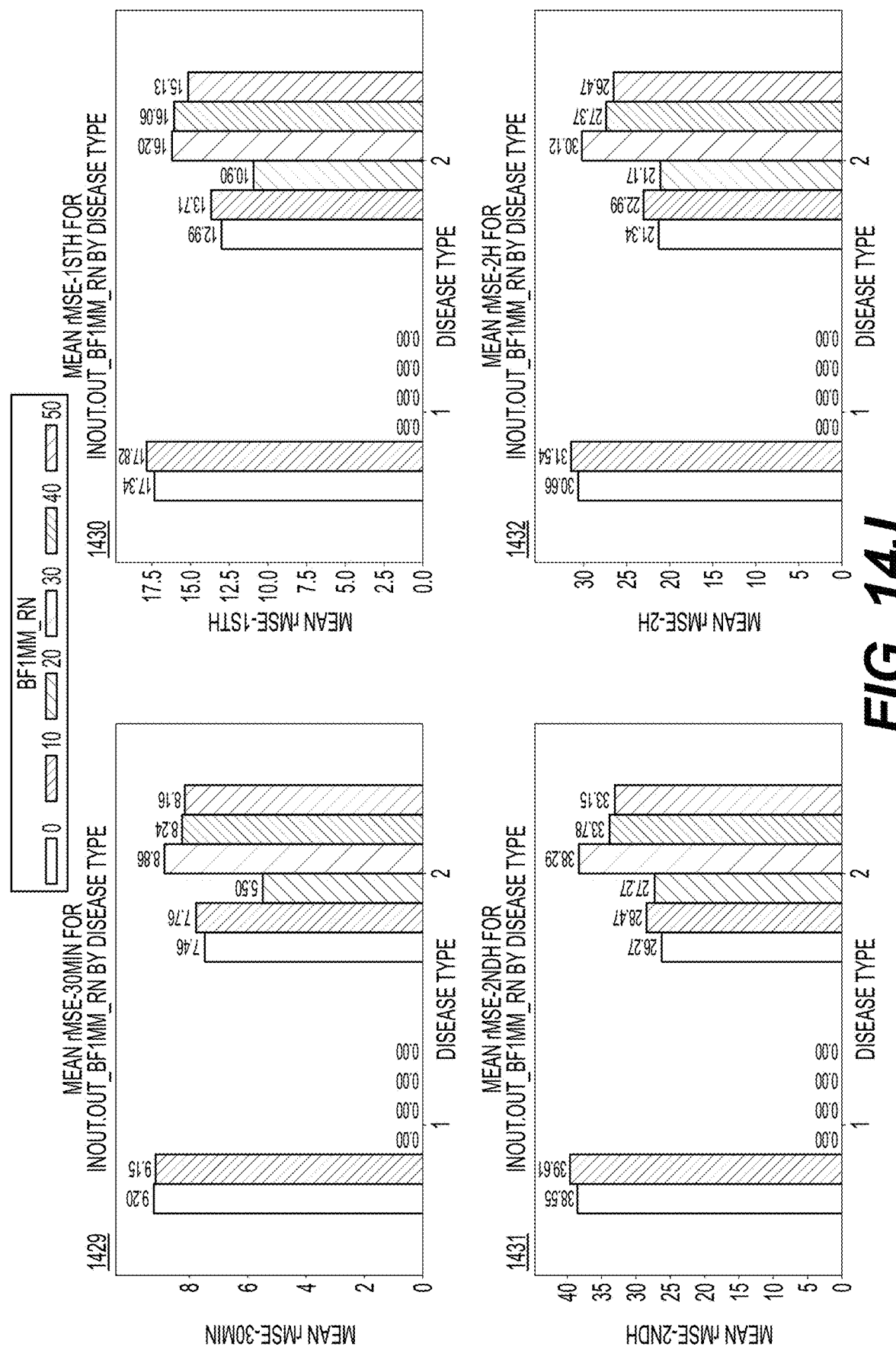

FIG. 14J depicts plot 1429, plot 1430, plot 1431, and plot 1432 showing the predicted CGM values for type 1 and type 2 diabetes patients using Mf1mM for InOut.Out. Plot 1429 shows the predicted CGM values for type 1 and type 2 diabetes patients using RMSE at the 30 minute interval. Plot 1430 shows the predicted CGM values for type 1 and type 2 diabetes patients using RMSE at the $1^{st}$ hour interval. Plot 1431 shows the predicted CGM values for type 1 and type 2 diabetes patients using RMSE at the $2^{nd}$ hour interval. Plot 1432 shows the predicted CGM values for type 1 and type 2 diabetes patients at the 2-hour interval.

Figure 14K:
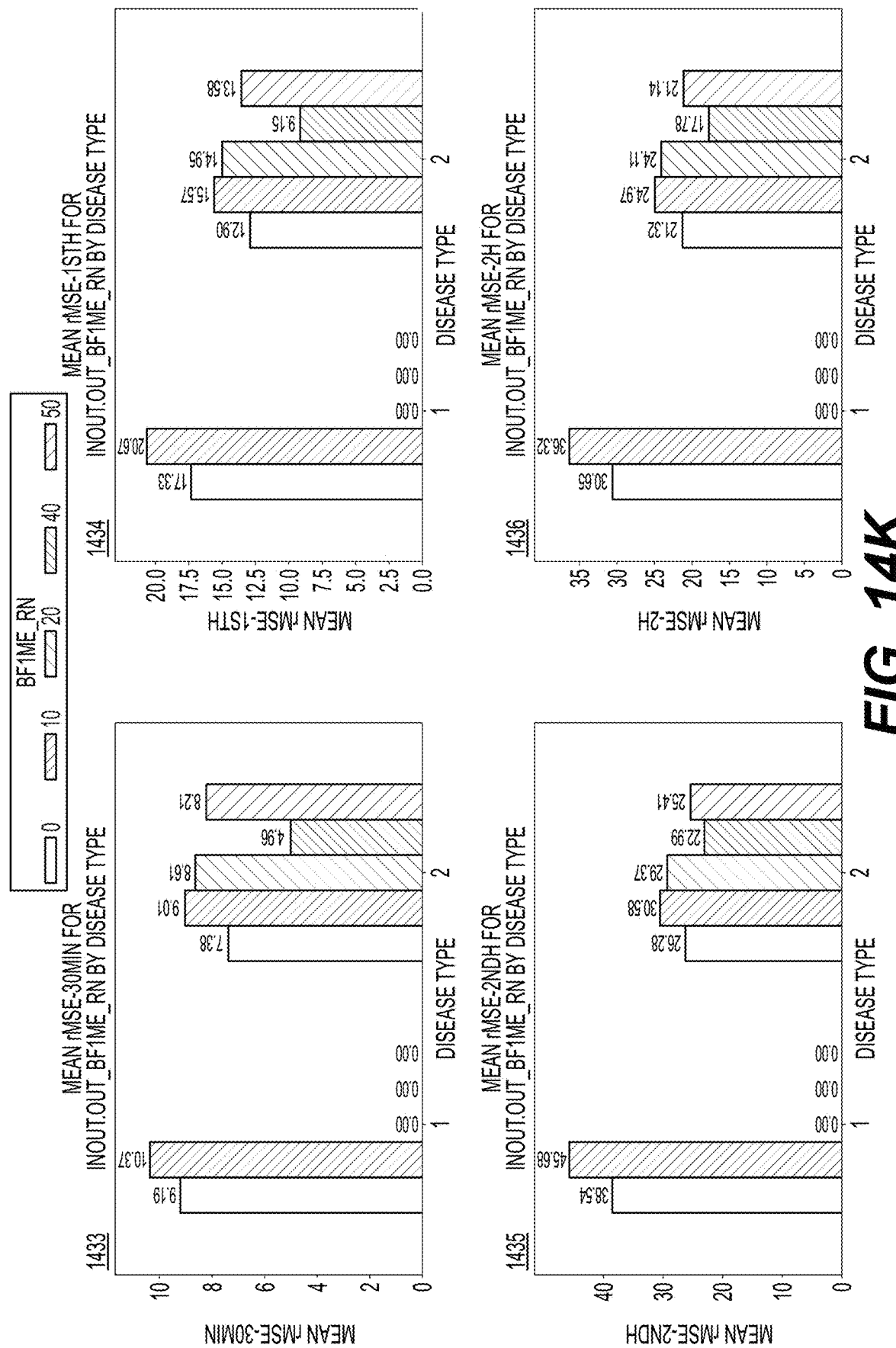

FIG. 14K depicts plot 1433, plot 1434, plot 1435, and plot 1436 showing the predicted CGM values for type 1 and type 2 diabetes patients using RMSE for Bf1mE InOut.Out. Plot 1433 shows the predicted CGM values for type 1 and type 2 diabetes patients using RMSE at the 30 minute interval. Plot 1434 shows the predicted CGM values for type 1 and type 2 diabetes patients using RMSE at the $1^{st}$ hour interval. Plot 1435 shows the predicted CGM values for type 1 and type 2 diabetes patients using RMSE at the $2^{nd}$ hour interval. Plot 1436 shows the predicted CGM values for type 1 and type 2 diabetes patients at the 2-hour interval.

Figure 14L:
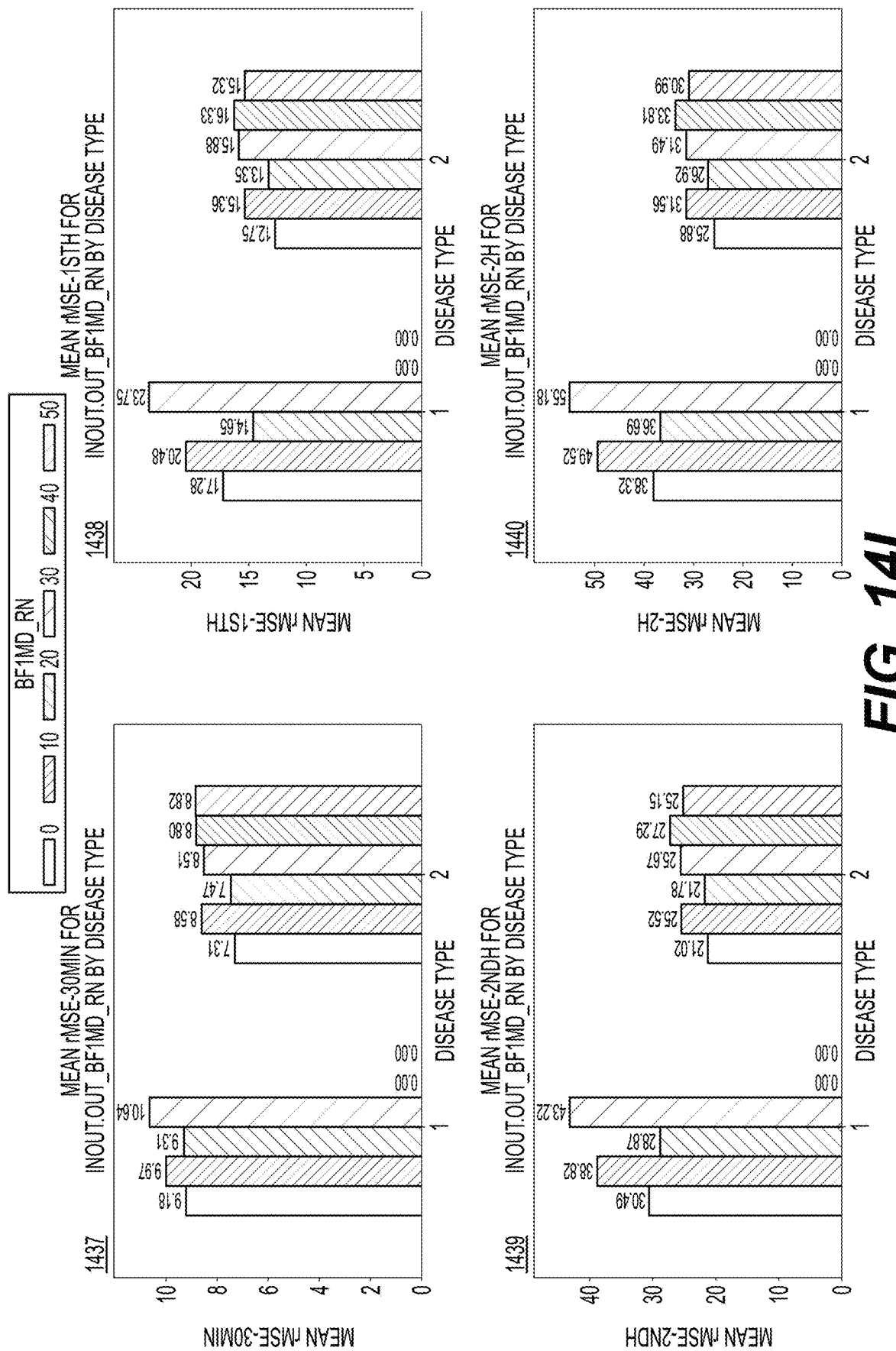

FIG. 14L depicts plot 1437, plot 1438, plot 1439, and plot 1440 showing the predicted CGM values for type 1 and type 2 diabetes patients using RMSE for Bf1mD_RN InOut.Out. Plot 1437 shows the predicted CGM values for type 1 and type 2 diabetes patients using RMSE at the 30 minute interval. Plot 1438 shows the predicted CGM values for type 1 and type 2 diabetes patients using RMSE at the $1^{st}$ hour interval. Plot 1439 shows the predicted CGM values for type 1 and type 2 diabetes patients using RMSE at the $2^{nd}$ hour interval. Plot 1440 shows the predicted CGM values for type 1 and type 2 diabetes patients at the 2-hour interval.

Figure 14M:
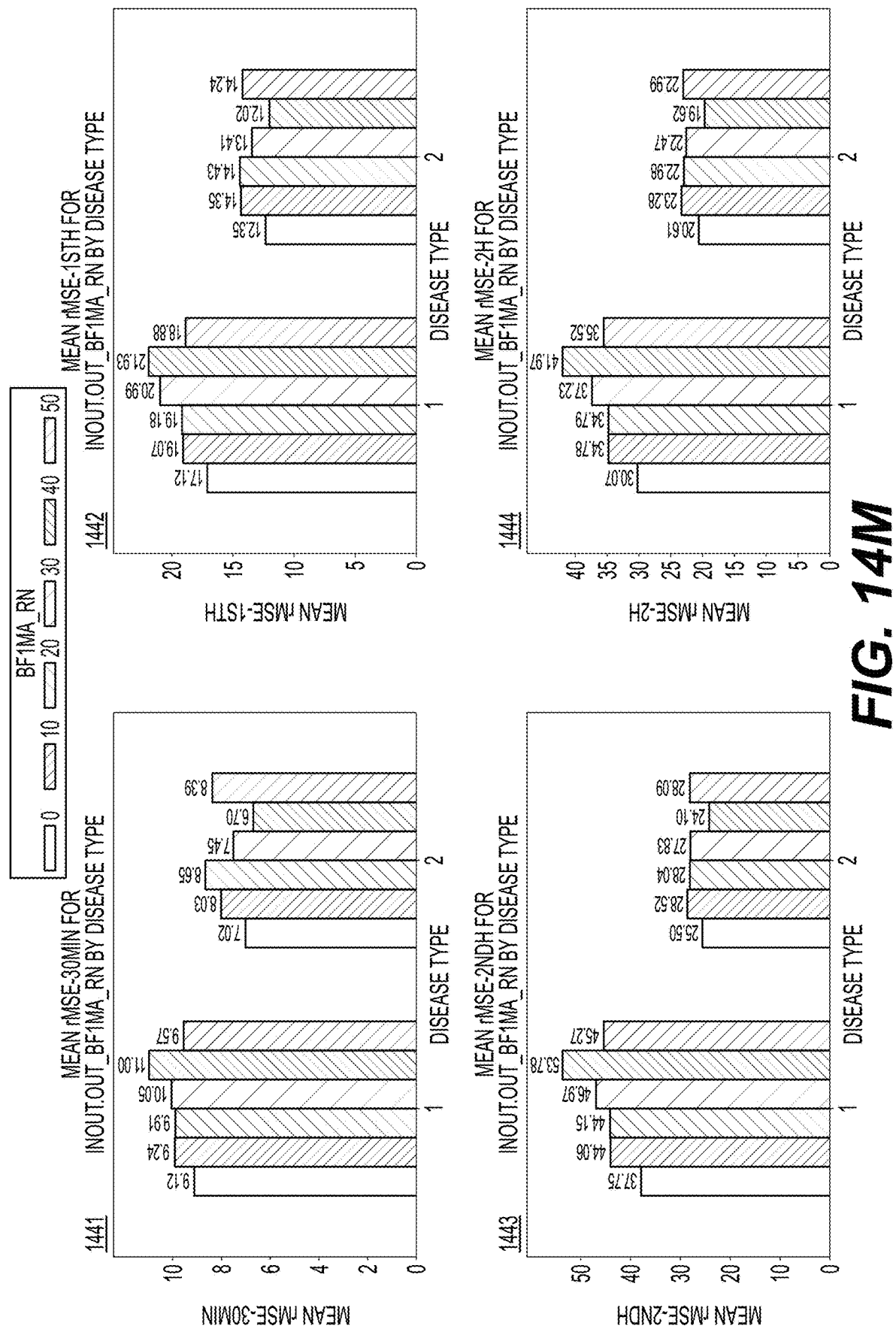

FIG. 14M depicts plot 1441, plot 1442, plot 1443, and plot 1444 showing the predicted CGM values for type 1 and type 2 diabetes patients using RMSE for InOut.Out_Bf1mA_RN. Plot 1441 shows the predicted CGM values for type 1 and type 2 diabetes patients using RMSE at the 30 minute interval. Plot 1442 shows the predicted CGM values for type 1 and type 2 diabetes patients using RMSE at the $1^{st}$ hour interval. Plot 1443 shows the predicted CGM values for type 1 and type 2 diabetes patients using RMSE at the $2^{nd}$ hour interval. Plot 1444 shows the predicted CGM values for type 1 and type 2 diabetes patients at the 2-hour interval.

Figure 14N:
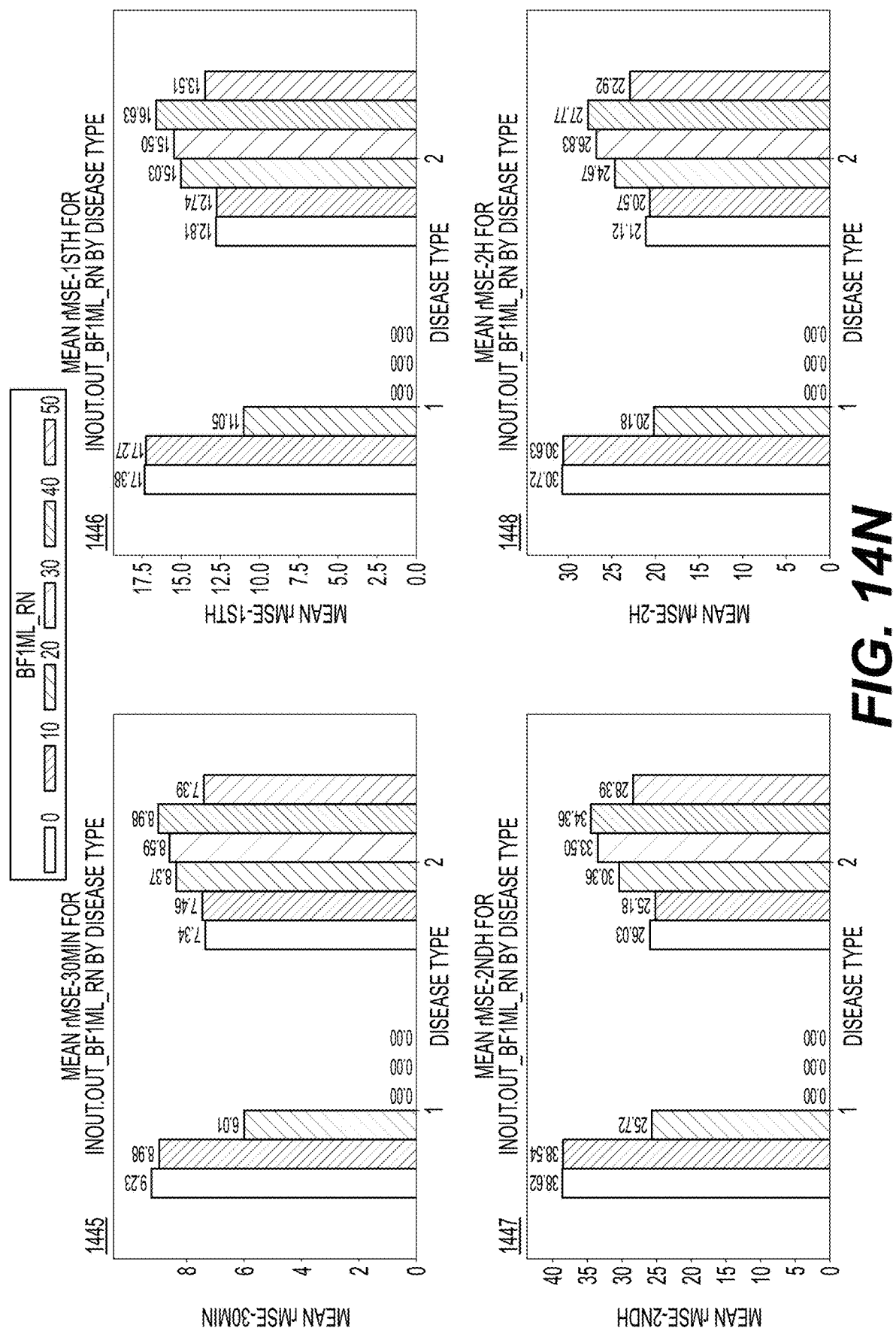

FIG. 14N depicts plot 1445, plot 1446, plot 1447, and plot 1448 showing the predicted CGM values for type 1 and type 2 diabetes patients using RMSE for InOut.Out_Bf1mL_RN. Plot 1445 shows the predicted CGM values for type 1 and type 2 diabetes patients using RMSE at the 30 minute interval. Plot 1446 shows the predicted CGM values for type 1 and type 2 diabetes patients using RMSE at the $1^{st}$ hour interval. Plot 1447 shows the predicted CGM values for type 1 and type 2 diabetes patients using RMSE at the $2^{nd}$ hour interval. Plot 1448 shows the predicted CGM values for type 1 and type 2 diabetes patients at the 2-hour interval.

It is to be understood that both the foregoing general description and the following detailed description are exemplary and explanatory only and are not restrictive of the disclosed examples, as claimed.

Other examples of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for training a machine learning model for predicting metabolic values, the method comprising:
   sensing an individual's glucose levels by a continuous glucose monitoring (CGM) device over a period of time;
   receiving the individual's glucose levels collected by the CGM device over the period of time;
   determining a first glycemia risk index (GRI) value based on a first amount of time the individual is hypoglycemic during the period of time and a second amount of time the individual is hyperglycemic during the period of time;
   determining a time in range (TIR) value of the individual's glucose level, wherein the determined TIR value is based on an amount of time the individual's glucose level is within a threshold band over the time period, wherein the threshold band is generated based on the lifestyle, habits, and medical test results of the individual;
   receiving historical metabolic values for an individual having a first medical condition, wherein the individuals historical metabolic values are associated with heart rates, heart related values, ketone values, weight values, cortisol values, hormone levels, body electrical values, repertory values, and the glucose levels collected by the CGM device;
   providing a first subset of the historical metabolic values, supplementary variables, and supplementary conditions to a machine learning model to train a generative machine learning model, wherein the first subset of the historical metabolic values includes the CGM values over the period of time, wherein the supplementary variables include the TIR value and GRI value, and wherein the supplementary condition is an anticipated dosage, anticipated time for taking a given medication, anticipated example exercise, or an anticipated example food to be consumed by the given individual;
   generating a first predicted metabolic value based on the first subset of the historical metabolic values, wherein generating the first predicted metabolic value based on the first subset of the historical metabolic values includes generating the first predicted metabolic value at a first interval;
   calculating a root mean square error (RMSE) between the first predicted metabolic value and a corresponding actual metabolic value of a second subset of the historical metabolic values;
   training the generative machine learning model to minimize the RMSE, wherein the generative machine learning model is trained to learn the distribution of the historical metabolic values, the generative machine learning model is a statistical model of the joint probability distribution on the historical metabolic values and the predicted metabolic values, wherein the generative machine learning model is used to generate random instances of the historical metabolic values and may select a given historical metabolic value from the random instances that corresponds to a highest probability of occurring, wherein the generative machine learning model determines a conditional probability of a target metabolic value based on historical metabolic values, and wherein the generative machine learning model learns patterns and structure of training data that includes the historical metabolic values to generate new data that has similar characteristic;
   generating a trained generative machine learning model based on the training, wherein the trained generative machine learning model outputs recommendations for causing the predicted metabolic value to comply with a metabolic value goal or range;
   receiving a trained generative machine learning model output;
   calculating a timing and a dosing amount of insulin for the individual based on the trained generative machine learning model output; and
   automatically administering, via an insulin pump, based on the trained generative machine learning model output, at the timing, the dosing amount of insulin to the individual.

2. The computer-implemented method of claim 1, wherein the first predicted metabolic value is one or more future CGM values over the period of time.

3. The computer-implemented method of claim 1, wherein the first medical condition includes at least one of type 1 diabetes or type 2 diabetes.

4. The computer-implemented method of claim 1, wherein the first interval includes at least one of 30 minutes, 60 minutes, or 2 hours.

5. The computer-implemented method of claim 1, further comprising:
   providing recent metabolic values associated with a first individual to the trained generative machine learning model;
   receiving a first predicted metabolic value from a trained generative machine learning model based on the recent metabolic values;
   comparing the first predicted metabolic value to a threshold metabolic value;
   determining a first action based on comparing the first predicted metabolic value to the threshold metabolic value.

6. A computer-implemented method for using a metabolic prediction trained machine learning model, the method comprising:
   sensing an individual's glucose levels by a continuous glucose monitoring (CGM) device over a period of time;
   receiving an individual's glucose levels collected by the CGM device over a period of time;

receiving historical metabolic values for an individual having a first medical condition, wherein the individual's historical metabolic values are associated with heart rates, heart related values, ketone values, weight values, cortisol values, hormone levels, body electrical values, repertory values, and the glucose levels collected by the CGM device;

providing a first subset of the historical metabolic values to a machine learning model to train a generative machine learning model, wherein the first subset of the historical metabolic values includes CGM values over the period of time;

generating a first predicted metabolic value based on the first subset of the historical metabolic values, wherein generating the first predicted metabolic value based on the first subset of the historical metabolic values includes generating the first predicted metabolic value at a first interval;

calculating a root mean square error (RMSE) between the first predicted metabolic value and a corresponding actual metabolic value of a second subset of the historical metabolic values;

training the generative machine learning model to minimize the RMSE, wherein the generative machine learning model is trained to learn the distribution of the historical metabolic values, the generative machine learning model is a statistical model of the joint probability distribution on the historical metabolic values and the predicted metabolic values, wherein the generative machine learning model is used to generate random instances of the historical metabolic values and may select a given historical metabolic value from the random instances that corresponds to a highest probability of occurring, wherein the generative machine learning model determines a conditional probability of a target metabolic value based on historical metabolic values, and wherein the generative machine learning model learns patterns and structure of training data that includes the historical metabolic values to generate new data that has similar characteristic;

generating a trained generative machine learning model based on the training;

providing recent metabolic values associated with a first individual to a trained generative learning model trained to output predicted metabolic values;

receiving a first predicted metabolic value from a trained generative machine learning model based on the recent metabolic values;

comparing first predicted metabolic value to a threshold metabolic value;

determining a first action based on comparing the first predicted metabolic value to the threshold metabolic value, wherein the first action comprises:
  determining a dosing amount of insulin based on comparing the first predicted metabolic value to the threshold metabolic value;
  determining a first time, of a timing, to administer the dosing amount of insulin based on the comparing the first predicted metabolic value to the threshold metabolic value; and
  triggering an insulin pump to administer the dosing amount of insulin at the first time;

determining a second action based on comparing the first predicted metabolic value to the threshold metabolic value;

wherein the second action comprises:
  providing a notification to the individual, wherein the notification includes at least one of an exercise recommendation, a fluid intake recommendation, a rest recommendation, an education recommendation, a food recommendation, or an insulin recommendation.

7. The computer-implemented method of claim 6, wherein the second action includes sending an instruction to an application of a user device via an application programming interface (API).

8. The computer-implemented method of claim 6, wherein the second action includes generating a food order through a mobile application.

9. The computer-implemented method of claim 6, wherein the second action includes:
  receiving a plurality of food items available to a user based on accessing a database;
  identifying a subset of food items from the plurality of food items based on comparing the first predicted metabolic value to the threshold metabolic value; and
  outputting the subset of food items to a user device.

10. The computer-implemented method of claim 6, wherein the second action includes generating an alert to medical services.

11. A system for predicting metabolic values, the system comprising:
  a memory having processor-readable instructions stored therein; and
  a processor configured to access the memory and execute the processor-readable instructions, which, when executed by the processor configures the processor to perform a method, the method comprising:
    sensing an individual's glucose levels by a continuous glucose monitoring (CGM) device over a period of time;
    receiving the individual's glucose levels collected by the CGM device over the period of time;
    determining a first glycemia risk index (GRI) value based on a first amount of time the individual is hypoglycemic during the period of time and a second amount of time the individual is hyperglycemic during the period of time;
    determining a time in range (TIR) value of the individual's glucose level, wherein the determined TIR value is based on an amount of time the individual's glucose level is within a threshold band over the time period, wherein the threshold band is generated based on the lifestyle, habits, and medical test results of the individual;
    receiving historical metabolic values for an individual having a first medical condition, wherein the individuals historical metabolic values are associated with heart rates, heart related values, ketone values, weight values, cortisol values, hormone levels, body electrical values, repertory values, and the glucose levels collected by the CGM device;
    providing a first subset of the historical metabolic values, supplementary variables, and supplementary conditions to a machine learning model to train a generative machine learning model, wherein the first subset of the historical metabolic values includes the CGM values over the period of time, wherein the supplementary variables include the TIR value and GRI value, and wherein the supplementary condition is an anticipated dosage, anticipated time for taking a given medication, anticipated example exercise, or an anticipated example food to be consumed by the given individual;

generating a first predicted metabolic value based on the first subset of the historical metabolic values, wherein generating the first predicted metabolic value based on the first subset of the historical metabolic values includes generating the first predicted metabolic value at a first interval;

calculating a root mean square error (RMSE) between the first predicted metabolic value and a corresponding actual metabolic value of a second subset of the historical metabolic values;

training the generative machine learning model to minimize the RMSE, wherein the generative machine learning model is trained to learn the distribution of the historical metabolic values, the generative machine learning model is a statistical model of the joint probability distribution on the historical metabolic values and the predicted metabolic values, wherein the generative machine learning model is used to generate random instances of the historical metabolic values and may select a given historical metabolic value from the random instances that corresponds to a highest probability of occurring, wherein the generative machine learning model determines a conditional probability of a target metabolic value based on historical metabolic values, and wherein the generative machine learning model learns patterns and structure of training data that includes the historical metabolic values to generate new data that has similar characteristic;

generating a trained generative machine learning model based on the training, wherein the trained generative machine learning model outputs recommendations for causing the predicted metabolic value to comply with a metabolic value goal or range;

receiving a trained generative machine learning model output;

calculating a timing and a dosing amount of insulin for the individual based on the trained generative machine learning model output; and automatically administering, via an insulin pump, based on the trained generative machine learning model output, at the timing, the dosing amount of insulin to the individual.

12. The system of claim 11, wherein the first predicted metabolic value is one or more future CGM values over the period of time.

13. The system of claim 11, wherein the first medical condition includes at least one of type 1 diabetes or type 2 diabetes.

14. The system of claim 11, wherein the first interval includes at least one of 30 minutes, 60 minutes, or 2 hours.

15. The system of claim 11, further comprising:
providing recent metabolic values associated with a first individual to the trained generative machine learning model;
receiving a first predicted metabolic value from a trained generative machine learning model based on the recent metabolic values;
comparing the first predicted metabolic value to a threshold metabolic value; determining a first action based on comparing the first predicted metabolic value to the threshold metabolic value.

* * * * *